US012533411B2

(12) United States Patent
Tomkinson et al.

(10) Patent No.: US 12,533,411 B2
(45) Date of Patent: Jan. 27, 2026

(54) COMPOSITIONS COMPRISING ANTI-CD38 ANTIBODIES AND CARFILZOMIB

(71) Applicants: Sanofi-Aventis U.S. LLC, Morristown, NJ (US); The Regents of the University of California, Oakland, CA (US)

(72) Inventors: Blake Tomkinson, Bridgewater, NJ (US); Blake T. Aftab, San Francisco, CA (US); Byron C. Hann, San Francisco, CA (US); Thomas G. Martin, III, San Francisco, CA (US)

(73) Assignees: Sanofi-Aventis U.S LLC, Morristown, NJ (US); The Regents of the University of California, Oakland, CA (US)

( * ) Notice: Subject to any disclaimer, the term of this patent is extended or adjusted under 35 U.S.C. 154(b) by 199 days.

(21) Appl. No.: 17/324,478

(22) Filed: May 19, 2021

(65) Prior Publication Data

US 2022/0088194 A1 Mar. 24, 2022

Related U.S. Application Data

(63) Continuation of application No. 16/375,693, filed on Apr. 4, 2019, now abandoned, which is a continuation of application No. 15/389,279, filed on Dec. 22, 2016, now abandoned, which is a continuation of application No. 14/775,641, filed as application No. PCT/US2014/025441 on Mar. 13, 2014, now abandoned.

(60) Provisional application No. 61/808,381, filed on Apr. 4, 2013, provisional application No. 61/778,540, filed on Mar. 13, 2013.

(51) Int. Cl.

| | |
|---|---|
| ***A61K 39/395*** | (2006.01) |
| ***A61K 9/00*** | (2006.01) |
| ***A61K 31/573*** | (2006.01) |
| ***A61K 38/07*** | (2006.01) |
| ***A61K 38/08*** | (2019.01) |
| ***C07K 16/28*** | (2006.01) |
| ***C07K 16/30*** | (2006.01) |
| *A61K 39/00* | (2006.01) |

(52) U.S. Cl.

CPC ...... *A61K 39/39533* (2013.01); *A61K 9/0019* (2013.01); *A61K 9/0053* (2013.01); *A61K 31/573* (2013.01); *A61K 38/07* (2013.01); *A61K 38/08* (2013.01); *A61K 39/39558* (2013.01); *C07K 16/2896* (2013.01); *C07K 16/3061* (2013.01); *A61K 2039/505* (2013.01); *A61K 2039/54* (2013.01); *A61K 2039/545* (2013.01); *C07K 2317/24* (2013.01); *C07K 2317/56* (2013.01); *C07K 2317/73* (2013.01); *C07K 2317/732* (2013.01); *C07K 2317/734* (2013.01)

(58) Field of Classification Search

CPC .............. C07K 16/2896; A61K 39/395; A61K 39/3955; A61K 39/39558; A61K 38/07; A61K 2039/505

See application file for complete search history.

(56) References Cited

U.S. PATENT DOCUMENTS

| | | | |
|---|---|---|---|
| 4,444,887 | A | 4/1984 | Hoffmann |
| 4,716,111 | A | 12/1987 | Osband et al. |
| 4,816,397 | A | 3/1989 | Boss et al. |
| 4,816,567 | A | 3/1989 | Cabilly et al. |
| 5,530,101 | A | 6/1996 | Queen et al. |
| 5,545,806 | A | 8/1996 | Lonberg et al. |
| 5,565,332 | A | 10/1996 | Hoogenboom et al. |
| 5,585,089 | A | 12/1996 | Queen et al. |
| 5,639,641 | A | 6/1997 | Pedersen et al. |
| 5,807,715 | A | 9/1998 | Morrison et al. |
| 5,814,318 | A | 9/1998 | Lonberg et al. |
| 7,232,818 | B2 | 6/2007 | Smyth et al. |
| 7,417,042 | B2 | 8/2008 | Smyth et al. |
| 7,491,704 | B2 | 2/2009 | Smyth et al. |
| 7,737,112 | B2 | 6/2010 | Lewis et al. |
| 8,129,346 | B2 | 3/2012 | Smyth et al. |
| 8,153,765 | B2 | 4/2012 | Park |
| 8,207,125 | B2 | 6/2012 | Smyth et al. |
| 8,207,126 | B2 | 6/2012 | Smyth et al. |
| 8,207,127 | B2 | 6/2012 | Smyth et al. |
| 8,207,297 | B2 | 6/2012 | Smyth et al. |
| 8,491,898 | B2 | 7/2013 | Cardarelli et al. |
| 10,184,005 | B2 | 1/2019 | Tesar et al. |
| 10,342,869 | B2 | 7/2019 | Hann et al. |
| 11,939,390 | B2 | 3/2024 | Audat et al. |
| 2009/0270419 | A1 | 10/2009 | Arts et al. |
| 2009/0304710 | A1 | 12/2009 | Park |

(Continued)

FOREIGN PATENT DOCUMENTS

| | | | |
|---|---|---|---|
| CN | 101534860 | A | 9/2009 |
| CN | 101616933 | A | 12/2009 |

(Continued)

OTHER PUBLICATIONS

McCormack (Drugs. Oct. 22, 2012; 72(15):2023-32) (Year: 2012).*
Bataille, R. et al. (Sep. 2006). "The Phenotype of Normal, Reactive and Malignant Plasma Cells. Identification of "Many and Multiple Myelomas" and of New Targets for Myeloma Therapy," *Haematologica* 91(9): 1234-1240.
De Weers et al. (Feb. 1, 2011). "Daratumumab, a Novel Therapeutic Human CD38. Monoclonal Antibody, Induces Killing of Multiple Myeloma and Other Hematological Tumors," *J. Immunol.* 186(3):1840-1848.

(Continued)

*Primary Examiner* — Meera Natarajan
(74) *Attorney, Agent, or Firm* — MORRISON & FOERSTER LLP

(57) ABSTRACT

Disclosed herein are compositions and kits which comprise anti-CD38 antibodies and carfilzomib compounds. Also disclosed are methods for treating cancers, such as multiple myeloma, in subjects with the compositions and kits.

10 Claims, 22 Drawing Sheets

Specification includes a Sequence Listing.

(56) References Cited

U.S. PATENT DOCUMENTS

| | | | |
|---|---|---|---|
| 2010/0028346 | A1 | 2/2010 | Lutz et al. |
| 2010/0092489 | A1 | 4/2010 | Van De Winkel et al. |
| 2011/0123554 | A1 | 5/2011 | Osterroth et al. |
| 2011/0262454 | A1 | 10/2011 | Park et al. |
| 2012/0082670 | A1 | 4/2012 | Konopitzky et al. |
| 2012/0156218 | A1 | 6/2012 | Park et al. |
| 2014/0161819 | A1 | 6/2014 | Hann et al. |
| 2015/0118251 | A1 | 4/2015 | Deslandes et al. |
| 2016/0022813 | A1 | 1/2016 | Tomkinson |
| 2017/0106085 | A1 | 4/2017 | Tomkinson |
| 2017/0343550 | A1 | 11/2017 | Park et al. |
| 2018/0022814 | A1 | 1/2018 | Deslandes et al. |
| 2019/0284294 | A1 | 9/2019 | Deslandes et al. |
| 2019/0321471 | A1 | 10/2019 | Tomkinson |
| 2020/0046832 | A1 | 2/2020 | Hann et al. |
| 2020/0239589 | A1 | 7/2020 | Audat |
| 2020/0408765 | A1 | 12/2020 | Park et al. |
| 2022/0135696 | A1 | 5/2022 | Semiond et al. |
| 2024/0190984 | A1 | 6/2024 | Audat et al. |
| 2025/0177519 | A1 | 6/2025 | Chiron Blondel et al. |
| 2025/0216392 | A1 | 7/2025 | Park et al. |

FOREIGN PATENT DOCUMENTS

| | | | |
|---|---|---|---|
| CN | 102065891 | A | 5/2011 |
| CN | 102264386 | A | 11/2011 |
| CN | 102573916 | A | 7/2012 |
| EP | 0 239 400 | A2 | 9/1987 |
| EP | 0 519 596 | A1 | 12/1992 |
| EP | 0 592 106 | A1 | 4/1994 |
| EP | 1 914 242 | A1 | 4/2008 |
| JP | 2010-506582 | A | 3/2010 |
| JP | 2012-506445 | A | 3/2012 |
| RU | 2006132045 | A | 3/2008 |
| RU | 2007134661 | A | 3/2009 |
| RU | 2425841 | C2 | 8/2011 |
| RU | 2456990 | C2 | 7/2012 |
| WO | WO-1991/09967 | A1 | 7/1991 |
| WO | WO-1991/10741 | A1 | 7/1991 |
| WO | WO-1992/22653 | A1 | 12/1992 |
| WO | WO-1996/33735 | A1 | 10/1996 |
| WO | WO-1996/34096 | A1 | 10/1996 |
| WO | WO-1998/16654 | A1 | 4/1998 |
| WO | WO-1998/24893 | A2 | 6/1998 |
| WO | WO-1998/24893 | A3 | 6/1998 |
| WO | WO-1998/46645 | A2 | 10/1998 |
| WO | WO-1998/46645 | A3 | 10/1998 |
| WO | WO-1998/50433 | A2 | 11/1998 |
| WO | WO-1998/50433 | A3 | 11/1998 |
| WO | WO-2006/088951 | A2 | 8/2006 |
| WO | WO-2008/047242 | A2 | 4/2008 |
| WO | WO-2008/047242 | A3 | 4/2008 |
| WO | WO-2009/032661 | A1 | 3/2009 |
| WO | WO-2010/048298 | A1 | 4/2010 |
| WO | WO-2010/057048 | A1 | 5/2010 |
| WO | WO-2010/061359 | A1 | 6/2010 |
| WO | WO-2012/041800 | A1 | 4/2012 |
| WO | WO-2012/066058 | A1 | 5/2012 |
| WO | WO-2012/076663 | A1 | 6/2012 |
| WO | WO-2012/135528 | A2 | 10/2012 |

OTHER PUBLICATIONS

Dimopoulos, M.A. et al. (Jul. 2010). "Lenalidomide and Dexamethasone for the Treatment of Refractory/Relapsed Multiple Myeloma: Dosing of Lenalidomide According to Renal Function and Effect on Renal Impairment," *Eur. J. Haematology* 85(1):1-5.

European communication Pursuant to Article 94(3) EPC mailed on Oct. 9, 2017, for EP Application No. 14773270.5 filed on Mar. 13, 2014, four pages.

European communication Pursuant to Rules 70(2) and 70a(2) EPC mailed Oct. 5, 2016 for EP Application No. 14773270.5 filed on Mar. 13, 2014, one page.

Extended European Search Report mailed Sep. 16, 2016 for EP Application No. 14773270.5 filed on Mar. 13, 2014, eight pages.

Gillies, S.D. et al. (Dec. 20, 1989). "High-Level Expression of Chimeric Antibodies Using Adapted cDNA Variable Region Cassettes," *J. Immunol. Methods* 125(1-2):191-202.

International Search Report mailed on Jul. 24, 2014, for PCT Patent Application No. PCT/US2014/025441, filed on Mar. 13, 2014, five pages.

Kim, D. et al. (Dec. 2012). "$CD19^-CD45^{Low/-}CD38^{High/}CD138^+$ Plasma Cells Enrich for Human Tumorigenic Myeloma Cells," *Leukemia* 26(12):2530-2537.

Kurtin, S.E. (Nov./Dec. 2013). "Relapsed or Relapsed/Refractory Multiple Myelome," *J Adv. Pract. Oncol.* 4(6-Supp. 1): 5-14, (Exhibit B).

Liu, N. et al. (Jan. 2013). "Novel Agents for Relapsed/Refractory Multiple Myeloma," *Journal of Leukemia & Lymphoma* 22(1):35-47, 46, (four pages) (English Abstract only).

Martin, T.G. et al. (Dec. 3-6, 2016). "2111 Phase 1b Study of Isatuximab and Carfilzomib in Relapse and Refractory Multiple Myeloma," presented at *ASH 58$^{th}$ Annual Meeting & Exposition*, San Diego, CA, two pages, (Exhibit A).

Moreau, P. et al. (2020, e-pub Dec. 13, 2019). "Isatuximab Plus Carfilzomib And Dexamethasone Vs Carfilzomib And Dexamethasone In Relapsed/Refractory Multiple Myeloma: IKEMA Phase III Study Design," Future Oncology 4347-4358.

Morrison, S.L. (Sep. 20, 1985). "Transfectomas Provide Novel Chimeric Antibodies," *Science* 229(4719):1202-1207.

Oi, V.T. et al. (1986). "Chimeric Antibodies," *BioTechniques* 4(3):214-221.

Padlan, E.A. (Apr.-May 1991). "A Possible Procedure for Reducing the Immunogenicity of Antibody Variable Domains While Preserving Their Ligand-Binding Properties," *Mol. Immunol.* 28(4-5):489-498.

Rajkumar, S.V. et al. (2011). "Consensus Recommendations For The Uniform Reporting Of Clinical Trials: Report Of The International Myelomaworkshop Consensus Panel 1," *Blood* 117(18):4691-4695, (Exhibit C).

Richardson, P.G. et al., (2011) "Monoclonal Antibodies in the Treatment of Multiple Myeloma," *Br. J. Haematol.* 154:745-54.

Roguska, M.A. et al. (Feb. 1, 1994). "Humanization of Murine Monoclonal Antibodies Through Variable Domain Resurfacing," *PNAS* 91(3):969-973.

Studnicka, G.M. et al. (Jun. 1994). "Human-Engineered Monoclonal Antibodies Retain Full Specific Binding Activity by Preserving Non-CDR Complementarity-Modulating Residues," *Protein Eng.* 7(6):805-814.

Van Der Veer, M.S. et al. (Feb. 2011). "Towards Effective Immunotherapy of Myeloma: Enhanced Elimination of Myeloma Cells by Combination of Lenalidomide with the Human CD38 Monoclonal Antibody Daratumumab," *Haematologica* 96(2):284-290.

Wang, et al. (2011) Abstract #8025, 2011 ASCO Annual Meeting, *J. Clin Oncol.* 29:2011 (suppl; abstr 8025).

Wang, H. et al. (Mar. 1, 2004). "Pretreatment with Dexamethasone Increases Antitumor Activity of Carboplatin and Gemcitabine in Mice Bearing Human Cancer Xenografts," *Clinical Cancer Research* 10(5):1633-1644.

Wetzel, M-C. et al. (Apr. 15, 2013). "Abstract 4735: SAR650984: Characterization of a Potent Phase I Humanized Anti-CD38 Antibody for the Treatment of Multiple Myeloma and Other Hematologic Malignancies," Proceedings: AACR 104th Annual Meeting 2013, Washington, D.C., *Cancer Res.*, 73:4735, located at http://cancerres.aacrjournals.org/content/73/8_Supplement/4735, last visited on Jan. 19, 2016, two pages.

Yang, S. et al. (2004). "Expression of Leucocyte Cell-Surface Antigens on Colon Cancer Cell Line HR8348," *Journal of Zhejiang University* (*Medical Sciences*) 33(2): 118-120, (English Abstract only).

Kuhn, D.J. et al. (Nov. 1, 2007). "Potent Activity Of Carfilzomib, A Novel, Irreversible Inhibitor Of The Ubiquitin-Proteasome Pathway, Against Preclinical Models Of Multiple Myeloma," Blood 110(9):3281-3290.

(56) References Cited

OTHER PUBLICATIONS

Schots, R. et al. (Apr. 30, 2011). "Recent Advances In Myeloma Treatment," Transfusion and Apheresis Science 44 (2):223-229.
Zhang, Y.C. editor (2011). Immune Disease, pp. 646, total 5 pages with English Translation.
U.S. Appl. No. 14/687,179, filed Apr. 15, 2015, for Peter U. U. Park et al.
U.S. Appl. No. 15/931,466, filed May 13, 2020, for Heloise Audat et al.
U.S. Appl. No. 16/249,538, filed Jan. 16, 2019, for Peter U. U. Park et al.
U.S. Appl. No. 16/526,969, filed Jul. 30, 2019, for Peter U. U. Park et al.
U.S. Appl. No. 17/112,862, filed Dec. 4, 2020, for Marie-Laure Risse et al.
U.S. Appl. No. 18/391,403, filed Dec. 20, 2023, for Peter U. U. Park et al.

* cited by examiner

11/22

SEQUENCE LISTING

```
<160> NUMBER OF SEQ ID NOS: 81

<210> SEQ ID NO 1
<211> LENGTH: 5
<212> TYPE: PRT
<213> ORGANISM: Mus sp.

<400> SEQUENCE: 1
```

Ser Tyr Gly Met Asn
1 5

<210> SEQ ID NO 2
<211> LENGTH: 17
<212> TYPE: PRT
<213> ORGANISM: Mus sp.

<400> SEQUENCE: 2

Trp Ile Asn Thr Tyr Thr Gly Glu Pro Thr Tyr Ala Asp Asp Phe Lys
1 5 10 15

Gly

<210> SEQ ID NO 3
<211> LENGTH: 5
<212> TYPE: PRT
<213> ORGANISM: Mus sp.

<400> SEQUENCE: 3

Arg Gly Phe Ala Tyr
1 5

<210> SEQ ID NO 4
<211> LENGTH: 15
<212> TYPE: PRT
<213> ORGANISM: Mus sp.

<400> SEQUENCE: 4

Arg Ala Ser Glu Ser Val Glu Ile Tyr Gly Asn Gly Phe Met Asn
1 5 10 15

<210> SEQ ID NO 5
<211> LENGTH: 7
<212> TYPE: PRT
<213> ORGANISM: Mus sp.

<400> SEQUENCE: 5

Arg Ala Ser Asn Leu Glu Ser
1 5

<210> SEQ ID NO 6
<211> LENGTH: 9
<212> TYPE: PRT
<213> ORGANISM: Mus sp.

<400> SEQUENCE: 6

Gln Gln Ile Asn Glu Asp Pro Phe Thr
1 5

<210> SEQ ID NO 7
<211> LENGTH: 5
<212> TYPE: PRT
<213> ORGANISM: Mus sp.

<400> SEQUENCE: 7

Asn Ser Gly Met Asn
1 5

<210> SEQ ID NO 8
<211> LENGTH: 17
<212> TYPE: PRT
<213> ORGANISM: Mus sp.

<400> SEQUENCE: 8

```
Trp Ile Asn Thr Tyr Thr Gly Glu Pro Thr Tyr Ala Asp Asp Phe Lys
1               5                   10                  15

Gly


<210> SEQ ID NO 9
<211> LENGTH: 5
<212> TYPE: PRT
<213> ORGANISM: Mus sp.

<400> SEQUENCE: 9

Arg Gly Phe Val Tyr
1               5


<210> SEQ ID NO 10
<211> LENGTH: 15
<212> TYPE: PRT
<213> ORGANISM: Mus sp.

<400> SEQUENCE: 10

Arg Ala Ser Glu Ser Val Ala Ile Tyr Gly Asn Ser Phe Leu Lys
1               5                   10                  15


<210> SEQ ID NO 11
<211> LENGTH: 7
<212> TYPE: PRT
<213> ORGANISM: Mus sp.

<400> SEQUENCE: 11

Arg Ala Ser Asn Leu Glu Ser
1               5


<210> SEQ ID NO 12
<211> LENGTH: 9
<212> TYPE: PRT
<213> ORGANISM: Mus sp.

<400> SEQUENCE: 12

Gln Gln Ile Asn Glu Asp Pro Tyr Thr
1               5


<210> SEQ ID NO 13
<211> LENGTH: 5
<212> TYPE: PRT
<213> ORGANISM: Mus sp.

<400> SEQUENCE: 13

Asp Tyr Trp Met Gln
1               5


<210> SEQ ID NO 14
<211> LENGTH: 17
<212> TYPE: PRT
<213> ORGANISM: Mus sp.

<400> SEQUENCE: 14

Thr Ile Tyr Pro Gly Asp Gly Asp Thr Gly Tyr Ala Gln Lys Phe Lys
1               5                   10                  15

Gly


<210> SEQ ID NO 15
<211> LENGTH: 11
<212> TYPE: PRT
<213> ORGANISM: Mus sp.
```

<400> SEQUENCE: 15

Gly Asp Tyr Tyr Gly Ser Asn Ser Leu Asp Tyr
1 5 10

<210> SEQ ID NO 16
<211> LENGTH: 11
<212> TYPE: PRT
<213> ORGANISM: Mus sp.

<400> SEQUENCE: 16

Lys Ala Ser Gln Asp Val Ser Thr Val Val Ala
1 5 10

<210> SEQ ID NO 17
<211> LENGTH: 7
<212> TYPE: PRT
<213> ORGANISM: Mus sp.

<400> SEQUENCE: 17

Ser Ala Ser Tyr Arg Tyr Ile
1 5

<210> SEQ ID NO 18
<211> LENGTH: 9
<212> TYPE: PRT
<213> ORGANISM: Mus sp.

<400> SEQUENCE: 18

Gln Gln His Tyr Ser Pro Pro Tyr Thr
1 5

<210> SEQ ID NO 19
<211> LENGTH: 5
<212> TYPE: PRT
<213> ORGANISM: Mus sp.

<400> SEQUENCE: 19

Gly Ser Trp Met Asn
1 5

<210> SEQ ID NO 20
<211> LENGTH: 17
<212> TYPE: PRT
<213> ORGANISM: Mus sp.

<400> SEQUENCE: 20

Arg Ile Tyr Pro Gly Asp Gly Asp Ile Ile Tyr Asn Gly Asn Phe Arg
1 5 10 15

Asp

<210> SEQ ID NO 21
<211> LENGTH: 10
<212> TYPE: PRT
<213> ORGANISM: Mus sp.

<400> SEQUENCE: 21

Trp Gly Thr Phe Thr Pro Ser Phe Asp Tyr
1 5 10

<210> SEQ ID NO 22
<211> LENGTH: 11
<212> TYPE: PRT
<213> ORGANISM: Mus sp.

<400> SEQUENCE: 22

Lys Ala Ser Gln Asp Val Val Thr Ala Val Ala
1 5 10

<210> SEQ ID NO 23
<211> LENGTH: 7
<212> TYPE: PRT
<213> ORGANISM: Mus sp.

<400> SEQUENCE: 23

Ser Ala Ser His Arg Tyr Thr
1 5

<210> SEQ ID NO 24
<211> LENGTH: 9
<212> TYPE: PRT
<213> ORGANISM: Mus sp.

<400> SEQUENCE: 24

Gln Gln His Tyr Thr Thr Pro Thr Thr
1 5

<210> SEQ ID NO 25
<211> LENGTH: 5
<212> TYPE: PRT
<213> ORGANISM: Mus sp.

<400> SEQUENCE: 25

Ser Tyr Thr Leu Ser
1 5

<210> SEQ ID NO 26
<211> LENGTH: 17
<212> TYPE: PRT
<213> ORGANISM: Mus sp.

<400> SEQUENCE: 26

Thr Ile Ser Ile Gly Gly Arg Tyr Thr Tyr Tyr Pro Asp Ser Val Glu
1 5 10 15

Gly

<210> SEQ ID NO 27
<211> LENGTH: 8
<212> TYPE: PRT
<213> ORGANISM: Mus sp.

<400> SEQUENCE: 27

Asp Phe Asn Gly Tyr Ser Asp Phe
1 5

<210> SEQ ID NO 28
<211> LENGTH: 11
<212> TYPE: PRT
<213> ORGANISM: Mus sp.

<400> SEQUENCE: 28

Lys Ala Ser Gln Val Val Gly Ser Ala Val Ala
1 5 10

<210> SEQ ID NO 29
<211> LENGTH: 7
<212> TYPE: PRT
<213> ORGANISM: Mus sp.

<400> SEQUENCE: 29

Trp Ala Ser Thr Arg His Thr
1 5

<210> SEQ ID NO 30
<211> LENGTH: 9
<212> TYPE: PRT
<213> ORGANISM: Mus sp.

<400> SEQUENCE: 30

Gln Gln Tyr Asn Ser Tyr Pro Tyr Thr
1 5

<210> SEQ ID NO 31
<211> LENGTH: 5
<212> TYPE: PRT
<213> ORGANISM: Mus sp.

<400> SEQUENCE: 31

Asn Phe Gly Met His
1 5

<210> SEQ ID NO 32
<211> LENGTH: 17
<212> TYPE: PRT
<213> ORGANISM: Mus sp.

<400> SEQUENCE: 32

Tyr Ile Arg Ser Gly Ser Gly Thr Ile Tyr Tyr Ser Asp Thr Val Lys
1 5 10 15

Gly

<210> SEQ ID NO 33
<211> LENGTH: 11
<212> TYPE: PRT
<213> ORGANISM: Mus sp.

<400> SEQUENCE: 33

Ser Tyr Tyr Asp Phe Gly Ala Trp Phe Ala Tyr
1 5 10

<210> SEQ ID NO 34
<211> LENGTH: 11
<212> TYPE: PRT
<213> ORGANISM: Mus sp.

<400> SEQUENCE: 34

Lys Ala Ser Gln Asn Val Gly Thr Asn Val Ala
1 5 10

<210> SEQ ID NO 35
<211> LENGTH: 7
<212> TYPE: PRT
<213> ORGANISM: Mus sp.

<400> SEQUENCE: 35

Ser Ala Ser Ser Arg Tyr Ser
1 5

<210> SEQ ID NO 36
<211> LENGTH: 9
<212> TYPE: PRT
<213> ORGANISM: Mus sp.

```
<400> SEQUENCE: 36

Gln Gln Tyr Asn Ser Tyr Pro Leu Thr
1               5


<210> SEQ ID NO 37
<211> LENGTH: 336
<212> TYPE: DNA
<213> ORGANISM: Mus sp.
<220> FEATURE:
<221> NAME/KEY: CDS
<222> LOCATION: (1)..(336)

<400> SEQUENCE: 37

aac att gtg ctg acc caa tct cca gct tct ttg gct gtg tct ctt ggg       48
Asn Ile Val Leu Thr Gln Ser Pro Ala Ser Leu Ala Val Ser Leu Gly
1               5                   10                  15

cag agg gcc acc ata tcc tgc aga gcc agt gaa agt gtt gag att tat       96
Gln Arg Ala Thr Ile Ser Cys Arg Ala Ser Glu Ser Val Glu Ile Tyr
            20                  25                  30

ggc aat ggt ttt atg aac tgg ttc cag cag aaa cca gga cag cca ccc      144
Gly Asn Gly Phe Met Asn Trp Phe Gln Gln Lys Pro Gly Gln Pro Pro
        35                  40                  45

aaa ctc ctc atc tat cgt gca tcc aac cta gaa tct ggg atc cct gcc      192
Lys Leu Leu Ile Tyr Arg Ala Ser Asn Leu Glu Ser Gly Ile Pro Ala
    50                  55                  60

agg ttc agt ggc agt ggg tct agg aca gag ttc acc ctc acc att gat      240
Arg Phe Ser Gly Ser Gly Ser Arg Thr Glu Phe Thr Leu Thr Ile Asp
65                  70                  75                  80

cct gtg gag gct gat gat gtt gca acc tat tac tgt caa caa att aat      288
Pro Val Glu Ala Asp Asp Val Ala Thr Tyr Tyr Cys Gln Gln Ile Asn
                85                  90                  95

gag gat cca ttc acg ttc ggc tcg ggg aca aag ttg gaa ata aaa cgg      336
Glu Asp Pro Phe Thr Phe Gly Ser Gly Thr Lys Leu Glu Ile Lys Arg
            100                 105                 110


<210> SEQ ID NO 38
<211> LENGTH: 112
<212> TYPE: PRT
<213> ORGANISM: Mus sp.

<400> SEQUENCE: 38

Asn Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Glu Ile Tyr
            20                  25                  30

Gly Asn Gly Phe Met Asn Trp Phe Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Glu Phe Thr Leu Thr Ile Asp
65                  70                  75                  80

Pro Val Glu Ala Asp Asp Val Ala Thr Tyr Tyr Cys Gln Gln Ile Asn
                85                  90                  95

Glu Asp Pro Phe Thr Phe Gly Ser Gly Thr Lys Leu Glu Ile Lys Arg
            100                 105                 110


<210> SEQ ID NO 39
<211> LENGTH: 336
<212> TYPE: DNA
<213> ORGANISM: Mus sp.
```

```
<220> FEATURE:
<221> NAME/KEY: CDS
<222> LOCATION: (1)..(336)

<400> SEQUENCE: 39

gac att gta ctg acc caa tct cca gct tct ttg gct gtg tct cta ggg       48
Asp Ile Val Leu Thr Gln Ser Pro Ala Ser Leu Ala Val Ser Leu Gly
1               5                   10                  15

cag agg gcc acc ata tcc tgc aga gcc agt gag agt gtt gct att tat       96
Gln Arg Ala Thr Ile Ser Cys Arg Ala Ser Glu Ser Val Ala Ile Tyr
            20                  25                  30

ggc aat agt ttt ctg aaa tgg ttc cag cag aaa ccg gga cag cca ccc      144
Gly Asn Ser Phe Leu Lys Trp Phe Gln Gln Lys Pro Gly Gln Pro Pro
        35                  40                  45

aaa ctc ctc atc tat cgt gca tcc aac cta gaa tct ggg atc cct gcc      192
Lys Leu Leu Ile Tyr Arg Ala Ser Asn Leu Glu Ser Gly Ile Pro Ala
    50                  55                  60

agg ttc agt ggc agt ggg tct ggg aca gac ttc acc ctc acc att aat      240
Arg Phe Ser Gly Ser Gly Ser Gly Thr Asp Phe Thr Leu Thr Ile Asn
65                  70                  75                  80

cct gtg gag gct gat gat gtt gca acc tat tac tgt cag caa att aat      288
Pro Val Glu Ala Asp Asp Val Ala Thr Tyr Tyr Cys Gln Gln Ile Asn
                85                  90                  95

gag gat ccg tac acg ttc gga ggg ggg acc aag ctg gaa ata aaa cgg      336
Glu Asp Pro Tyr Thr Phe Gly Gly Gly Thr Lys Leu Glu Ile Lys Arg
            100                 105                 110


<210> SEQ ID NO 40
<211> LENGTH: 112
<212> TYPE: PRT
<213> ORGANISM: Mus sp.

<400> SEQUENCE: 40

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Ala Ile Tyr
            20                  25                  30

Gly Asn Ser Phe Leu Lys Trp Phe Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Gly Thr Asp Phe Thr Leu Thr Ile Asn
65                  70                  75                  80

Pro Val Glu Ala Asp Asp Val Ala Thr Tyr Tyr Cys Gln Gln Ile Asn
                85                  90                  95

Glu Asp Pro Tyr Thr Phe Gly Gly Gly Thr Lys Leu Glu Ile Lys Arg
            100                 105                 110


<210> SEQ ID NO 41
<211> LENGTH: 324
<212> TYPE: DNA
<213> ORGANISM: Mus sp.
<220> FEATURE:
<221> NAME/KEY: CDS
<222> LOCATION: (1)..(324)

<400> SEQUENCE: 41

gac att gtg atg gcc cag tct cac aaa ttc atg tcc aca tca gtt gga       48
Asp Ile Val Met Ala Gln Ser His Lys Phe Met Ser Thr Ser Val Gly
1               5                   10                  15

gac agg gtc agc atc acc tgc aag gcc agt cag gat gtg agt act gtt       96
```

-continued

```
Asp Arg Val Ser Ile Thr Cys Lys Ala Ser Gln Asp Val Ser Thr Val
            20                  25                  30

gtg gcc tgg tat caa cag aaa cca gga caa tct cct aaa cga ctg att      144
Val Ala Trp Tyr Gln Gln Lys Pro Gly Gln Ser Pro Lys Arg Leu Ile
        35                  40                  45

tac tcg gca tcc tat cgg tat att gga gtc cct gat cgc ttc act ggc      192
Tyr Ser Ala Ser Tyr Arg Tyr Ile Gly Val Pro Asp Arg Phe Thr Gly
    50                  55                  60

agt gga tct ggg acg gat ttc act ttc acc atc agc agt gtg cag gct      240
Ser Gly Ser Gly Thr Asp Phe Thr Phe Thr Ile Ser Ser Val Gln Ala
65                  70                  75                  80

gaa gac ctg gca gtt tat tac tgt cag caa cat tat agt cct ccg tac      288
Glu Asp Leu Ala Val Tyr Tyr Cys Gln Gln His Tyr Ser Pro Pro Tyr
                85                  90                  95

acg ttc gga ggg ggg acc aag ctg gaa ata aaa cgg                      324
Thr Phe Gly Gly Gly Thr Lys Leu Glu Ile Lys Arg
            100                 105


<210> SEQ ID NO 42
<211> LENGTH: 108
<212> TYPE: PRT
<213> ORGANISM: Mus sp.

<400> SEQUENCE: 42

Asp Ile Val Met Ala Gln Ser His Lys Phe Met Ser Thr Ser Val Gly
1               5                   10                  15

Asp Arg Val Ser Ile Thr Cys Lys Ala Ser Gln Asp Val Ser Thr Val
            20                  25                  30

Val Ala Trp Tyr Gln Gln Lys Pro Gly Gln Ser Pro Lys Arg Leu Ile
        35                  40                  45

Tyr Ser Ala Ser Tyr Arg Tyr Ile Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Pro Pro Tyr
                85                  90                  95

Thr Phe Gly Gly Gly Thr Lys Leu Glu Ile Lys Arg
            100                 105


<210> SEQ ID NO 43
<211> LENGTH: 324
<212> TYPE: DNA
<213> ORGANISM: Mus sp.
<220> FEATURE:
<221> NAME/KEY: CDS
<222> LOCATION: (1)..(324)

<400> SEQUENCE: 43

gac att gtg atg acc cag tct cac aaa ttc ttg tcc aca tca gtt gga       48
Asp Ile Val Met Thr Gln Ser His Lys Phe Leu Ser Thr Ser Val Gly
1               5                   10                  15

gac agg gtc agt atc acc tgc aag gcc agt cag gat gtg gtt act gct       96
Asp Arg Val Ser Ile Thr Cys Lys Ala Ser Gln Asp Val Val Thr Ala
            20                  25                  30

gtt gcc tgg ttt caa cag aaa cca gga caa tct cca aaa cta ctg att      144
Val Ala Trp Phe Gln Gln Lys Pro Gly Gln Ser Pro Lys Leu Leu Ile
        35                  40                  45

tat tcg gca tcc cac cgg tac act gga gtc cct gat cgc ttc act ggc      192
Tyr Ser Ala Ser His Arg Tyr Thr Gly Val Pro Asp Arg Phe Thr Gly
    50                  55                  60
```

```
agt gga tct ggg aca gat ttc act ttc acc atc atc agt gtg cag gct      240
Ser Gly Ser Gly Thr Asp Phe Thr Phe Thr Ile Ile Ser Val Gln Ala
65                  70                  75                  80

gaa gac ctg gca gtt tat tac tgt caa caa cat tat act act ccc acg      288
Glu Asp Leu Ala Val Tyr Tyr Cys Gln Gln His Tyr Thr Thr Pro Thr
                85                  90                  95

acg ttc ggt gga ggc acc aag ctg gac ttc aga cgg                      324
Thr Phe Gly Gly Gly Thr Lys Leu Asp Phe Arg Arg
            100                 105


<210> SEQ ID NO 44
<211> LENGTH: 108
<212> TYPE: PRT
<213> ORGANISM: Mus sp.

<400> SEQUENCE: 44

Asp Ile Val Met Thr Gln Ser His Lys Phe Leu Ser Thr Ser Val Gly
1               5                   10                  15

Asp Arg Val Ser Ile Thr Cys Lys Ala Ser Gln Asp Val Val Thr Ala
            20                  25                  30

Val Ala Trp Phe Gln Gln Lys Pro Gly Gln Ser Pro Lys Leu Leu Ile
        35                  40                  45

Tyr Ser Ala Ser His Arg Tyr Thr Gly Val Pro Asp Arg Phe Thr Gly
    50                  55                  60

Ser Gly Ser Gly Thr Asp Phe Thr Phe Thr Ile Ile Ser Val Gln Ala
65                  70                  75                  80

Glu Asp Leu Ala Val Tyr Tyr Cys Gln Gln His Tyr Thr Thr Pro Thr
                85                  90                  95

Thr Phe Gly Gly Gly Thr Lys Leu Asp Phe Arg Arg
            100                 105


<210> SEQ ID NO 45
<211> LENGTH: 324
<212> TYPE: DNA
<213> ORGANISM: Mus sp.
<220> FEATURE:
<221> NAME/KEY: CDS
<222> LOCATION: (1)..(324)

<400> SEQUENCE: 45

gac act gtg atg acc cag tct cac aaa ttc ata tcc aca tca gtt gga       48
Asp Thr Val Met Thr Gln Ser His Lys Phe Ile Ser Thr Ser Val Gly
1               5                   10                  15

gac agg gtc agc atc acc tgc aag gcc agt cag gtt gtg ggt agt gct       96
Asp Arg Val Ser Ile Thr Cys Lys Ala Ser Gln Val Val Gly Ser Ala
            20                  25                  30

gta gcc tgg tat caa cag aaa cca ggg caa tct cct aaa cta ctg att      144
Val Ala Trp Tyr Gln Gln Lys Pro Gly Gln Ser Pro Lys Leu Leu Ile
        35                  40                  45

tac tgg gca tcc acc cgg cac act gga gtc cct gat cgc ttc aca ggc      192
Tyr Trp Ala Ser Thr Arg His Thr Gly Val Pro Asp Arg Phe Thr Gly
    50                  55                  60

agt gga tct ggg aca gat ttc act ctc acc att agc aat gtg cag tct      240
Ser Gly Ser Gly Thr Asp Phe Thr Leu Thr Ile Ser Asn Val Gln Ser
65                  70                  75                  80

gaa gac ttg gca gat tat ttc tgt cag caa tat aac agc tat ccg tac      288
Glu Asp Leu Ala Asp Tyr Phe Cys Gln Gln Tyr Asn Ser Tyr Pro Tyr
                85                  90                  95

acg ttc gga ggg ggg acc aag ctg gaa ata aaa cgg                      324
Thr Phe Gly Gly Gly Thr Lys Leu Glu Ile Lys Arg
            100                 105
```

<210> SEQ ID NO 46
<211> LENGTH: 108
<212> TYPE: PRT
<213> ORGANISM: Mus sp.

<400> SEQUENCE: 46

```
Asp Thr Val Met Thr Gln Ser His Lys Phe Ile Ser Thr Ser Val Gly
1               5                   10                  15

Asp Arg Val Ser Ile Thr Cys Lys Ala Ser Gln Val Val Gly Ser Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Asn Ser Tyr Pro Tyr
                85                  90                  95

Thr Phe Gly Gly Gly Thr Lys Leu Glu Ile Lys Arg
            100                 105
```

<210> SEQ ID NO 47
<211> LENGTH: 324
<212> TYPE: DNA
<213> ORGANISM: Mus sp.
<220> FEATURE:
<221> NAME/KEY: CDS
<222> LOCATION: (1)..(324)

<400> SEQUENCE: 47

```
gac att gtg atg acc cag tct caa aaa ttc atg tcc aca tca gta gga       48
Asp Ile Val Met Thr Gln Ser Gln Lys Phe Met Ser Thr Ser Val Gly
1               5                   10                  15

gac agg gtc agc gtc acc tgc aag gcc agt cag aat gtg ggt act aat       96
Asp Arg Val Ser Val Thr Cys Lys Ala Ser Gln Asn Val Gly Thr Asn
            20                  25                  30

gtt gcc tgg tat caa cac aaa cca gga caa tcc cct aaa ata atg att      144
Val Ala Trp Tyr Gln His Lys Pro Gly Gln Ser Pro Lys Ile Met Ile
        35                  40                  45

tat tcg gcg tcc tcc cgg tac agt gga gtc cct gat cgc ttc aca ggc      192
Tyr Ser Ala Ser Ser Arg Tyr Ser Gly Val Pro Asp Arg Phe Thr Gly
    50                  55                  60

agt gga tct ggg aca ctt ttc act ctc acc atc aac aat gtg cag tct      240
Ser Gly Ser Gly Thr Leu Phe Thr Leu Thr Ile Asn Asn Val Gln Ser
65                  70                  75                  80

gaa gac ttg gca gag tat ttc tgt cag caa tat aac agc tat cct ctc      288
Glu Asp Leu Ala Glu Tyr Phe Cys Gln Gln Tyr Asn Ser Tyr Pro Leu
                85                  90                  95

acg ttc ggc tcg ggg aca aag ttg gaa ata aaa cgg                      324
Thr Phe Gly Ser Gly Thr Lys Leu Glu Ile Lys Arg
            100                 105
```

<210> SEQ ID NO 48
<211> LENGTH: 108
<212> TYPE: PRT
<213> ORGANISM: Mus sp.

<400> SEQUENCE: 48

```
Asp Ile Val Met Thr Gln Ser Gln Lys Phe Met Ser Thr Ser Val Gly
1               5                   10                  15
```

```
Asp Arg Val Ser Val Thr Cys Lys Ala Ser Gln Asn Val Gly Thr Asn
            20                  25                  30

Val Ala Trp Tyr Gln His Lys Pro Gly Gln Ser Pro Lys Ile Met Ile
        35                  40                  45

Tyr Ser Ala Ser Ser Arg Tyr Ser Gly Val Pro Asp Arg Phe Thr Gly
    50                  55                  60

Ser Gly Ser Gly Thr Leu Phe Thr Leu Thr Ile Asn Asn Val Gln Ser
65                  70                  75                  80

Glu Asp Leu Ala Glu Tyr Phe Cys Gln Gln Tyr Asn Ser Tyr Pro Leu
                85                  90                  95

Thr Phe Gly Ser Gly Thr Lys Leu Glu Ile Lys Arg
            100                 105


<210> SEQ ID NO 49
<211> LENGTH: 342
<212> TYPE: DNA
<213> ORGANISM: Mus sp.
<220> FEATURE:
<221> NAME/KEY: CDS
<222> LOCATION: (1)..(342)

<400> SEQUENCE: 49

cag atc cag ttg gtg cag tct gga cct gag ctg aag aag cct gga gag       48
Gln Ile Gln Leu Val Gln Ser Gly Pro Glu Leu Lys Lys Pro Gly Glu
1               5                   10                  15

aca gtc aag atc tcc tgc aag gct tct ggg tat acc ctc aca agc tac       96
Thr Val Lys Ile Ser Cys Lys Ala Ser Gly Tyr Thr Leu Thr Ser Tyr
            20                  25                  30

gga atg aac tgg gtg aag cag gct cca gga aag ggt tta aag tgg atg      144
Gly Met Asn Trp Val Lys Gln Ala Pro Gly Lys Gly Leu Lys Trp Met
        35                  40                  45

ggc tgg ata aac acc tac act gga gaa cca aca tat gct gat gac ttt      192
Gly Trp Ile Asn Thr Tyr Thr Gly Glu Pro Thr Tyr Ala Asp Asp Phe
    50                  55                  60

aag gga cgt ttt gcc ttc tct ttg gaa acc tct gcc agc act gcc ttt      240
Lys Gly Arg Phe Ala Phe Ser Leu Glu Thr Ser Ala Ser Thr Ala Phe
65                  70                  75                  80

ttg cag atc aac aac ctc aaa aat gag gac acg gct aca tat ttc tgt      288
Leu Gln Ile Asn Asn Leu Lys Asn Glu Asp Thr Ala Thr Tyr Phe Cys
                85                  90                  95

gta aga cgc ggg ttt gct tac tgg ggc caa ggg act ctg gtc act gtc      336
Val Arg Arg Gly Phe Ala Tyr Trp Gly Gln Gly Thr Leu Val Thr Val
            100                 105                 110

tct gca                                                              342
Ser Ala


<210> SEQ ID NO 50
<211> LENGTH: 114
<212> TYPE: PRT
<213> ORGANISM: Mus sp.

<400> SEQUENCE: 50

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Leu Thr Ser Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
```

```
    50                  55                  60

Lys Gly Arg Phe Ala Phe Ser Leu Glu Thr Ser Ala Ser Thr Ala Phe
65                  70                  75                  80

Leu Gln Ile Asn Asn Leu Lys Asn Glu Asp Thr Ala Thr Tyr Phe Cys
                85                  90                  95

Val Arg Arg Gly Phe Ala Tyr Trp Gly Gln Gly Thr Leu Val Thr Val
            100                 105                 110

Ser Ala


<210> SEQ ID NO 51
<211> LENGTH: 342
<212> TYPE: DNA
<213> ORGANISM: Mus sp.
<220> FEATURE:
<221> NAME/KEY: CDS
<222> LOCATION: (1)..(342)

<400> SEQUENCE: 51

cag atc cag ttg gtg cag tct gga cct gag ctg aag aag cct gga gag       48
Gln Ile Gln Leu Val Gln Ser Gly Pro Glu Leu Lys Lys Pro Gly Glu
1               5                   10                  15

aca gtc aag atc tcc tgc aag gct tct ggg tat acc ttc aca aac tct       96
Thr Val Lys Ile Ser Cys Lys Ala Ser Gly Tyr Thr Phe Thr Asn Ser
            20                  25                  30

gga atg aac tgg gtg aag cag gct cca gga aag ggt tta aag tgg atg      144
Gly Met Asn Trp Val Lys Gln Ala Pro Gly Lys Gly Leu Lys Trp Met
        35                  40                  45

ggc tgg ata aac acc tac act gga gag ccg aca tat gct gat gac ttc      192
Gly Trp Ile Asn Thr Tyr Thr Gly Glu Pro Thr Tyr Ala Asp Asp Phe
    50                  55                  60

aag gga cgg ttt gcc ttc tct ttg gaa acc tct gcc agc tct gcc tat      240
Lys Gly Arg Phe Ala Phe Ser Leu Glu Thr Ser Ala Ser Ser Ala Tyr
65                  70                  75                  80

ttg cag atc agt aac ctc aaa aat gag gac acg gct aca tat ttc tgt      288
Leu Gln Ile Ser Asn Leu Lys Asn Glu Asp Thr Ala Thr Tyr Phe Cys
                85                  90                  95

gca aga agg ggt ttt gtt tac tgg ggc caa ggg act ctg gta act gtc      336
Ala Arg Arg Gly Phe Val Tyr Trp Gly Gln Gly Thr Leu Val Thr Val
            100                 105                 110

tct gca                                                              342
Ser Ala


<210> SEQ ID NO 52
<211> LENGTH: 114
<212> TYPE: PRT
<213> ORGANISM: Mus sp.

<400> SEQUENCE: 52

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Ser
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Ser Ala Tyr
65                  70                  75                  80

Leu Gln Ile Ser Asn Leu Lys Asn Glu Asp Thr Ala Thr Tyr Phe Cys
```

-continued

```
                85                  90                  95

Ala Arg Arg Gly Phe Val Tyr Trp Gly Gln Gly Thr Leu Val Thr Val
            100                 105                 110

Ser Ala


<210> SEQ ID NO 53
<211> LENGTH: 360
<212> TYPE: DNA
<213> ORGANISM: Mus sp.
<220> FEATURE:
<221> NAME/KEY: CDS
<222> LOCATION: (1)..(360)

<400> SEQUENCE: 53

cag gtt cag ctc cag cag tct ggg gct gag ctg gca aga cct ggg act       48
Gln Val Gln Leu Gln Gln Ser Gly Ala Glu Leu Ala Arg Pro Gly Thr
1               5                   10                  15

tca gtg aag ttg tcc tgt aag gct tct ggc tac acc ttt act gac tac       96
Ser Val Lys Leu Ser Cys Lys Ala Ser Gly Tyr Thr Phe Thr Asp Tyr
            20                  25                  30

tgg atg cag tgg gta aaa cag agg cct gga cag ggt ctg gag tgg att      144
Trp Met Gln Trp Val Lys Gln Arg Pro Gly Gln Gly Leu Glu Trp Ile
        35                  40                  45

ggg act att tat cct gga gat ggt gat act ggg tac gct cag aag ttc      192
Gly Thr Ile Tyr Pro Gly Asp Gly Asp Thr Gly Tyr Ala Gln Lys Phe
    50                  55                  60

aag ggc aag gcc aca ttg act gcg gat aaa tcc tcc aaa aca gtc tac      240
Lys Gly Lys Ala Thr Leu Thr Ala Asp Lys Ser Ser Lys Thr Val Tyr
65                  70                  75                  80

atg cac ctc agc agt ttg gct tct gag gac tct gcg gtc tat tac tgt      288
Met His Leu Ser Ser Leu Ala Ser Glu Asp Ser Ala Val Tyr Tyr Cys
                85                  90                  95

gca aga ggg gat tac tac ggt agt aat tct ttg gac tat tgg ggt caa      336
Ala Arg Gly Asp Tyr Tyr Gly Ser Asn Ser Leu Asp Tyr Trp Gly Gln
            100                 105                 110

gga acc tca gtc acc gtc tcc tca                                      360
Gly Thr Ser Val Thr Val Ser Ser
        115                 120


<210> SEQ ID NO 54
<211> LENGTH: 120
<212> TYPE: PRT
<213> ORGANISM: Mus sp.

<400> SEQUENCE: 54

Gln Val Gln Leu Gln Gln Ser Gly Ala Glu Leu Ala Arg Pro Gly Thr
1               5                   10                  15

Ser Val Lys Leu Ser Cys Lys Ala Ser Gly Tyr Thr Phe Thr Asp Tyr
            20                  25                  30

Trp Met Gln Trp Val Lys Gln Arg Pro Gly Gln Gly Leu Glu Trp Ile
        35                  40                  45

Gly Thr Ile Tyr Pro Gly Asp Gly Asp Thr Gly Tyr Ala Gln Lys Phe
    50                  55                  60

Lys Gly Lys Ala Thr Leu Thr Ala Asp Lys Ser Ser Lys Thr Val Tyr
65                  70                  75                  80

Met His Leu Ser Ser Leu Ala Ser Glu Asp Ser Ala Val Tyr Tyr Cys
                85                  90                  95

Ala Arg Gly Asp Tyr Tyr Gly Ser Asn Ser Leu Asp Tyr Trp Gly Gln
            100                 105                 110
```

```
Gly Thr Ser Val Thr Val Ser Ser
        115                 120


<210> SEQ ID NO 55
<211> LENGTH: 357
<212> TYPE: DNA
<213> ORGANISM: Mus sp.
<220> FEATURE:
<221> NAME/KEY: CDS
<222> LOCATION: (1)..(357)

<400> SEQUENCE: 55

cag gtc cag tta cag caa tct gga cct gaa ctg gtg agg cct ggg gcc       48
Gln Val Gln Leu Gln Gln Ser Gly Pro Glu Leu Val Arg Pro Gly Ala
1               5                   10                  15

tca gtg aag att tcc tgc aaa act tct ggc tac gca ttc agt ggc tcc       96
Ser Val Lys Ile Ser Cys Lys Thr Ser Gly Tyr Ala Phe Ser Gly Ser
            20                  25                  30

tgg atg aac tgg gtg aag cag agg cct gga cag ggt cta gag tgg att      144
Trp Met Asn Trp Val Lys Gln Arg Pro Gly Gln Gly Leu Glu Trp Ile
        35                  40                  45

gga cgg att tat ccg gga gat gga gat atc att tac aat ggg aat ttc      192
Gly Arg Ile Tyr Pro Gly Asp Gly Asp Ile Ile Tyr Asn Gly Asn Phe
    50                  55                  60

agg gac aag gtc aca ctg tct gca gac aaa tcc tcc aac aca gcc tac      240
Arg Asp Lys Val Thr Leu Ser Ala Asp Lys Ser Ser Asn Thr Ala Tyr
65                  70                  75                  80

atg cag ctc agc agc ctg acc tct gtg gac tct gcg gtc tat ttt tgt      288
Met Gln Leu Ser Ser Leu Thr Ser Val Asp Ser Ala Val Tyr Phe Cys
                85                  90                  95

tcg aga tgg ggg aca ttt acg ccg agt ttt gac tat tgg ggc caa ggc      336
Ser Arg Trp Gly Thr Phe Thr Pro Ser Phe Asp Tyr Trp Gly Gln Gly
            100                 105                 110

acc act ctc aca gtc tcc tca                                          357
Thr Thr Leu Thr Val Ser Ser
        115


<210> SEQ ID NO 56
<211> LENGTH: 119
<212> TYPE: PRT
<213> ORGANISM: Mus sp.

<400> SEQUENCE: 56

Gln Val Gln Leu Gln Gln Ser Gly Pro Glu Leu Val Arg Pro Gly Ala
1               5                   10                  15

Ser Val Lys Ile Ser Cys Lys Thr Ser Gly Tyr Ala Phe Ser Gly Ser
            20                  25                  30

Trp Met Asn Trp Val Lys Gln Arg Pro Gly Gln Gly Leu Glu Trp Ile
        35                  40                  45

Gly Arg Ile Tyr Pro Gly Asp Gly Asp Ile Ile Tyr Asn Gly Asn Phe
    50                  55                  60

Arg Asp Lys Val Thr Leu Ser Ala Asp Lys Ser Ser Asn Thr Ala Tyr
65                  70                  75                  80

Met Gln Leu Ser Ser Leu Thr Ser Val Asp Ser Ala Val Tyr Phe Cys
                85                  90                  95

Ser Arg Trp Gly Thr Phe Thr Pro Ser Phe Asp Tyr Trp Gly Gln Gly
            100                 105                 110

Thr Thr Leu Thr Val Ser Ser
        115
```

<210> SEQ ID NO 57
<211> LENGTH: 351
<212> TYPE: DNA
<213> ORGANISM: Mus sp.
<220> FEATURE:
<221> NAME/KEY: CDS
<222> LOCATION: (1)..(351)

<400> SEQUENCE: 57

```
gac gtg aag ctg gtg gag tct ggg gga ggc tta gtg aag cct gga ggg       48
Asp Val Lys Leu Val Glu Ser Gly Gly Gly Leu Val Lys Pro Gly Gly
1               5                   10                  15

tcc ctg aaa ctc tcc tgt gaa gcc tct gga ttc act ttc agt agc tat       96
Ser Leu Lys Leu Ser Cys Glu Ala Ser Gly Phe Thr Phe Ser Ser Tyr
            20                  25                  30

acc ctg tct tgg gtt cgc cag act ccg gag acg agg ctg gag tgg gtc      144
Thr Leu Ser Trp Val Arg Gln Thr Pro Glu Thr Arg Leu Glu Trp Val
        35                  40                  45

gca acc att agt att ggt ggt cgc tac acc tat tat cca gac agt gtg      192
Ala Thr Ile Ser Ile Gly Gly Arg Tyr Thr Tyr Tyr Pro Asp Ser Val
    50                  55                  60

gag ggc cga ttc acc atc tcc aga gac aat gcc aag aac acc ctg tac      240
Glu Gly Arg Phe Thr Ile Ser Arg Asp Asn Ala Lys Asn Thr Leu Tyr
65                  70                  75                  80

ctg caa atg aac agt ctg aag tct gag gac aca gcc atg tat tac tgt      288
Leu Gln Met Asn Ser Leu Lys Ser Glu Asp Thr Ala Met Tyr Tyr Cys
                85                  90                  95

aca aga gat ttt aat ggt tac tct gac ttc tgg ggc caa ggc acc act      336
Thr Arg Asp Phe Asn Gly Tyr Ser Asp Phe Trp Gly Gln Gly Thr Thr
            100                 105                 110

ctc aca gtc tcc tca                                                  351
Leu Thr Val Ser Ser
        115
```

<210> SEQ ID NO 58
<211> LENGTH: 117
<212> TYPE: PRT
<213> ORGANISM: Mus sp.

<400> SEQUENCE: 58

```
Asp Val Lys Leu Val Glu Ser Gly Gly Gly Leu Val Lys Pro Gly Gly
1               5                   10                  15

Ser Leu Lys Leu Ser Cys Glu Ala Ser Gly Phe Thr Phe Ser Ser Tyr
            20                  25                  30

Thr Leu Ser Trp Val Arg Gln Thr Pro Glu Thr Arg Leu Glu Trp Val
        35                  40                  45

Ala Thr Ile Ser Ile Gly Gly Arg Tyr Thr Tyr Tyr Pro Asp Ser Val
    50                  55                  60

Glu Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Met Tyr Tyr Cys
                85                  90                  95

Thr Arg Asp Phe Asn Gly Tyr Ser Asp Phe Trp Gly Gln Gly Thr Thr
            100                 105                 110

Leu Thr Val Ser Ser
        115
```

<210> SEQ ID NO 59
<211> LENGTH: 360
<212> TYPE: DNA
<213> ORGANISM: Mus sp.

<220> FEATURE:
<221> NAME/KEY: CDS
<222> LOCATION: (1)..(360)

<400> SEQUENCE: 59

```
aat gta cag ctg gta gag tct ggg gga ggc tta gtg cag cct gga ggg       48
Asn Val Gln Leu Val Glu Ser Gly Gly Gly Leu Val Gln Pro Gly Gly
1               5                   10                  15

tcc cgg aaa ctc tcc tgt gca gcc tct gga ttc act ttc agt aac ttt       96
Ser Arg Lys Leu Ser Cys Ala Ala Ser Gly Phe Thr Phe Ser Asn Phe
            20                  25                  30

gga atg cac tgg gtt cgt cag gct cca gag aag ggt ctg gag tgg gtc      144
Gly Met His Trp Val Arg Gln Ala Pro Glu Lys Gly Leu Glu Trp Val
        35                  40                  45

gca tac att cgt agt ggc agt ggt acc atc tac tat tca gac aca gtg      192
Ala Tyr Ile Arg Ser Gly Ser Gly Thr Ile Tyr Tyr Ser Asp Thr Val
    50                  55                  60

aag ggc cga ttc acc atc tcc aga gac aat ccc aag aac acc ctg ttc      240
Lys Gly Arg Phe Thr Ile Ser Arg Asp Asn Pro Lys Asn Thr Leu Phe
65                  70                  75                  80

ctg caa atg acc agt cta agg tct gag gac acg gcc atg tat tac tgt      288
Leu Gln Met Thr Ser Leu Arg Ser Glu Asp Thr Ala Met Tyr Tyr Cys
                85                  90                  95

gca aga tcc tac tat gat ttc ggg gcc tgg ttt gct tac tgg ggc caa      336
Ala Arg Ser Tyr Tyr Asp Phe Gly Ala Trp Phe Ala Tyr Trp Gly Gln
            100                 105                 110

ggg act ctg gtc act gtc tct gca                                      360
Gly Thr Leu Val Thr Val Ser Ala
        115                 120
```

<210> SEQ ID NO 60
<211> LENGTH: 120
<212> TYPE: PRT
<213> ORGANISM: Mus sp.

<400> SEQUENCE: 60

```
Asn Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Asn Phe
            20                  25                  30

Gly Met His Trp Val Arg Gln Ala Pro Glu Lys Gly Leu Glu Trp Val
        35                  40                  45

Ala Tyr Ile Arg Ser Gly Ser Gly Thr Ile Tyr Tyr Ser Asp Thr Val
    50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Ser Tyr Tyr Asp Phe Gly Ala Trp Phe Ala Tyr Trp Gly Gln
            100                 105                 110

Gly Thr Leu Val Thr Val Ser Ala
        115                 120
```

<210> SEQ ID NO 61
<211> LENGTH: 324
<212> TYPE: DNA
<213> ORGANISM: Homo sapiens
<220> FEATURE:
<221> NAME/KEY: CDS
<222> LOCATION: (1)..(324)

<400> SEQUENCE: 61

```
gat atc gta atg acc cag tcc cac ctg agt atg agt acc tcc ctg gga       48
Asp Ile Val Met Thr Gln Ser His Leu Ser Met Ser Thr Ser Leu Gly
1               5                   10                  15

gat cct gtg tca atc act tgc aag gcc tca cag gat gtg agc acc gtc       96
Asp Pro Val Ser Ile Thr Cys Lys Ala Ser Gln Asp Val Ser Thr Val
            20                  25                  30

gtt gct tgg tat cag cag aag ccc ggg caa tca ccc aga cgt ctc atc      144
Val Ala Trp Tyr Gln Gln Lys Pro Gly Gln Ser Pro Arg Arg Leu Ile
        35                  40                  45

tac tca gca tca tac cgt tac atc ggg gtg cct gac cga ttt act ggc      192
Tyr Ser Ala Ser Tyr Arg Tyr Ile Gly Val Pro Asp Arg Phe Thr Gly
    50                  55                  60

tct ggc gct ggc aca gat ttc acc ttt aca att agt tcc gtc cag gcc      240
Ser Gly Ala Gly Thr Asp Phe Thr Phe Thr Ile Ser Ser Val Gln Ala
65                  70                  75                  80

gaa gac ctg gcc gtg tac tac tgc cag cag cac tac agt ccc cca tac      288
Glu Asp Leu Ala Val Tyr Tyr Cys Gln Gln His Tyr Ser Pro Pro Tyr
                85                  90                  95

act ttc ggg gga ggg act aag ctc gaa atc aaa cgt                      324
Thr Phe Gly Gly Gly Thr Lys Leu Glu Ile Lys Arg
            100                 105
```

<210> SEQ ID NO 62
<211> LENGTH: 108
<212> TYPE: PRT
<213> ORGANISM: Homo sapiens

<400> SEQUENCE: 62

```
Asp Ile Val Met Thr Gln Ser His Leu Ser Met Ser Thr Ser Leu Gly
1               5                   10                  15

Asp Pro Val Ser Ile Thr Cys Lys Ala Ser Gln Asp Val Ser Thr Val
            20                  25                  30

Val Ala Trp Tyr Gln Gln Lys Pro Gly Gln Ser Pro Arg Arg Leu Ile
        35                  40                  45

Tyr Ser Ala Ser Tyr Arg Tyr Ile Gly Val Pro Asp Arg Phe Thr Gly
    50                  55                  60

Ser Gly Ala Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Pro Pro Tyr
                85                  90                  95

Thr Phe Gly Gly Gly Thr Lys Leu Glu Ile Lys Arg
            100                 105
```

<210> SEQ ID NO 63
<211> LENGTH: 324
<212> TYPE: DNA
<213> ORGANISM: Homo sapiens
<220> FEATURE:
<221> NAME/KEY: CDS
<222> LOCATION: (1)..(324)

<400> SEQUENCE: 63

```
gac att gtt atg gct caa agc cat ctg tct atg agc aca tct ctg gga       48
Asp Ile Val Met Ala Gln Ser His Leu Ser Met Ser Thr Ser Leu Gly
1               5                   10                  15

gat cct gtg tcc atc act tgc aaa gcc agt caa gac gtg tct aca gtt       96
Asp Pro Val Ser Ile Thr Cys Lys Ala Ser Gln Asp Val Ser Thr Val
            20                  25                  30

gtt gca tgg tat caa cag aag cca ggc cag tca ccc aga cgg ctc att      144
```

```
Val Ala Trp Tyr Gln Gln Lys Pro Gly Gln Ser Pro Arg Arg Leu Ile
        35                  40                  45

tac tca gct tct tac cga tac atc ggg gtc cct gac aga ttt aca ggt      192
Tyr Ser Ala Ser Tyr Arg Tyr Ile Gly Val Pro Asp Arg Phe Thr Gly
    50                  55                  60

agt ggg gcc ggt act gac ttc act ttt act atc tca tcc gta caa gcc      240
Ser Gly Ala Gly Thr Asp Phe Thr Phe Thr Ile Ser Ser Val Gln Ala
65                  70                  75                  80

gaa gac ctg gca gta tat tac tgc cag caa cat tat tcc cca ccc tac      288
Glu Asp Leu Ala Val Tyr Tyr Cys Gln Gln His Tyr Ser Pro Pro Tyr
                85                  90                  95

aca ttc ggc ggg ggt act aag ctg gaa att aaa cgt                      324
Thr Phe Gly Gly Gly Thr Lys Leu Glu Ile Lys Arg
            100                 105


<210> SEQ ID NO 64
<211> LENGTH: 108
<212> TYPE: PRT
<213> ORGANISM: Homo sapiens

<400> SEQUENCE: 64

Asp Ile Val Met Ala Gln Ser His Leu Ser Met Ser Thr Ser Leu Gly
1               5                   10                  15

Asp Pro Val Ser Ile Thr Cys Lys Ala Ser Gln Asp Val Ser Thr Val
            20                  25                  30

Val Ala Trp Tyr Gln Gln Lys Pro Gly Gln Ser Pro Arg Arg Leu Ile
        35                  40                  45

Tyr Ser Ala Ser Tyr Arg Tyr Ile Gly Val Pro Asp Arg Phe Thr Gly
    50                  55                  60

Ser Gly Ala Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Pro Pro Tyr
                85                  90                  95

Thr Phe Gly Gly Gly Thr Lys Leu Glu Ile Lys Arg
            100                 105


<210> SEQ ID NO 65
<211> LENGTH: 360
<212> TYPE: DNA
<213> ORGANISM: Homo sapiens
<220> FEATURE:
<221> NAME/KEY: CDS
<222> LOCATION: (1)..(360)

<400> SEQUENCE: 65

cag gta cag ctc gtt cag tcc ggc gcc gag gta gct aag cct ggt act       48
Gln Val Gln Leu Val Gln Ser Gly Ala Glu Val Ala Lys Pro Gly Thr
1               5                   10                  15

tcc gta aaa ttg tcc tgt aag gct tcc ggg tac aca ttt aca gac tac       96
Ser Val Lys Leu Ser Cys Lys Ala Ser Gly Tyr Thr Phe Thr Asp Tyr
            20                  25                  30

tgg atg cag tgg gta aaa cag cgg cca ggt cag ggc ctg gag tgg att      144
Trp Met Gln Trp Val Lys Gln Arg Pro Gly Gln Gly Leu Glu Trp Ile
        35                  40                  45

gga aca ata tat ccc ggc gac ggc gac aca ggc tat gcc cag aag ttt      192
Gly Thr Ile Tyr Pro Gly Asp Gly Asp Thr Gly Tyr Ala Gln Lys Phe
    50                  55                  60

caa ggc aag gca acc ctt act gct gat aaa tct tcc aag act gtc tac      240
Gln Gly Lys Ala Thr Leu Thr Ala Asp Lys Ser Ser Lys Thr Val Tyr
65                  70                  75                  80
```

-continued

```
atg cat ctg tct tcc ttg gca tct gag gat agc gct gtc tat tac tgt      288
Met His Leu Ser Ser Leu Ala Ser Glu Asp Ser Ala Val Tyr Tyr Cys
                85                  90                  95

gct agg ggg gac tac tat ggg tca aat tcc ctg gat tac tgg ggc cag      336
Ala Arg Gly Asp Tyr Tyr Gly Ser Asn Ser Leu Asp Tyr Trp Gly Gln
            100                 105                 110

ggc acc agt gtc acc gtg agc agc                                      360
Gly Thr Ser Val Thr Val Ser Ser
        115                 120


<210> SEQ ID NO 66
<211> LENGTH: 120
<212> TYPE: PRT
<213> ORGANISM: Homo sapiens

<400> SEQUENCE: 66

Gln Val Gln Leu Val Gln Ser Gly Ala Glu Val Ala Lys Pro Gly Thr
1               5                   10                  15

Ser Val Lys Leu Ser Cys Lys Ala Ser Gly Tyr Thr Phe Thr Asp Tyr
            20                  25                  30

Trp Met Gln Trp Val Lys Gln Arg Pro Gly Gln Gly Leu Glu Trp Ile
        35                  40                  45

Gly Thr Ile Tyr Pro Gly Asp Gly Asp Thr Gly Tyr Ala Gln Lys Phe
    50                  55                  60

Gln Gly Lys Ala Thr Leu Thr Ala Asp Lys Ser Ser Lys Thr Val Tyr
65                  70                  75                  80

Met His Leu Ser Ser Leu Ala Ser Glu Asp Ser Ala Val Tyr Tyr Cys
                85                  90                  95

Ala Arg Gly Asp Tyr Tyr Gly Ser Asn Ser Leu Asp Tyr Trp Gly Gln
            100                 105                 110

Gly Thr Ser Val Thr Val Ser Ser
        115                 120


<210> SEQ ID NO 67
<211> LENGTH: 324
<212> TYPE: DNA
<213> ORGANISM: Homo sapiens
<220> FEATURE:
<221> NAME/KEY: CDS
<222> LOCATION: (1)..(324)

<400> SEQUENCE: 67

gac acc gtg atg acc cag tcc ccc tcc acc atc tcc acc tct gtg ggc       48
Asp Thr Val Met Thr Gln Ser Pro Ser Thr Ile Ser Thr Ser Val Gly
1               5                   10                  15

gac cgg gtg tcc atc acc tgt aag gcc tcc cag gtg gtg ggc tcc gcc       96
Asp Arg Val Ser Ile Thr Cys Lys Ala Ser Gln Val Val Gly Ser Ala
            20                  25                  30

gtg gcc tgg tat cag cag aag cct ggc cag tcc cct aag ctg ctg atc      144
Val Ala Trp Tyr Gln Gln Lys Pro Gly Gln Ser Pro Lys Leu Leu Ile
        35                  40                  45

tac tgg gcc tcc acc cgg cat acc ggc gtg cct gac cgg ttc acc ggc      192
Tyr Trp Ala Ser Thr Arg His Thr Gly Val Pro Asp Arg Phe Thr Gly
    50                  55                  60

tcc ggc agc ggc acc gac ttc acc ctg acc atc tcc aac gtg cag tcc      240
Ser Gly Ser Gly Thr Asp Phe Thr Leu Thr Ile Ser Asn Val Gln Ser
65                  70                  75                  80

gac gac ctg gcc gac tac ttc tgc cag cag tac aac tcc tac cct tac      288
Asp Asp Leu Ala Asp Tyr Phe Cys Gln Gln Tyr Asn Ser Tyr Pro Tyr
                85                  90                  95
```

-continued

```
acc ttt ggc ggc gga aca aag ctg gag atc aag cgt                      324
Thr Phe Gly Gly Gly Thr Lys Leu Glu Ile Lys Arg
            100                 105


<210> SEQ ID NO 68
<211> LENGTH: 108
<212> TYPE: PRT
<213> ORGANISM: Homo sapiens

<400> SEQUENCE: 68

Asp Thr Val Met Thr Gln Ser Pro Ser Thr Ile Ser Thr Ser Val Gly
1               5                   10                  15

Asp Arg Val Ser Ile Thr Cys Lys Ala Ser Gln Val Val Gly Ser Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Asp Asp Leu Ala Asp Tyr Phe Cys Gln Gln Tyr Asn Ser Tyr Pro Tyr
                85                  90                  95

Thr Phe Gly Gly Gly Thr Lys Leu Glu Ile Lys Arg
            100                 105


<210> SEQ ID NO 69
<211> LENGTH: 324
<212> TYPE: DNA
<213> ORGANISM: Homo sapiens
<220> FEATURE:
<221> NAME/KEY: CDS
<222> LOCATION: (1)..(324)

<400> SEQUENCE: 69

gac acc gtg atg acc cag tcc ccc tcc tcc atc tcc acc tcc atc ggc       48
Asp Thr Val Met Thr Gln Ser Pro Ser Ser Ile Ser Thr Ser Ile Gly
1               5                   10                  15

gac cgg gtg tcc atc acc tgt aag gcc tcc cag gtg gtg ggc tcc gcc       96
Asp Arg Val Ser Ile Thr Cys Lys Ala Ser Gln Val Val Gly Ser Ala
            20                  25                  30

gtg gcc tgg tat cag cag aag cct ggc cag tcc cct aag ctg ctg atc      144
Val Ala Trp Tyr Gln Gln Lys Pro Gly Gln Ser Pro Lys Leu Leu Ile
        35                  40                  45

tac tgg gcc tcc acc cgg cat acc ggc gtg cct gcc cgg ttc acc ggc      192
Tyr Trp Ala Ser Thr Arg His Thr Gly Val Pro Ala Arg Phe Thr Gly
    50                  55                  60

tcc ggc agc ggc acc gac ttc acc ctg acc atc tcc aac gtg cag tcc      240
Ser Gly Ser Gly Thr Asp Phe Thr Leu Thr Ile Ser Asn Val Gln Ser
65                  70                  75                  80

gag gac ctg gcc gac tac ttc tgc cag cag tac aac tcc tac cct tac      288
Glu Asp Leu Ala Asp Tyr Phe Cys Gln Gln Tyr Asn Ser Tyr Pro Tyr
                85                  90                  95

acc ttt ggc ggc gga aca aag ctg gag atc aag cgt                      324
Thr Phe Gly Gly Gly Thr Lys Leu Glu Ile Lys Arg
            100                 105


<210> SEQ ID NO 70
<211> LENGTH: 108
<212> TYPE: PRT
<213> ORGANISM: Homo sapiens

<400> SEQUENCE: 70
```

```
Asp Thr Val Met Thr Gln Ser Pro Ser Ser Ile Ser Thr Ser Ile Gly
1               5                   10                  15

Asp Arg Val Ser Ile Thr Cys Lys Ala Ser Gln Val Val Gly Ser Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Ala Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Asn Ser Tyr Pro Tyr
                85                  90                  95

Thr Phe Gly Gly Gly Thr Lys Leu Glu Ile Lys Arg
            100                 105


<210> SEQ ID NO 71
<211> LENGTH: 351
<212> TYPE: DNA
<213> ORGANISM: Homo sapiens
<220> FEATURE:
<221> NAME/KEY: CDS
<222> LOCATION: (1)..(351)

<400> SEQUENCE: 71

gag gtg cag ctg gtg gag tct ggc ggc gga ctg gtg aag cct ggc ggc       48
Glu Val Gln Leu Val Glu Ser Gly Gly Gly Leu Val Lys Pro Gly Gly
1               5                   10                  15

tcc ctg agg ctg tcc tgt gag gcc tcc ggc ttc acc ttc tcc tcc tac       96
Ser Leu Arg Leu Ser Cys Glu Ala Ser Gly Phe Thr Phe Ser Ser Tyr
            20                  25                  30

acc ctg tcc tgg gtg agg cag acc cct ggc aag ggc ctg gag tgg gtg      144
Thr Leu Ser Trp Val Arg Gln Thr Pro Gly Lys Gly Leu Glu Trp Val
        35                  40                  45

gcc acc atc tcc atc ggc ggc agg tac acc tac tac cct gac tcc gtg      192
Ala Thr Ile Ser Ile Gly Gly Arg Tyr Thr Tyr Tyr Pro Asp Ser Val
    50                  55                  60

aag ggc cgg ttc acc atc tcc cgg gac aac gcc aag aac acc ctg tac      240
Lys Gly Arg Phe Thr Ile Ser Arg Asp Asn Ala Lys Asn Thr Leu Tyr
65                  70                  75                  80

ctg cag atg aac tcc ctg aag tcc gag gac acc gcc atg tac tac tgt      288
Leu Gln Met Asn Ser Leu Lys Ser Glu Asp Thr Ala Met Tyr Tyr Cys
                85                  90                  95

acc cgg gac ttc aac ggc tac tcc gac ttc tgg ggc cag ggc acc aca      336
Thr Arg Asp Phe Asn Gly Tyr Ser Asp Phe Trp Gly Gln Gly Thr Thr
            100                 105                 110

ctg acc gtg tcc tcc                                                  351
Leu Thr Val Ser Ser
        115


<210> SEQ ID NO 72
<211> LENGTH: 117
<212> TYPE: PRT
<213> ORGANISM: Homo sapiens

<400> SEQUENCE: 72

Glu Val Gln Leu Val Glu Ser Gly Gly Gly Leu Val Lys Pro Gly Gly
1               5                   10                  15

Ser Leu Arg Leu Ser Cys Glu Ala Ser Gly Phe Thr Phe Ser Ser Tyr
            20                  25                  30
```

```
Thr Leu Ser Trp Val Arg Gln Thr Pro Gly Lys Gly Leu Glu Trp Val
        35                  40                  45

Ala Thr Ile Ser Ile Gly Gly Arg Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Met Tyr Tyr Cys
                85                  90                  95

Thr Arg Asp Phe Asn Gly Tyr Ser Asp Phe Trp Gly Gln Gly Thr Thr
            100                 105                 110

Leu Thr Val Ser Ser
        115


<210> SEQ ID NO 73
<211> LENGTH: 36
<212> TYPE: DNA
<213> ORGANISM: Mus sp.

<400> SEQUENCE: 73

ggaggatcca tagacagatg ggggtgtcgt tttggc                              36


<210> SEQ ID NO 74
<211> LENGTH: 32
<212> TYPE: DNA
<213> ORGANISM: Mus sp.

<400> SEQUENCE: 74

ggaggatccc ttgaccaggc atcctagagt ca                                  32


<210> SEQ ID NO 75
<211> LENGTH: 32
<212> TYPE: DNA
<213> ORGANISM: Mus sp.
<220> FEATURE:
<221> NAME/KEY: misc_feature
<222> LOCATION: (1)..(32)
<223> OTHER INFORMATION: mixed bases are defined as follows: H=A+T+C,
      S=G+C, Y=C+T,  K=G+T,  M=A+C,  R=A+G,  W=A+T,  V = A+C+G,
      N = A+C+G+T

<400> SEQUENCE: 75

cttccggaat tcsargtnma gctgsagsag tc                                  32


<210> SEQ ID NO 76
<211> LENGTH: 35
<212> TYPE: DNA
<213> ORGANISM: Mus sp.
<220> FEATURE:
<221> NAME/KEY: misc_feature
<222> LOCATION: (1)..(35)
<223> OTHER INFORMATION: mixed bases are defined as follows: H=A+T+C,
      S=G+C, Y=C+T,  K=G+T,  M=A+C,  R=A+G,  W=A+T,  V = A+C+G, N =
      A+C+G+T

<400> SEQUENCE: 76

cttccggaat tcsargtnma gctgsagsag tcwgg                               35


<210> SEQ ID NO 77
<211> LENGTH: 31
<212> TYPE: DNA
<213> ORGANISM: Mus sp.
<220> FEATURE:
<221> NAME/KEY: misc_feature
<222> LOCATION: (1)..(31)
<223> OTHER INFORMATION: mixed bases are defined as follows: H=A+T+C,
```

-continued

```
      S=G+C, Y=C+T,  K=G+T,  M=A+C,  R=A+G,  W=A+T,  V = A+C+G, N =
      A+C+G+T

<400> SEQUENCE: 77

ggagctcgay attgtgmtsa cmcarwctmc a                                    31


<210> SEQ ID NO 78
<211> LENGTH: 46
<212> TYPE: DNA
<213> ORGANISM: Mus sp.

<400> SEQUENCE: 78

tatagagctc aagcttggat ggtgggaaga tggatacagt tggtgc                    46


<210> SEQ ID NO 79
<211> LENGTH: 21
<212> TYPE: DNA
<213> ORGANISM: Mus sp.

<400> SEQUENCE: 79

atggagtcac agattcaggt c                                               21


<210> SEQ ID NO 80
<211> LENGTH: 32
<212> TYPE: DNA
<213> ORGANISM: Mus sp.

<400> SEQUENCE: 80

ttttgaattc cagtaacttc aggtgtccac tc                                   32


<210> SEQ ID NO 81
<211> LENGTH: 17
<212> TYPE: PRT
<213> ORGANISM: Homo sapiens

<400> SEQUENCE: 81

Thr Ile Tyr Pro Gly Asp Gly Asp Thr Gly Tyr Ala Gln Lys Phe Gln
1               5                   10                  15

Gly
```

COMPOSITIONS COMPRISING ANTI-CD38 ANTIBODIES AND CARFILZOMIB

CROSS-REFERENCE TO RELATED APPLICATIONS

This application is a continuation of U.S. patent application Ser. No. 16/375,693, filed Apr. 4, 2019, which is a continuation of U.S. patent application Ser. No. 15/389,279 , filed Dec. 22, 2016, which is a continuation of U.S. patent application Ser. No. 14/775,641 , which adopts the international filing date of Mar. 13, 2014, and is a National Phase application under 35 U.S.C. § 371 of International Application No. PCT/US2014/025441, filed Mar. 13, 2014, which claims the priority benefit of U.S. Provisional Application No. 61/778,540, filed Mar. 13, 2013, and U.S. Provisional Application No. 61/808,381, filed Apr. 4, 2013, the disclosures of which are herein incorporated by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 183952000703 SEQLIST.TXT, date recorded: May 18, 2021, size: 58 KB).

BACKGROUND OF THE INVENTION

1. Field of the Invention

The field of the present invention relates to anti-CD38 antibodies, carfilzomib, and cancer treatments.

2. Description of the Related Art

Multiple myeloma (MM) is a B cell malignancy. In MM, abnormal plasma cells accumulate in the bone marrow where they interfere with the production of normal cells. Current therapy of MM includes administration of proteasome inhibitors such as bortezomib and carfilzomib, immunomodulatory drugs such as lenalidomide and thalidomide, and chemotherapy such as melphalan and prednisone. While these agents have improved survival in multiple myeloma, invariably resistance becomes problematic and patients succumb from their illness. Multiple myeloma thus remains ultimately fatal, with a median survival of approximately 3 to 5 years only.

CD38 is expressed on malignant plasma cells. CD38 is a 45 kD type II transmembrane glycolprotein with a long C-terminal extracellular domain and a short N-terminal cytoplasmic domain. The CD38 protein is a bifunctional ectoenzyme that can catalyze the conversion of $NAD^+$ into cyclic ADP-ribose (cADPR) and also hydrolyze cADPR into ADP-ribose. CD38 is up-regulated and has been implicated in many hematopoietic malignancies.

Thus, some proposed MM treatments include the administration of anti-CD38 antibodies. See, for example, WO 2012/041800; de Weers et al. (2011) J Immunol 186:1840-1848; and Van der Veer et al. (2011) Haematologica 96(2): 284-290. Unfortunately, like various drugs and chemotherapies, not all antibodies are the same and not all antibodies against the same antigen exhibit the same activities.

There is thus a need for new and efficacious treatments for extending survival and improving outcome of treatments of multiple myeloma, and more generally of blood cancers.

DESCRIPTION OF THE DRAWINGS

Both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description serve to explain the principles of the invention.

This invention is further understood by reference to the drawings wherein.

SUMMARY OF THE INVENTION

Figure 1A:
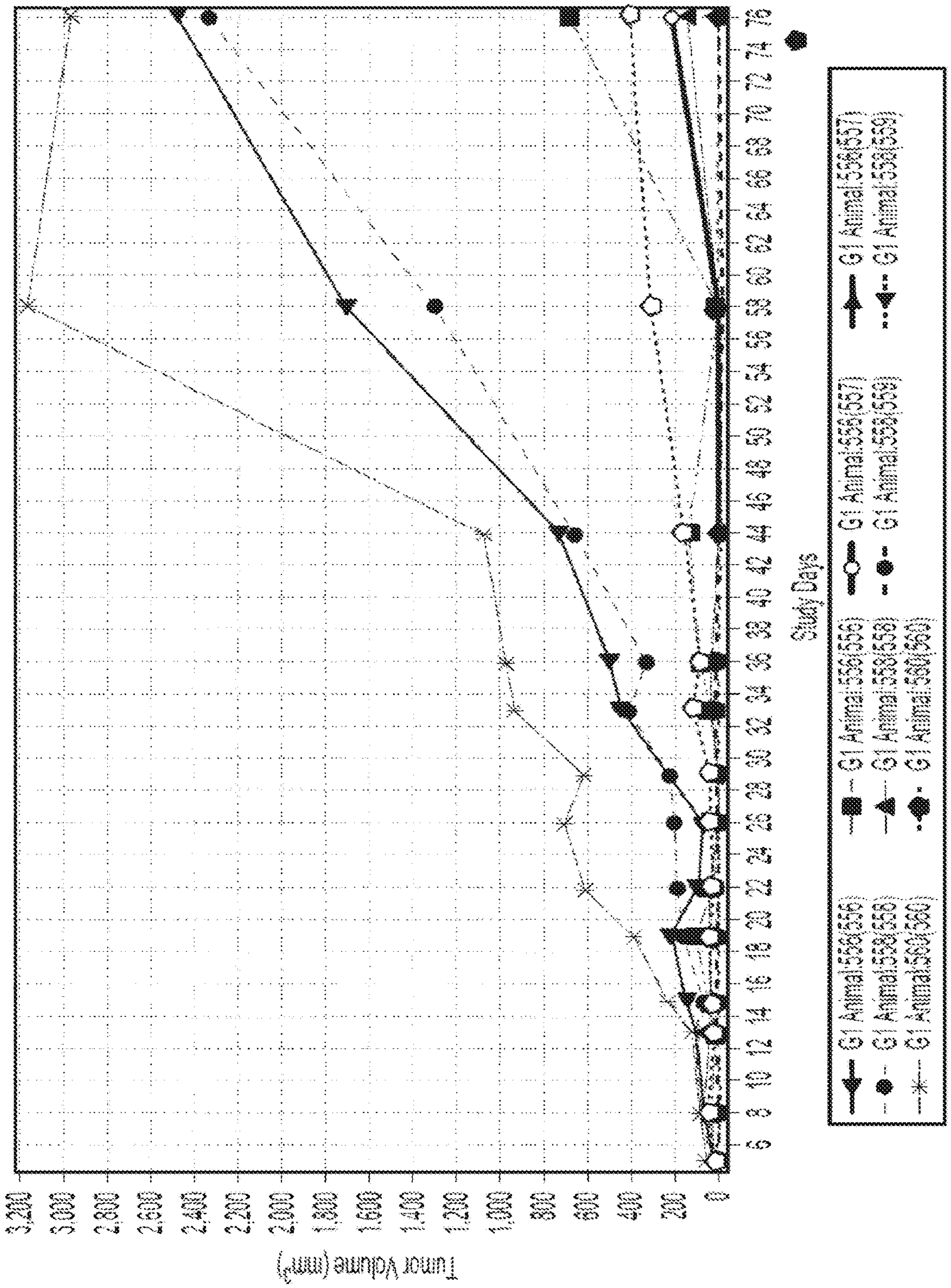
FIG. 1A shows the growth rate of tumors in xenograft models implanted with NCI-H929 cells (H929 models).
Figure 1B:
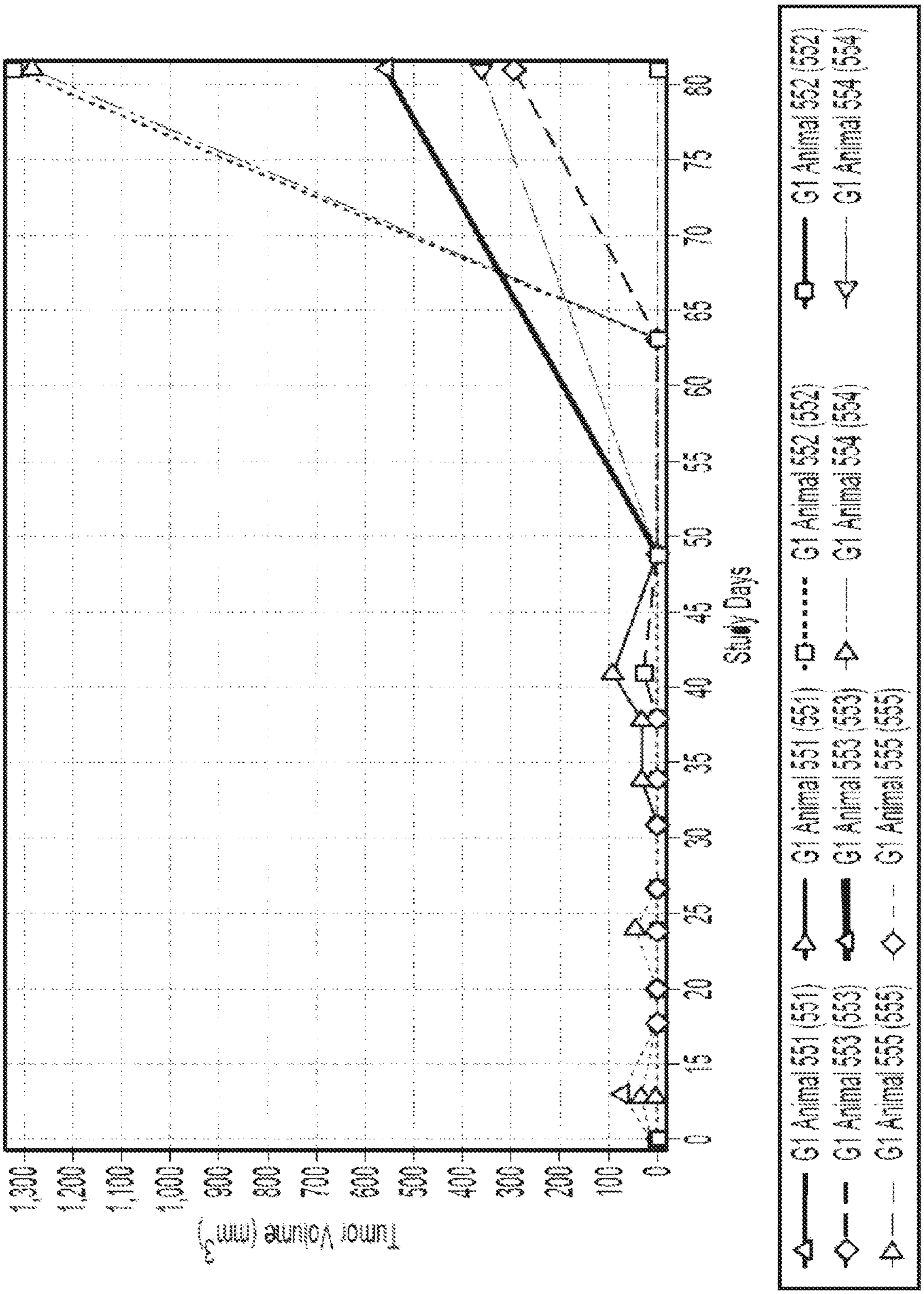
FIG. 1B shows the growth rate of tumors in xenograft models implanted with RPMI 8226 cells (RPMI models).
Figure 2A:
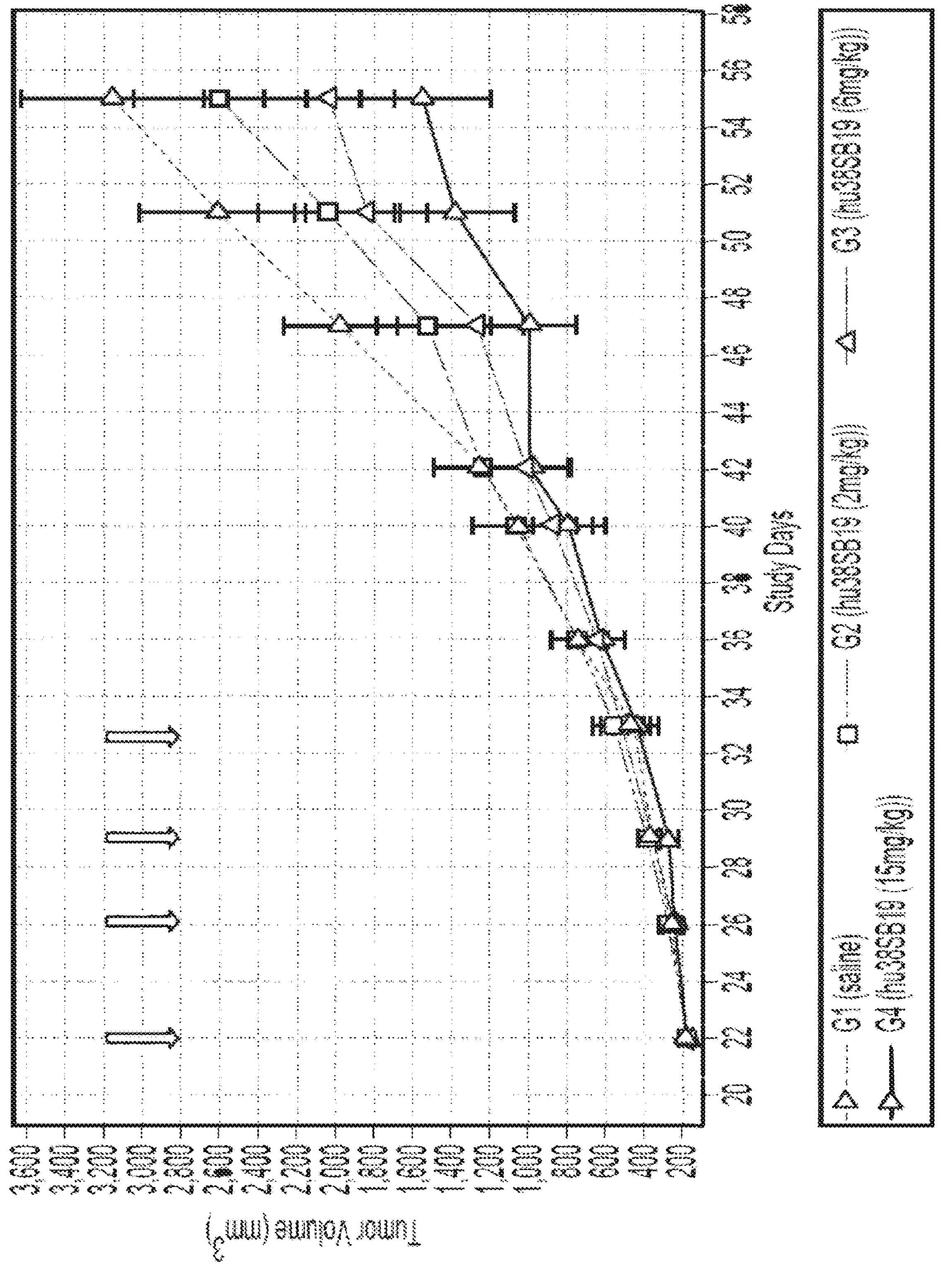
FIG. 2A shows the tumor volume of tumors in RPMI models after treatment with the indicated dose of hu38SB19 at the indicated times (arrows).
Figure 2B:
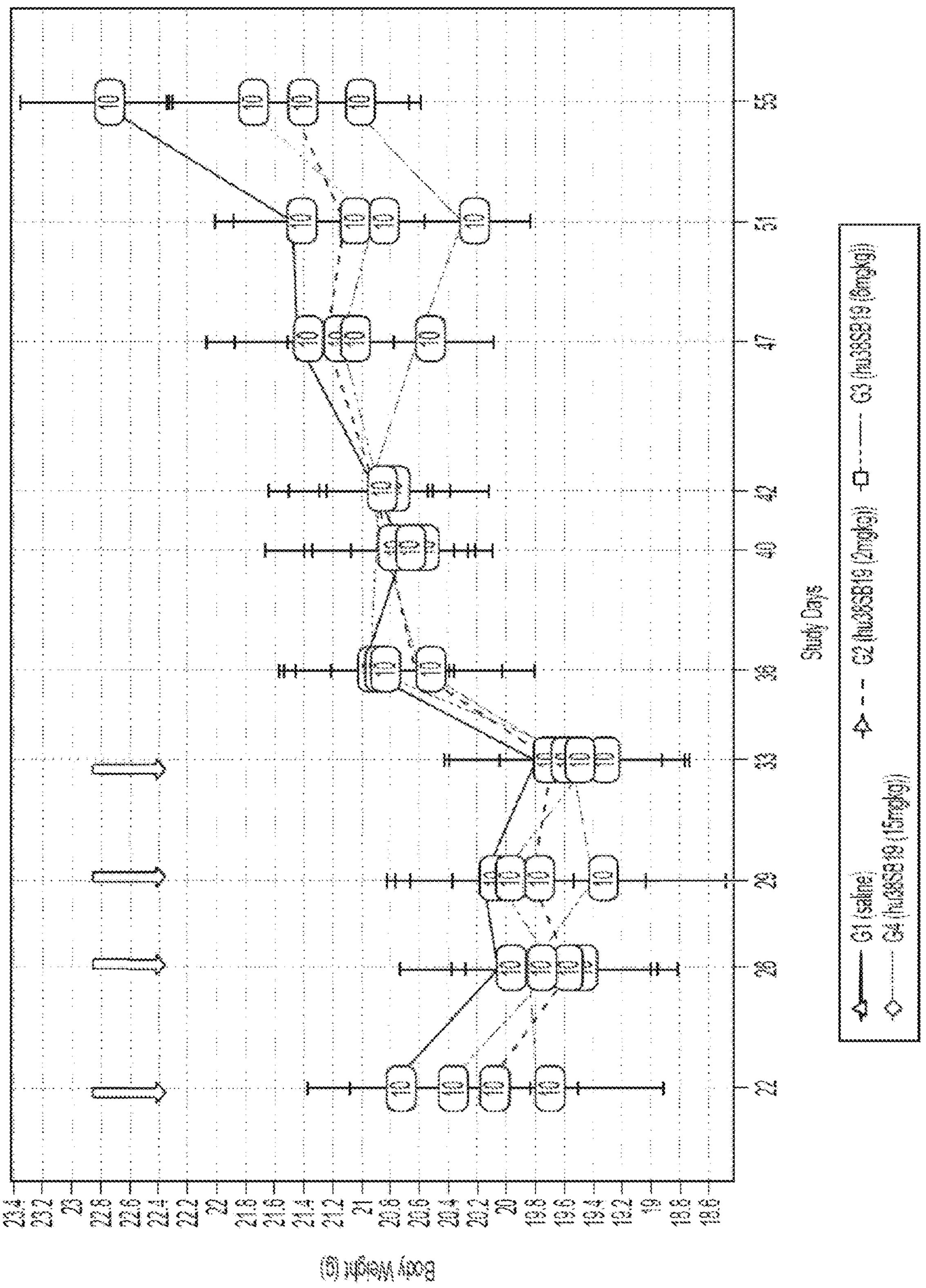
FIG. 2B shows the body weight of the RPMI models after treatment with the indicated dose of hu38SB19 at the indicated times (arrows)
Figure 3A:
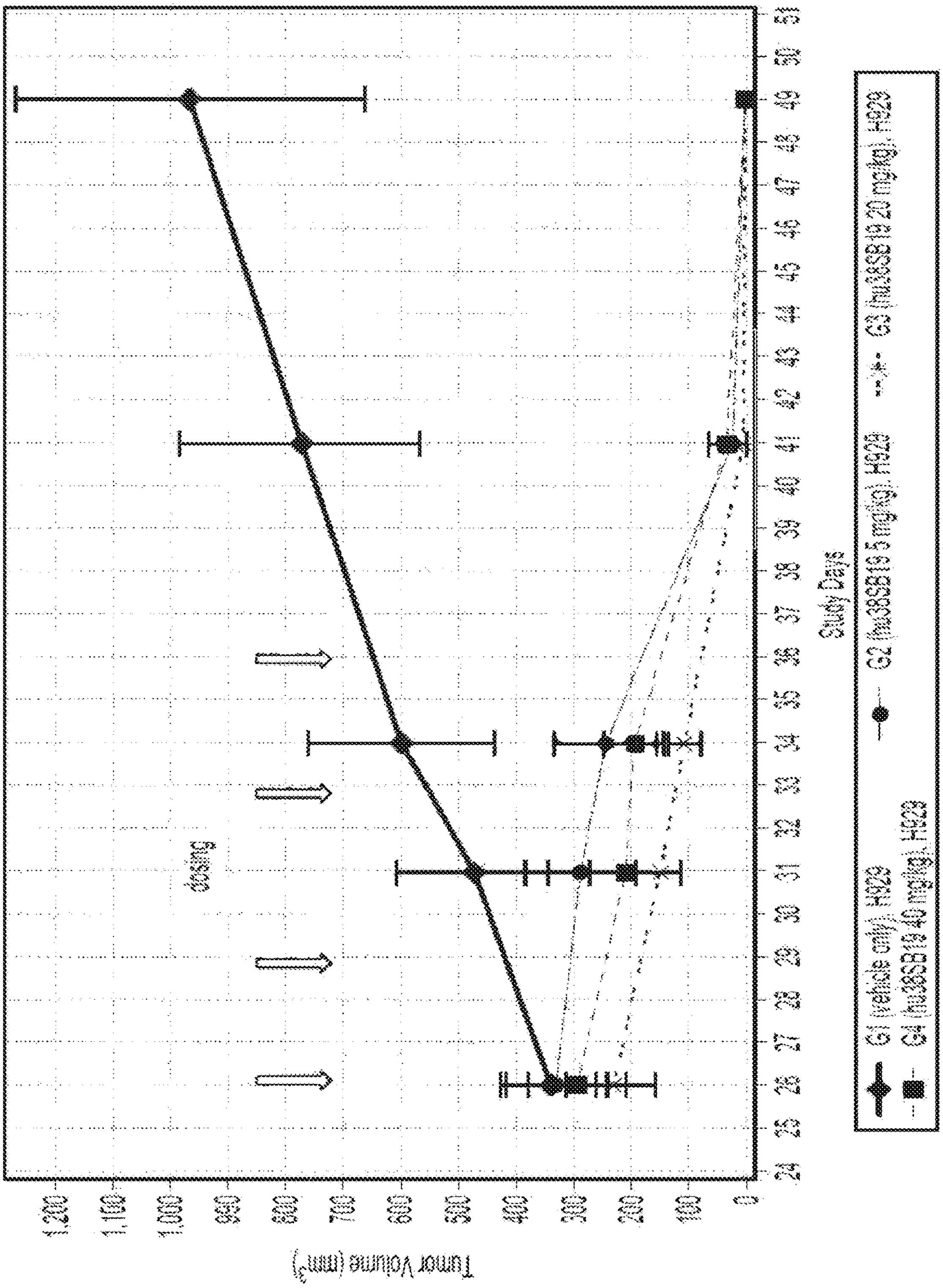
FIG. 3A shows the tumor volume of tumors in H929 models after treatment with the indicated dose of hu38SH39 at the indicated times (arrows).
Figure 3B:
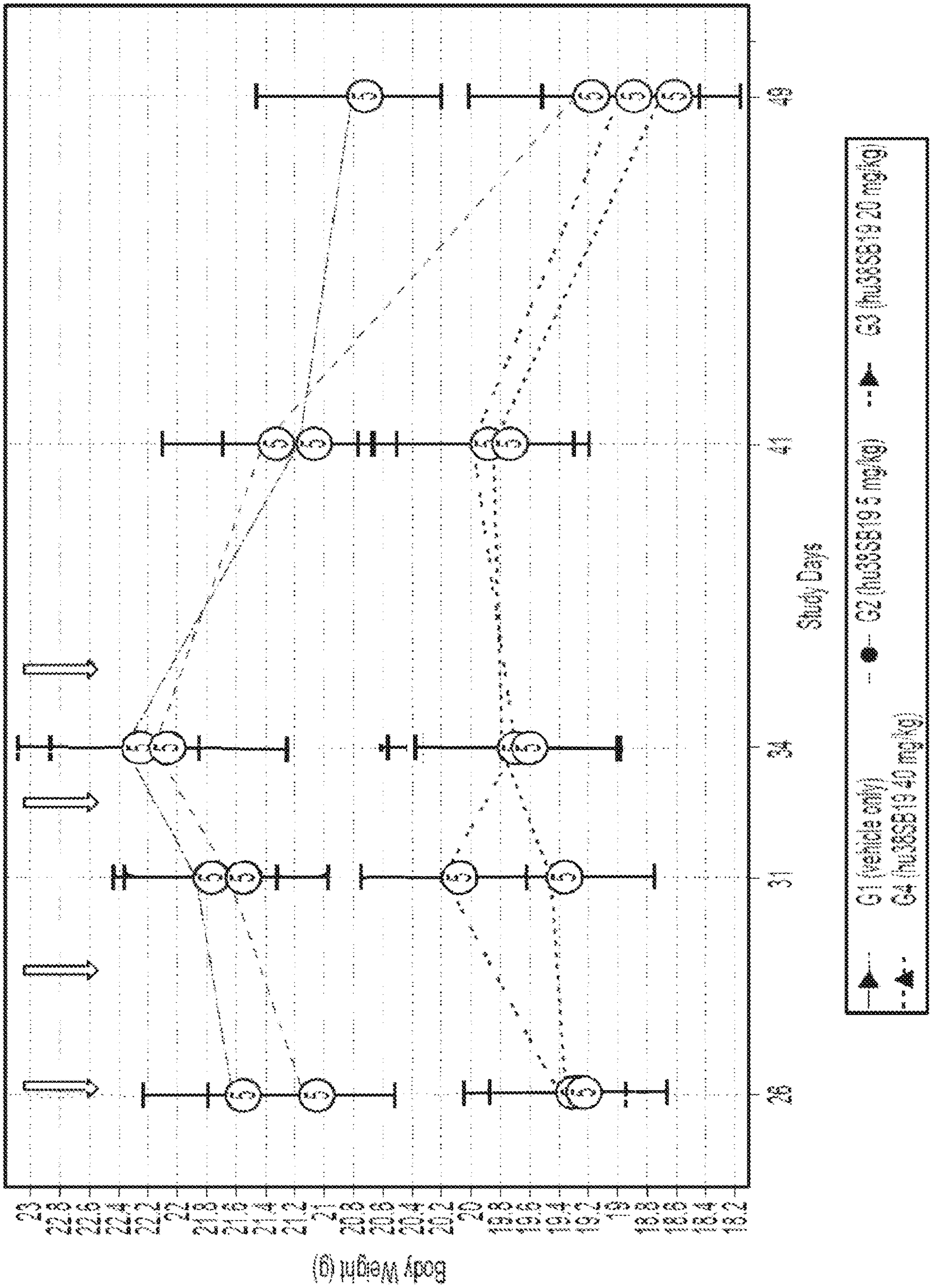
FIG. 3B shows the body weight of the H929 models after treatment with the indicated dose of hu38SB19 at the indicated times (arrows).
Figure 4A:
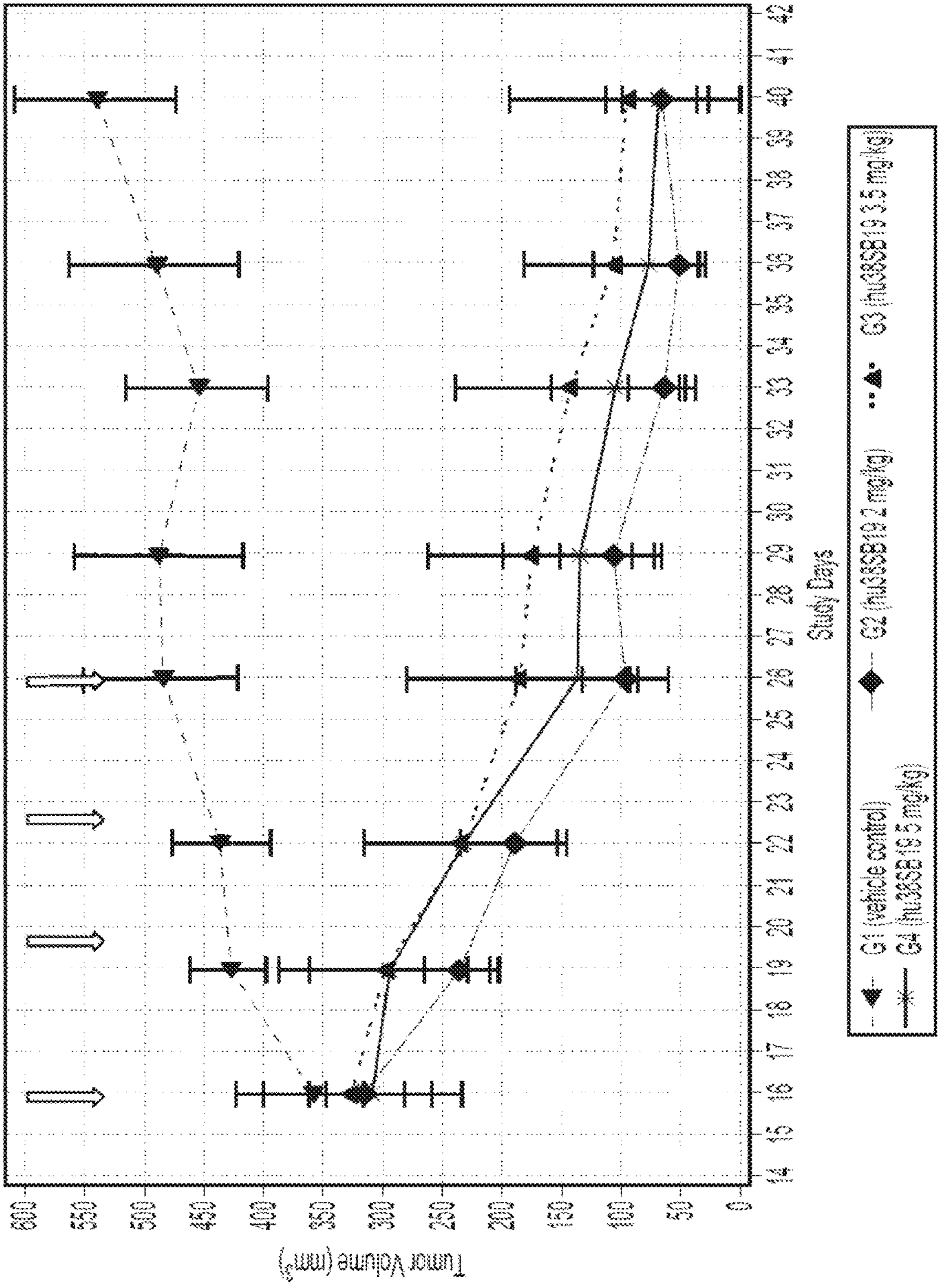
FIG. 4A shows the tumor volume of tumors in H929 models after treatment with the indicated dose of hu38SB19 at the indicated times (arrows).
Figure 4B:
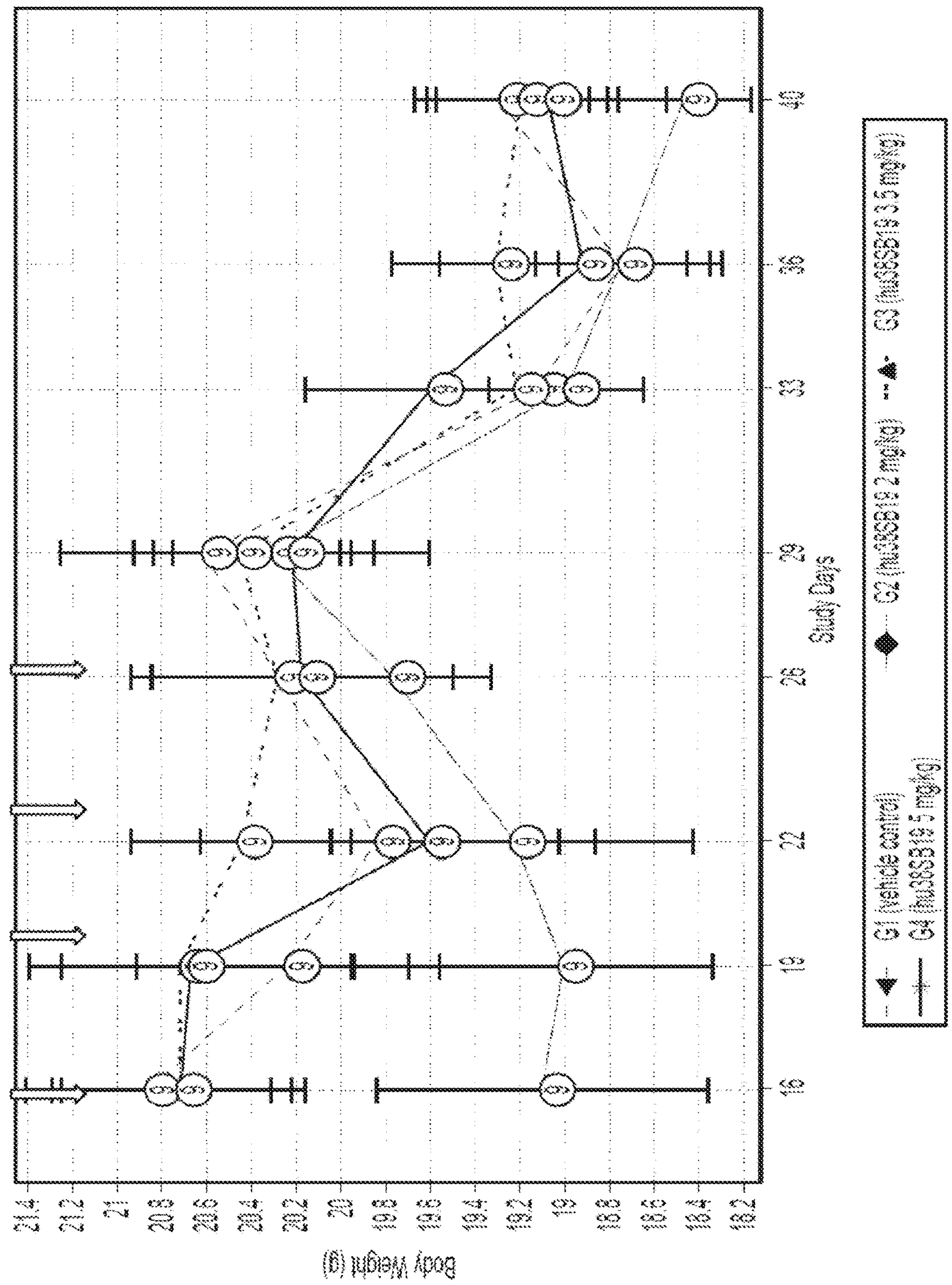
FIG. 4B shows the body weight of the H929 models after treatment the indicated dose of hu38SB19 at the indicated times (arrows).
Figure 5A:
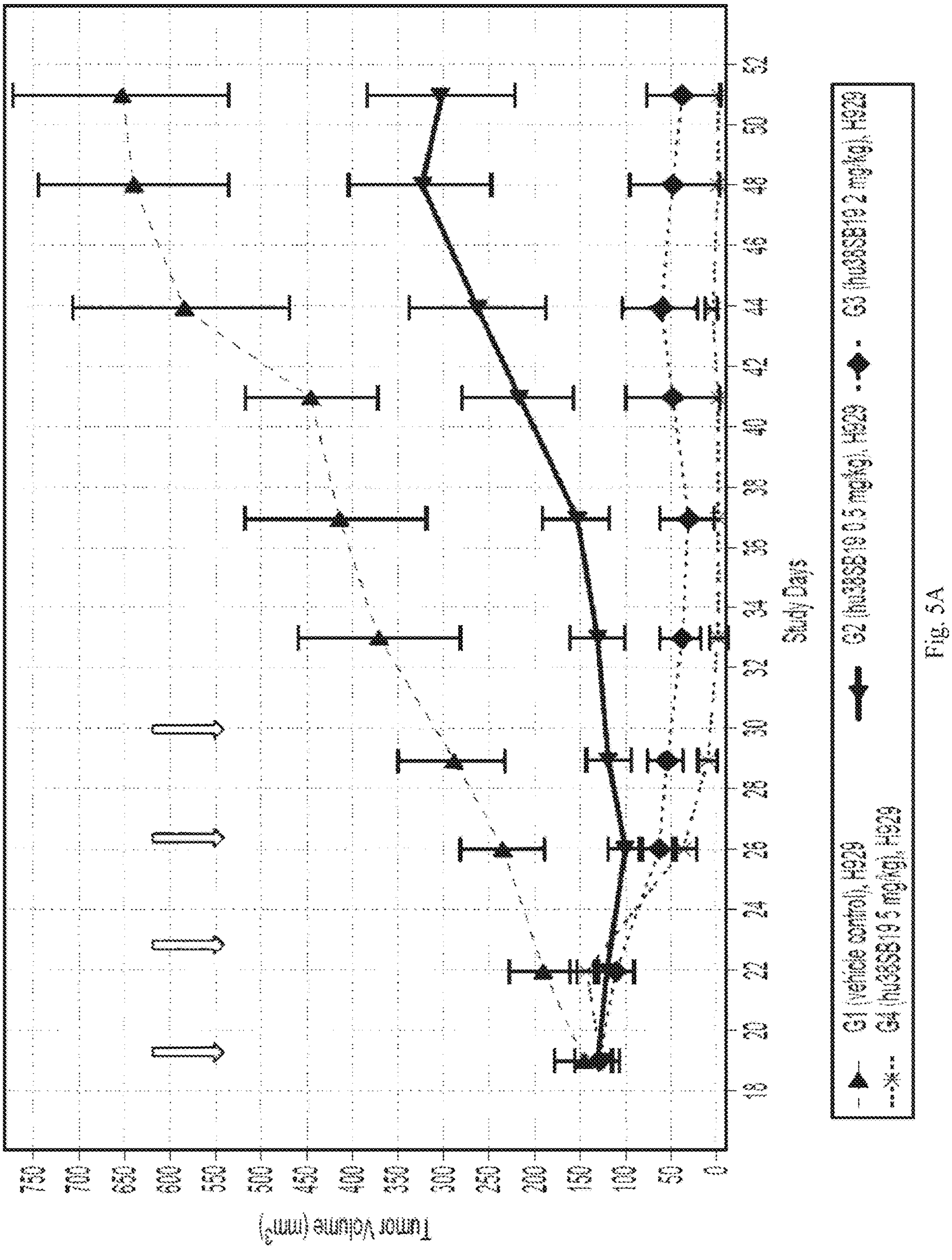
FIG. 5A shows the tumor volume of tumors in H929 models after treatment with the indicated dose of hu38SN19 at the indicated times (arrows).
Figure 5B:
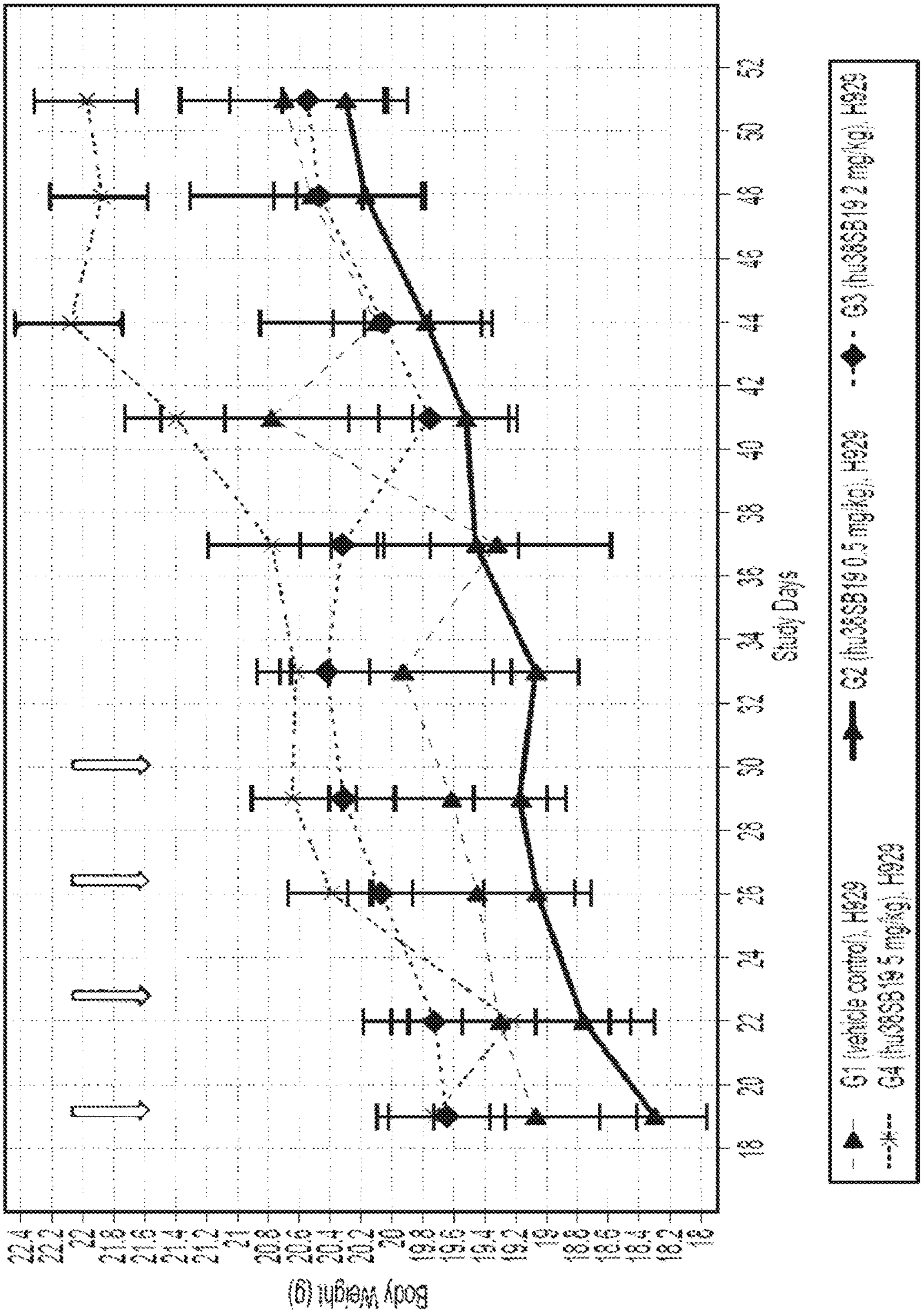
FIG. 5B shows the body weight of the H929 models after treatment with the indicated dose of hu38SB19 at the indicated times (arrows).
Figure 6A:
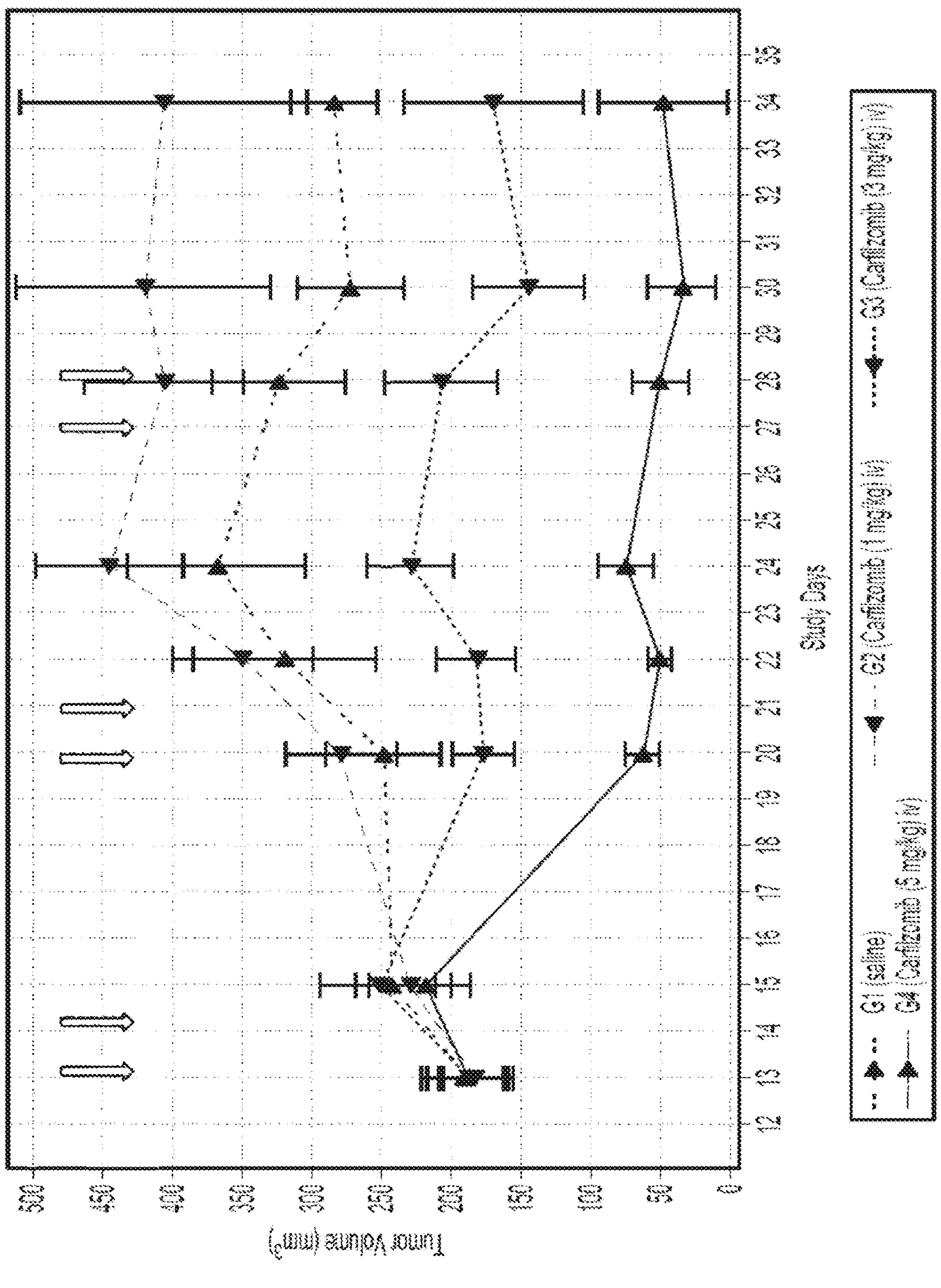
FIG. 6A shows the tumor volume of tumors in H929 models after treatment with indicated dose of carfilzomib at the indicated times (arrows).
Figure 6B:
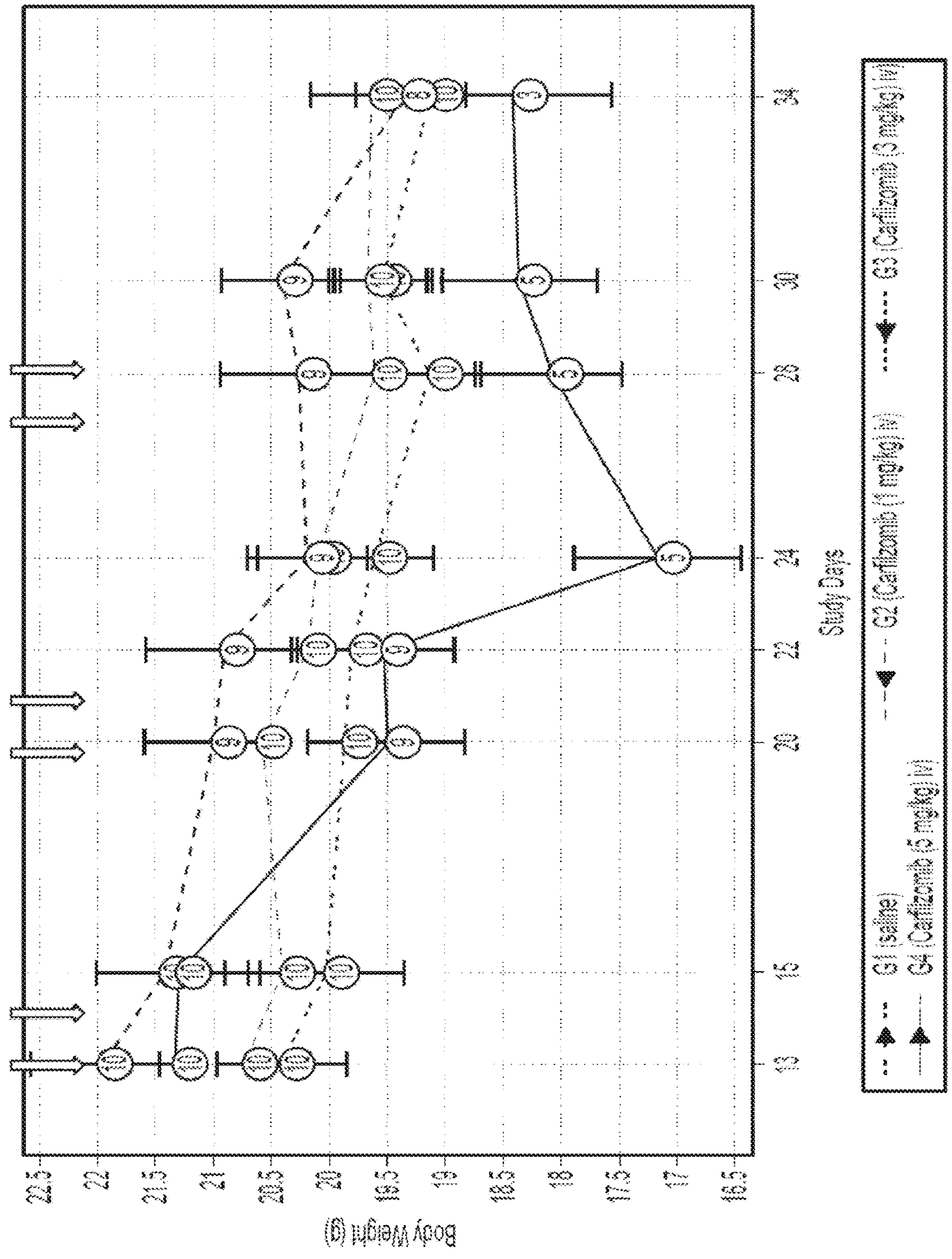
FIG. 6B shows the body weight of the H929 models after treatment with the indicated dose of carfilzomib at the indicated times (arrows).
Figure 7A:
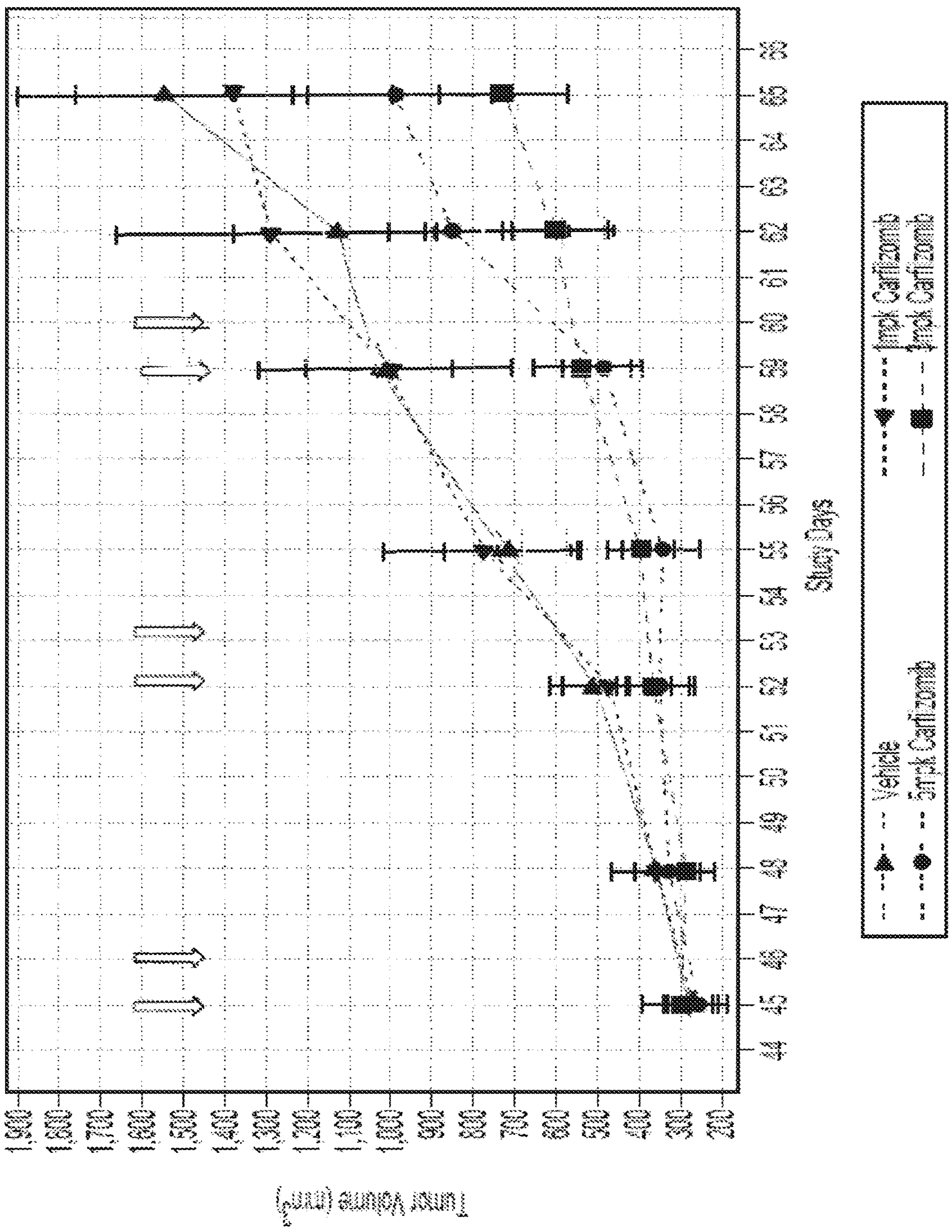
FIG. 7A shows the tumor volume of tumors in RPMI models after treatment with the indicated dose of carfilzomib at the indicated times (arrows).
Figure 7B:
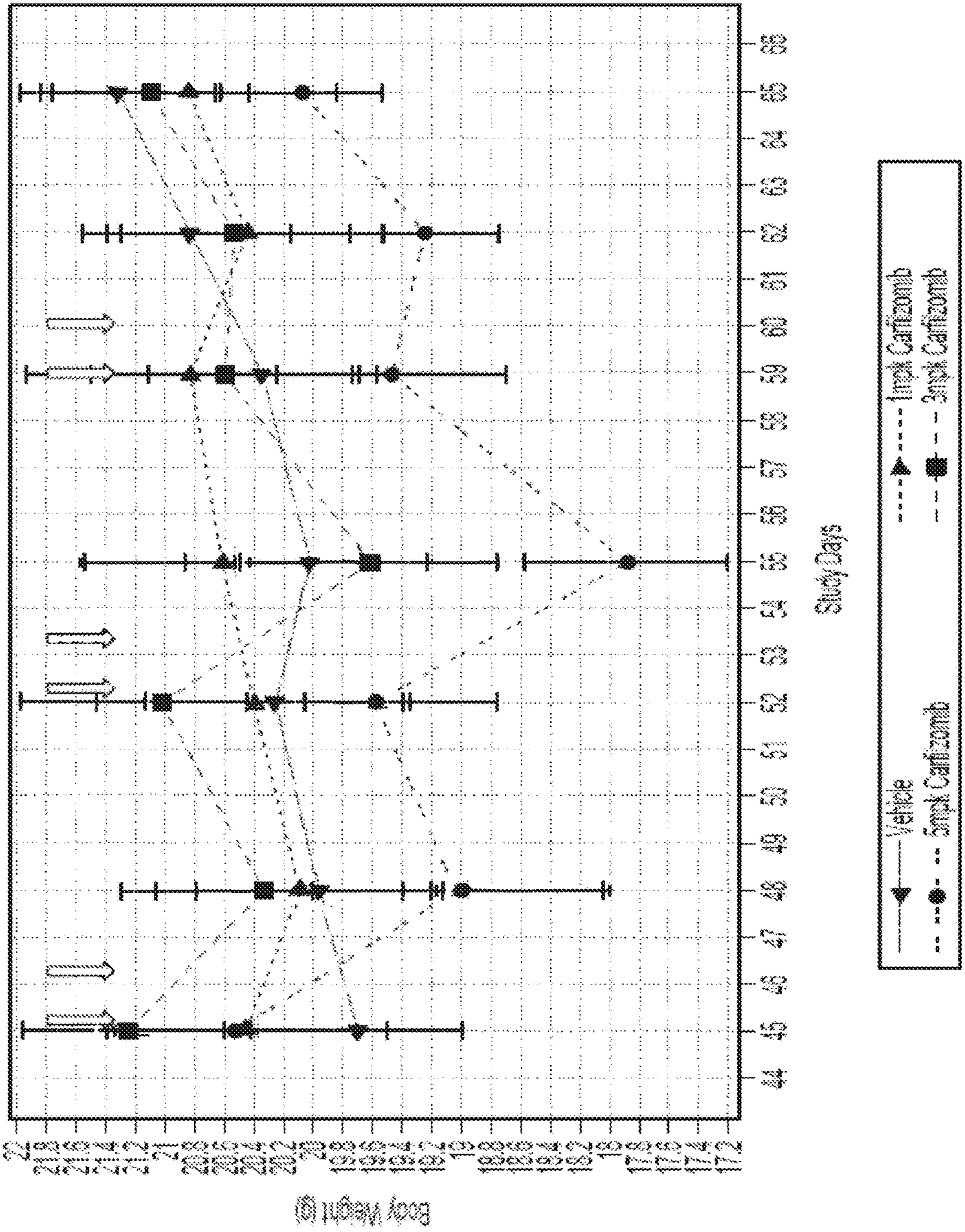
FIG. 7B shows the body weight of the RPMI models after treatment with the indicated dose of carfilzomib at the indicated times (arrows).

In some embodiments, the present invention relates to a method of treating a cancer in a subject which comprises administering one or more anti-CD38 antibodies and one or more carfilzomib compounds to the subject. In some embodiments, the cancer is a hematological malignancy. In some embodiments, the cancer is multiple myeloma. In some embodiments, the cancer is a relapsed multiple myeloma or a refractory multiple myeloma. In some embodiments, the one or more carfilzomib compounds is carfilzomib. In some embodiments, the one or more anti-CD38 antibodies are administered in an effective amount, preferably a synergistic amount. In some embodiments, the one or more anti-CD38 antibodies and/or the one or more carfilzomib compounds are administered in a therapeutically effective amount. In some embodiments, at least one of the one or more anti-CD38 antibodies is capable of killing a CD38+ cell by apoptosis, antibody-dependent cell-mediated cytotoxicity (ADCC), and complement-dependent cytotoxicity (CDC). In some embodiments, the antibody is hu38SB19. In some embodiments, at least one of the one or more anti-CD38 antibodies comprises one or more complementarity-determining region having an amino acid sequence selected from the group consisting of SEQ ID NOs: 13, 14, 81, 15, 16, 17, 18, 1, 2, 3, 4, 5, 6, 7, 8, 9, 10, 11, 12, 19, 20, 21, 22, 23, 24, 25, 26, 27, 28, 29, 30, 31, 32, 33, 34, 35 and 36. In some embodiments, at least one of the one or more anti-CD38 antibodies is selected from the group consisting of: a) an antibody comprising a heavy chain comprising three sequential CDRs having amino acid sequences consisting of SEQ ID NOs: 13, 15 and either SEQ ID NO: 14 or SEQ ID NO: 81, and a light chain comprising three sequential CDRs having amino acid sequences consisting of SEQ ID NOs: 16, 17 and 18; b) an antibody comprising a heavy chain comprising three sequential CDRs having amino acid sequences consisting of SEQ ID NOs: 25, 26 and 27, and a light chain comprising three sequential CDRs having amino acid sequences consisting of SEQ ID NOs: 28, 29 and 30; c) an antibody comprising a heavy chain comprising three sequential CDRs having amino acid sequences consisting of SEQ ID NOs: 1, 2 and 3, and a light chain comprising three sequential CDRs having amino acid sequences consisting of SEQ ID NOs: 4, 5 and 6; d) an antibody comprising a heavy chain comprising three sequential CDRs having amino acid sequences consisting of SEQ ID NOs: 7, 8 and 9, and a light chain comprising three sequential CDRs having amino acid sequences consisting of SEQ ID NOs: 10, 11 and 12; e) an antibody comprising a heavy chain comprising three sequential CDRs having amino acid sequences consisting of SEQ ID NOs: 19, 20 and 21, and a light chain comprising three sequential CDRs having amino acid sequences consisting of SEQ ID NOs: 22, 23 and 24; and f) an antibody comprising a heavy chain comprising three sequential CDRs having amino acid sequences consisting of SEQ ID NOs: 31, 32 and 33, and a light chain comprising three sequential CDRs having amino acid sequences consisting of SEQ ID NOs: 34, 35 and 36. In some embodiments, the antibody comprises a heavy chain having a VH variable region represented by SEQ ID NO: 66, and a light chain having a VL variable region represented by either SEQ ID NO: 62 or SEQ ID NO: 64. In some embodiments, the antibody comprises a heavy chain having a VH variable region represented by SEQ ID NO: 72, and a light chain having a VL variable region represented by either SEQ ID NO: 68 or SEQ ID NO: 70. In some embodiments, the one or more anti-CD38 antibodies are administered intravenously. In some embodiments, the one or more carfilzomib compounds are administered orally. In some embodiments, the one or more anti-CD38 antibodies and the one or more carfilzomib compounds are administered sequentially. In some embodiments, the method further comprises administering a dexamethasone compound, preferably dexamethasone, to the subject. In some embodiments, the dexamethasone compound is administered orally. In some embodiments, the dexamethasone compound is administered at a low dose. In some embodiments, the one or more anti-CD38 antibodies, the one or more carfilzomib compounds, and the dexamethasone compound are administered sequentially. In some embodiments, the one or more anti-CD38 antibodies and the one or more carfilzomib compounds are administered sequentially.

In some embodiments, the present invention relates to a composition comprising a) at least one anti-CD38 antibody, preferably the antibody is capable of killing a CD38+ cell by apoptosis, antibody-dependent cell-mediated cytotoxicity (ADCC), and complement-dependent cytotoxicity (CDC); and b) at least one carfilzomib compound, preferably carfilzomib; and, optionally c) a dexamethasone compound, preferably dexamethasone. In some embodiments, the present invention relates to a composition comprising a) at least one anti-CD38 antibody; and b) at least one carfilzomib compound; and, optionally i) a dexamethasone compound. In some embodiments, the antibody is capable of killing a CD38+ cell by apoptosis, antibody-dependent cell-mediated cytotoxicity (ADCC), and complement-dependent cytotoxicity (CDC). In some embodiments, the antibody is hu38SB19. In some embodiments, the carfilzomib compound is carfilzomib. In some embodiments, the dexamethasone compound is dexamethasone.

In some embodiments, the present invention is directed to a kit comprising a) a first composition comprising at least one anti-CD38 antibody, preferably the antibody is capable of killing a CD38+ cell by apoptosis, antibody-dependent cell-mediated cytotoxicity (ADCC), and complement-dependent cytotoxicity (CDC); and b) a second composition comprising at least one carfilzomib compound, preferably carfilzomib. In some embodiments, the compositions in the kit are packaged for sequential administration to a subject. In some embodiments, the antibody is hu38SB19. In some embodiments, the kit further includes a dexamethasone compound, preferably dexamethasone. In some embodiments, the carfilzomib compound and the dexamethasone compound are packaged for sequential administration to a subject.

In some embodiments, the present invention is directed to a kit comprising at least one anti-CD38 antibody capable of killing a CD38+ cell by apoptosis, antibody-dependent cell-mediated cytotoxicity (ADCC), and complement-dependent cytotoxicity (CDC), packaged together with a label having one or more messages that the at least one anti-CD38 antibody shall be administered in combination with carfilzomib, and optionally with dexamethasone. In some embodiments, the antibody is hu38SB19. In some embodiments, the kit further includes a dexamethasone compound, preferably dexamethasone. In some embodiments, the carfilzomib compound and the dexamethasone compound are packaged for sequential administration to a subject.

In some embodiments, the present invention is directed to a combination of: (i) at least one anti-CD38 antibody, preferably the antibody is capable of killing a CD38+ cell by apoptosis, antibody-dependent cell-mediated cytotoxicity (ADCC), and complement-dependent cytotoxicity (CDC); and (ii) at least one carfilzomib compound, preferably carfilzomib; and, optionally (iii) a dexamethasone compound, preferably dexamethasone. In some embodiments, the present invention relates to a combination comprising a) at least one anti-CD38 antibody; and b) at least one carfilzomib compound; and, optionally i) a dexamethasone compound. In some embodiments, the antibody is capable of killing a CD38+ cell by apoptosis, antibody-dependent cell-mediated cytotoxicity (ADCC), and complement-dependent cytotoxicity (CDC). In some embodiments, the antibody is hu38SB19. In some embodiments, the carfilzomib compound is carfilzomib. In some embodiments, the dexamethasone compound is dexamethasone. In some embodiments, the combination is for sequential use in the treatment of a hematological malignancy, preferably multiple myeloma.

In some embodiments, the present invention is directed to use of (i) at least one anti-CD38 antibody, preferably the antibody is capable of killing a CD38+ cell by apoptosis, antibody-dependent cell-mediated cytotoxicity (ADCC), and complement-dependent cytotoxicity (CDC); and (ii) at least one carfilzomib compound, preferably carfilzomib; and, optionally (iii) a dexamethasone compound, preferably dexamethasone, for the treatment of a hematological malignancy, preferably multiple myeloma. In some embodiments, the present invention relates to use of a) at least one anti-CD38 antibody; and b) at least one carfilzomib compound; and, optionally i) a dexamethasone compound, for the treatment of a hematological malignancy, preferably multiple myeloma. In some embodiments, the antibody is capable of killing a CD38+ cell by apoptosis, antibody-dependent cell-mediated cytotoxicity (ADCC), and complement-dependent cytotoxicity (CDC). In some embodiments, the antibody is hu38SB19. In some embodiments, the carfilzomib compound is carfilzomib. In some embodiments, the dexamethasone compound is dexamethasone.

In some of the various embodiments of the present invention, the subject to be treated is mammalian. In some of the various embodiments of the present invention, the subject to be treated is a test animal such as a mouse. In some of the various embodiments of the present invention, the subject to be treated is human.

DETAILED DESCRIPTION OF THE INVENTION

The present invention relates to methods of treating a cancer in a subject which comprises administering one or more anti-CD38 antibodies and one or more carfilzomib compounds to the subject. As used herein, "treat" or "treating" means to alleviate symptoms, eliminate the causation of the symptoms either on a temporary or permanent basis, or to prevent or slow the appearance of symptoms of the named disorder or condition. As disclosed herein, the efficacy of a carfilzomib compound is considerably improved when administered in conjunction with one or more anti-CD38 antibodies according to the present invention. In fact, the administration of one or more anti-CD38 antibodies which exhibit (a) the capability of killing a $CD38^+$ cell by apoptosis, (b) antibody-dependent cell-mediated cytotoxicity (ADCC), and (c) complement-dependent cytotoxicity (CDC) is believed to considerably improve the efficacy of carfilzomib compounds in the treatment of hematological malignancies, including MM, to a degree that is unexpectedly more than other anti-CD38 antibodies which do not exhibit all three (a)-(c) activities. Therefore, in some embodiments, the one or more anti-CD38 antibodies are capable of (a) killing a $CD38^+$ cell by apoptosis, (b) antibody-dependent cell-mediated cytotoxicity (ADCC), and (c) complement-dependent cytotoxicity (CDC). In some embodiments, the one or more anti-CD38 antibodies and/or the one or more carfilzomib compounds are administered in a therapeutically effective amount. As used herein, a "therapeutically effective amount" of a substance refers to an amount of that substance that results in the alleviation of one or more symptoms, elimination of the causation of the symptoms either on a temporary or permanent basis, and/or the prevention or reduction in the appearance of symptoms of the named disorder or condition in the majority of subjects afflicted with and similarly treated for the named disease or disorder.

In some embodiments, the cancer is one in which CD38 is expressed by the malignant cells. In some embodiments, the cancer is a hematological malignancy of the blood, bone marrow, and/or lymph nodes. In some embodiments, the cancer is a blood cancer. Blood cancers include myeloma, lymphoma and leukemia. The blood cancer might, for instance, be selected from the group consisting of multiple myeloma, non-Hodgkin's lymphoma, Hodgkin's lymphoma, hairy cell leukemia, chronic lymphocytic leukemia, chronic myeloid leukemia, acute myeloid leukemia, and acute lymphocytic leukemia. In some embodiments, the cancer is multiple myeloma (MM). In some embodiments, the cancer is a relapse MM or refractory MM. As used herein, relapsed MM refers to clinically active MM after a period of remission and refractory MM refers to progressive or stable disease while being treated or progressive disease within 3 months of the last does of the prior treatment. See Dimopoulos et al. (2010) Eur J Haematology 88:1-15.

In some embodiments, the subject is mammalian, preferably human. In some embodiments, the subject is an adult human, e.g., at least 18 years. In some embodiments, the subject is in need f treatment for the cancer. In some embodiments, the subject has been diagnosed as having the cancer. In some embodiments, the cancer is in partial or complete remission, however, the one or more carfilzomib compounds and the one or more anti-CD38 antibodies are administered to the subject so as to reduce the likelihood of relapse. In some embodiments, the subject has a Karnofsky performance status equal or superior to 60%. The Karnofsky status runs from 100 to 0, where 100 is "perfect" health and 0 is death (Karnofsky and Burchenal, 1949, "The Clinical Evaluation of Chemotherapeutic Agents in Cancer." In: MacLeod C M (Ed), Evaluation of Chemotherapeutic Agents. Columbia Univ Press). In some embodiments, the subject has undergone at least one or two prior therapies for multiple myeloma, induction therapy being considered one prior therapy. In some embodiments, the subject exhibits evidence that either the cancer progressed while the subject underwent a prior therapy, or that the subject was refractory to the prior therapy.

In some embodiments, the anti-CD38 antibodies specifically bind CD38. In some embodiments, the anti-CD38 antibodies are raised against CD38 or an epitope thereof. In some embodiments, the anti-CD38 antibodies are monoclonal antibodies. In some embodiments, one or more of the anti-CD38 antibodies according to the present invention are monoclonal antibodies as described in WO 2008/047242, which is herein incorporated by reference in its entirety. In some embodiments, one or more of the anti-CD38 antibodies are monoclonal antibodies 38SB13, 38SB18, 38SB19, 38SB30, 38SB31, and 38SB39 as described in WO 2008/047242, which is herein incorporated by reference in its entirety. In some embodiments, the one or more anti-CD38 antibodies are capable of killing $CD38^+$ cells by three different cytotoxic mechanisms, induction of apoptosis, antibody-dependent cell-mediated cytotoxicity (ADCC), and complement-dependent cytotoxicity (CDC).

The term "antibody" is used herein in the broadest sense and includes monoclonal antibodies (including full length monoclonal antibodies) of any isotype such as IgG, IgM, IgA, IgD and IgE, polyclonal antibodies, multispecific antibodies, chimeric antibodies, and antibody fragments. As used herein, the prefix "anti-" when in conjunction with an antigen, indicates that the given antibody is reactive with the given antigen. An antibody reactive with a specific antigen can be generated by synthetic and/or recombinant methods such as selection of libraries of recombinant antibodies in phage or similar vectors, or by immunizing an animal with the antigen or an antigen-encoding nucleic acid.

A typical IgG antibody is comprised of two identical heavy chains and two identical light chains that are joined by disulfide bonds. Each heavy and light chain contains a constant region and a variable region. Each variable region contains three segments called "complementarity-determining regions" ("CDRs") or "hypervariable regions", which are primarily responsible for binding an epitope of an antigen. They are usually referred to as CDR1, CDR2, and CDR3, numbered sequentially from the N-terminus. The more highly conserved portions of the variable regions outside of the CDRs are called the "framework regions". As used herein, "$V_H$" "VH" refers to the variable region of an immunoglobulin heavy chain of an antibody, including the heavy chain of an Fv, scFv, dsFv, Fab, Fab' or $F(ab')_2$ fragment. Reference to "$V_L$" or "VL" refers to the variable region of the immunoglobulin light chain of an antibody, including the light chain of an Fv, scFv, dsFv, Fab, Fab' or $F(ab')_2$, fragment.

The antibodies according to the present invention may be, e.g., murine, chimeric, and/or humanized antibodies. As used herein, a "chimeric antibody" is an antibody in which the constant region, or a portion thereof, is altered, replaced, or exchanged, so that the variable region is linked to a constant region of a different species, or belonging to another antibody class or subclass. "Chimeric antibody" also refers to an antibody in which the variable region, or a portion thereof, is altered, replaced, or exchanged, so that the constant region is linked to a variable region of a different species, or belonging to another antibody class or subclass. Methods for producing chimeric antibodies are known in the art. See e.g., Morrison, 1985, Science, 229: 1202; Oi et al., 1986, BioTechniques, 4; 214; Gillies et al., 1989, J. Immunol. Methods, 125: 191-202; U.S. Pat. Nos. 5,807,715; 4,816,567; and 4,816,397, which are incorporated herein by reference in their entireties. The term "humanized antibody", as used herein, refers to a chimeric antibody which contain minimal sequence derived from non-human immunoglobulin. The goal of humanization is a reduction in the immunogenicity of a xenogenic antibody, such as a murine antibody, for introduction into a human, while maintaining the full antigen binding affinity and specificity of the antibody. Humanized antibodies, or antibodies adapted for non-rejection by other mammals, may be produced using several technologies such as resurfacing and CDR grafting. As used herein, the resurfacing technology uses a combination of molecular modelling, statistical analysis and mutagenesis to alter the non-CDR surfaces of antibody variable regions to resemble the surfaces of known antibodies of the target host. The CDR grafting technology involves substituting the complementarity determining regions of, for example, a mouse antibody, into a human framework domain, e.g., see W0 92/22653. Humanized chimeric antibodies preferably have constant regions and variable regions other than the complementarity determining regions (CDRs) derived substantially or exclusively from the corresponding human antibody regions and CDRs derived substantially or exclusively from a mammal other than a human.

Strategies and methods for the resurfacing of antibodies, and other methods for reducing immunogenicity of antibodies within a different host, are disclosed in U.S. Pat. No. 5,639,641, which is hereby incorporated in its entirety by reference. Antibodies can be humanized using a variety of other techniques including CDR-grafting (EP 0 239 400; WO 91/09967; U.S. Pat. Nos. 5,530,101; and 5,585,089), veneering or resurfacing (EP 0 592 106; EP 0 519 596; Padlan E. A., 1991, Molecular Immunology 28(4/5): 489-498; Studnicka G. M. et al., 1994, Protein Engineering, 7(6): 805-814; Roguska M. A. et al., 1994, PNAS, 91: 969-973), chain shuffling (U.S. Pat. No. 5,565,332), and identification of flexible residues (PCT/US2008/074381). Human antibodies can be made by a variety of methods known in the art including phage display methods. See also U.S. Pat. Nos. 4,444,887, 4,716,111, 5,545,806, and 5,814,318; and international patent application publication numbers WO 98/46645, WO 98/50433, WO 98/24893, WO 98/16654, WO 96/34096, WO 96/33735, and WO 91/10741 (said references incorporated by reference in their entireties).

In some embodiments, one or more of the anti-CD38 antibodies according to the invention are capable of killing a $CD38^+$ cell by apoptosis, antibody-dependent cell-mediated cytotoxicity (ADCC), and complement-dependent cytotoxicity (CDC). In some embodiments, one or more of the anti-CD38 antibodies according to the invention are capable of killing said $CD38^+$ cells by apoptosis even in the absence of stroma cells or stroma-derived cytokines. These activities can be assessed as described in WO 2008/047242, which is hereby incorporated by reference in its entirety.

In some embodiments according to the invention, one or more anti-CD38 antibodies are selected from the group consisting of 38SB13, 38SB18, 38SB19, 38SB30, 38SB31, 38SB39, and antibodies cross-competing with 38SB13, 38SB18, 38SB19, 38SB30, 38SB31 or 38SB39. The hybridoma cell lines producing the 38SB13, 38SB18, 38SB19, 38SB30, 38SB31, and 38SB39 murine anti-CD38 antibodies have been deposited at the American Type Culture Collection (10801 University Bid, Manassas, VA, 20110-2209, USA), on Jun. 21, 2006, under the deposit numbers PTA-7667, PTA-7669, PTA-7670, PTA-7666, PTA-7668, and PTA-7671, respectively (as described in WO 2008/047242, which is herein incorporated by reference in its entirety).

As disclosed herein, references to SEQ ID NOs refers to the sequences set forth in the Sequence Listing submitted herewith and also as recited in WO 2008/047242, which is herein incorporated by reference in its entirety. In some embodiments, the anti-CD38 antibodies according to the present invention may, for instance, comprise a heavy chain comprising three sequential CDRs having amino acid sequences represented by SEQ ID NOs: 1, 2, and 3, and a light chain comprising three sequential CDRs having amino acid sequences represented by SEQ ID NOs: 5, and 6. An example of such an antibody is the 38SB13 antibody, which comprises a heavy chain having a $V_H$ variable region represented by SEQ ID NO: 50, and a light chain having a $V_L$ variable region represented by SEQ ID NO: 38.

In some embodiments, the anti-CD38 antibodies according to the present invention may, for instance, comprise a heavy chain comprising three sequential CDRs having amino acid sequences represented by SEQ ID NOs: 7, 8, and 9, and a light chain comprising three sequential CDRs having amino acid sequences represented by SEQ ID NOs: 10, 11, and 12. An example of such an antibody is the 38SB18 antibody, which comprises a heavy chain having a $V_H$ variable region represented by SEQ ID NO: 52 and a light chain having a $V_L$ variable region represented by SEQ ID NO: 40.

In some embodiments, the anti-CD38 antibodies according to the present invention may, for instance, comprise a heavy chain comprising three sequential CDRs having amino acid sequences represented by SEQ ID NO: 13, SEQ ID NO: 15 and either SEQ ID NO: 14 or SEQ ID NO: 81, and a light chain comprising three sequential CDRs having amino acid sequences represented by SEQ ID NOs: 16, 17, and 18. An example of such an antibody is the 38SB19 antibody, which comprises a heavy chain having a $V_H$ variable region represented by SEQ ID NO: 54 and a light chain having a $V_L$ variable region represented by SEQ ID NO: 42. Specific examples of humanized versions of 38SB19 (hu38SB19) include antibodies comprising a heavy chain having a $V_H$ variable region represented by SEQ ID NO: 66, and a light chain having a $V_L$ variable region represented by either SEQ ID NO: 62 or SEQ ID NO: 64. hu38SB19 is a humanized anti-CD38 antibody currently undergoing clinical evaluation in CD38-positive hematologic malignancies, including multiple myeloma. Previous and current studies demonstrate that the anti-myeloma activity associated with this agent involve mechanisms of ADCC and CDC, as well as novel, direct apoptotic and anti-ADP-ribosyl cyclase activity. See Marie-Cécile Wetzel, Céline Nicolazzi, François Vallée, et al. hu38SB19: characterization of a potent phase I humanized anti-CD38 antibody for the treatment of multiple myeloma and other hematologic malignancies. AACR Annual Meeting 2013, Abstract #4735.

In some embodiments, the anti-CD38 antibodies according to the present invention may, for instance, comprise a heavy chain comprising three sequential CDRs having amino acid sequences represented by SEQ ID NOs: 19, 20, and 21, and a light chain comprising three sequential CDRs having amino acid sequences represented by SEQ ID NOs: 22, 23, and 24. An example of such an antibody is the 38SB30 antibody, which comprises a heavy chain having a $V_H$ variable region represented by SEQ ID NO: 56 and a light chain having a $V_L$ variable region represented by SEQ ID NO: 44.

In some embodiments, the anti-CD38 antibodies according to the present invention may, for instance, comprise a heavy chain comprising three sequential CDRs having amino acid sequences represented by SEQ ID NOs: 25, 26, and 27, and a light chain comprising three sequential CDRs having amino acid sequences represented by SEQ ID NOs: 28, 29, and 30. An example of such an antibody is the 38SB31 antibody, which comprises a heavy chain having a $V_H$ variable region represented by SEQ ID NO: 58 and a light chain having a $V_L$ variable region represented by SEQ ID NO: 46. Specific examples of humanized versions of 38SB31 (hu38SB31) include antibodies comprising a heavy chain having a variable region represented by SEQ ID NO: 72, and a light chain having a $V_L$ variable region represented by either SEQ ID NO: 68 or SEQ ID NO: 70.

In some embodiments, the anti-CD38 antibodies according to the present invention may, for instance, comprise a heavy chain comprising three sequential CDRs having amino acid sequences represented by SEQ ID NOs: 31, 32 and 33, and a light chain comprising three sequential CDRs having amino acid sequences represented by SEQ ID NOs: 34, 35, and 36. An example of such an antibody is the 38SB39 antibody, which comprises a heavy chain having a $V_H$ variable region represented by SEQ ID NO: 60 and a light chain having a $V_L$ variable region represented by SEQ ID NO: 48.

In some embodiments, the anti-CD38 antibodies according to the invention are humanized antibodies consisting of two identical heavy chains and of two identical light chains, wherein each chain consists of one constant region and of one variable region.

As used herein, a "carfilzomib compound" refers to carfilzomib (S)-4-Methyl-N-((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)pentanamide and carfilzomib derivatives. As used herein, "carfilzomib derivatives" refers to compounds which have 2-acetamido-N-(1-((1-(1-methylcyclopropyl)-1-oxopropan-2-yl)amino)-1-oxopropan-2-yl)propanamide, i.e.,

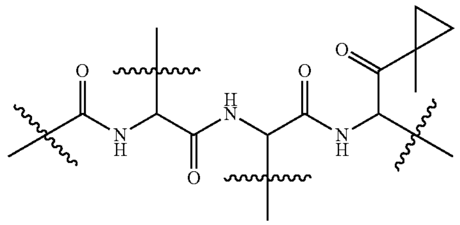 [SMILES: *C(=O)NC(*)C(=O)NC(*)C(=O)NC(*)C(=O)C1(C)CC1]

which may or may not be substituted, as part of its structural formula. In some embodiments, carfilzomib derivatives include compounds which have the following structure, which may or may not be substituted, as part of its structural backbone:

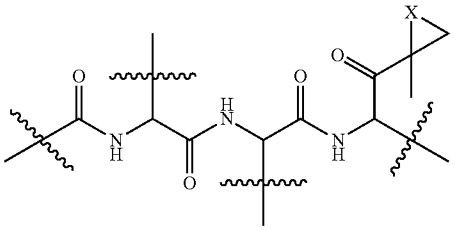

wherein X is selected from O, NH, and N—$C_{1-6}$alkyl, preferably O. Examples of "carfilzomib derivatives" according to the present invention include those as set forth U.S. Pat. Nos. 7,232,818; 7,417,042; 7,491,704; 7,737,112; 8,129,346; 8,207,125; 8,207,126; 8,207,127; and 8,207,297.

In some embodiments, the one or more anti-CD38 antibodies are administered in an effective amount. As used herein, an effective amount of the one or more anti-CD38 antibodies is an amount which results in an additive or a synergistic effect with the one or more carfilzomib compounds. As used herein, a "synergistic amount" is one that results in a synergistic effect. As used herein, a "synergistic effect" refers to the effect of the combination of the one or more anti-CD38 antibodies and the one or more carfilzomib compounds which is more than their expected additive effect. In some embodiments, the one or more anti-CD38 antibodies are administered before, during, and/or after the administration of the one or more carfilzomib compounds. In some embodiments, the one or more anti-CD38 antibodies and the one or more carfilzomib compounds are co-administered in the form of a single composition, e.g., as a mixture.

Thus, in some embodiments, the present invention is directed to compositions comprising a mixture of at least one anti-CD38 antibody and at least one carfilzomib compound. In some embodiments, the mixture comprises the at least one anti-CD38 antibody in an amount that results in an additive or a synergistic effect with the at least one carfilzomib compound in a subject when both are administered. In some embodiments, the at least one anti-CD38 antibody in the mixture is one which is capable of killing a $CD38^+$ cell by apoptosis, antibody-dependent cell-mediated cytotoxicity (ADCC), and complement-dependent cytotoxicity (CDC); and at least one carfilzomib compound.

For the purposes of the present invention, the methods and compositions of the present invention are not exclusively limited to those which are obtained by physical association of the anti-CD38 antibodies and the carfilzomib compound, but also to those which permit a separate administration, which can be simultaneous or spaced out over a period of time. Thus, in some embodiments, the present invention is directed to a first composition comprising the one or more anti-CD38 antibodies, and a second composition comprising one or more carfilzomib compounds. In some embodiments, the at least one anti-CD38 antibody is one which is capable of killing a $CD38^+$ cell by apoptosis, antibody-dependent cell-mediated cytotoxicity (ADCC), and complement-dependent cytotoxicity (CDC); and at least one carfilzomib compound. In some embodiments, the amount of the one or more anti-CD38 antibodies provided in the first composition is one that results in an additive or a synergistic effect with the at least one carfilzomib compound in the second composition in a subject when both are administered.

In some embodiments, the first and second compositions may be packaged in a kit. Thus, in some embodiments, the present invention is directed to kits which comprise a first composition comprising the one or more anti-CD38 antibodies, and a second composition comprising one or more carfilzomib compounds. In some embodiments, the first and second composition may be mixed together before administering to a subject. In some embodiments, the first and second compositions, may be administered either simultaneously or sequentially (i.e., spaced out over a period of time) so as to obtain the maximum efficacy, additivity, synergy, or a combination thereof of the combination. In some embodiments, the present invention is directed to kits comprising at least one anti-CD38 antibody packaged together with a label having one or more messages that the anti-CD38 antibody shall or might be administered in combination with carfilzomib and optionally with dexamethasone. The kits according to the present invention may further comprise one or more messages that the antibody shall or might be administered to a subject suffering from a blood cancer such as multiple myeloma (e.g., relapsed or refractory multiple myeloma). In some embodiments, the one or more anti-CD38 antibodies in the kits of the present invention are those which are capable of killing a $CD38^+$ cell by apoptosis, antibody-dependent cell-mediated cytotoxicity (ADCC), and complement-dependent cytotoxicity (CDC).

In some embodiments, the compositions of the present invention are pharmaceutical compositions. As used herein, the term "pharmaceutical composition" refers to a composition comprising at least one active principle (e.g., an anti-CD38 antibody or a carfilzomib compound) and at least one pharmaceutically acceptable carrier. Pharmaceutically acceptable carriers are well known to the skilled in the art, and usually depend on the chosen route of administration. Pharmaceutical compositions according to the present invention may be provided in any form or formulation that is suitable for the chosen route of administration, such as e.g., a solution in case of an intravenous route of administration, e.g., capsules, pills or tablets in case of an oral route of administration, etc.

The dosage regimen of the active principles and of the pharmaceutical composition described herein can be chosen by prescribing physicians, based on their knowledge of the art, including information published by regulatory authorities. For example, carfilzomib is typically administered intravenously. According to the U.S. Food and Drug Administration (FDA), carfilzomib might be administered intravenously, e.g., over 2 to 10 minutes, on two consecutive days each week for three weeks (Days 1, 2, 8, 9, 15, and 16), followed by a 12-day rest period (Days 17 to 28). In some embodiments, the recommended Cycle 1 dose is 20 $mg/m^2$/day and, if tolerated, the doses of Cycle 2 and subsequent cycles are increased to 27 $mg/m^2$/day. In some embodiments, patients are hydrated prior to and/or following administration. Since, however, co-administration of the one or more anti-CD38 antibodies and the one or more carfilzomib compounds results in an additive or a synergistic effect, the dosing of the carfilzomib compound may be adjusted accordingly, e.g., the dose changed and/or the dosing schedule modified. Of course, prescribing physicians might reconsider which dose and schedule to use depending on the condition and disease status of the patient and based upon clinical and laboratory findings.

As the FDA recommends pre-medication with dexamethasone prior to all Cycle 1 doses, during the first cycle of dose escalation, and if infusion reaction symptoms develop or reappear, the methods and compositions of the present invention may further include dexamethasone, which is member of the glucocorticoid class of steroid drugs, and acts as an anti-inflammatory and immunosuppressant. Thus, in some embodiments, the treatment methods of the present invention further comprise administering a dexamethasone compound to the subject being treated with the one or more anti-CD38 antibodies and the one or more carfilzomib compounds. Similarly, the compositions and kits of the present invention which comprise the one or more anti-CD38 antibodies and/or the one or more carfilzomib compounds may further comprise a dexamethasone compound. As used herein, a "dexamethasone compound" refers to dexamethasone ((8S,9R,10S,11S,13S,14S,16R,17R)-9-Fluoro-11,17-dihydroxy-17-(2-hydroxyacetyl)-10,13,16-trimethyl-6,7,8,9,10,11,12,13,14,15,16,17-dodecahydro-3H-cyclopenta[a]phenanthren-3-one) and dexamethasone derivatives. As used herein, a "dexamethasone derivative" refers to a compound having the following structural formula:

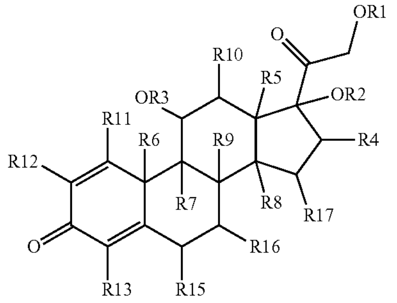

wherein R1-R17 are each independently H, a halogen, an alkyl, an alkoxy, amino, or an alkylamine. In some preferred embodiments, R1-R3 are H. In some preferred embodiments, R4-R6 are methyl. In some preferred embodiments, R7 is a halogen, preferably fluorine. In some preferred embodiments, R8 is H. In some preferred embodiments, R1-R3 are H, R4-R6 are methyl, R7 is a halogen, preferably fluorine, and R8 is H.

In some embodiments, the dexamethasone compound may be administered orally. In some embodiments, the dexamethasone compound may be administered at the same or a lower dose than the dose recommended for dexamethasone by the EMA.

The compositions of the present invention may be used as a medicament and/or for use in the manufacture of a medicament. In some embodiments, the compositions of the present invention may be used as a medicament and/or for use in the manufacture of a medicament for use in the treatment of a cancer such as a hematological malignancy of the blood, bone marrow, and/or lymph nodes, preferably a blood cancer.

Several documents are cited throughout the text of this specification. Each of the documents herein (including any journal article or abstract, published or unpublished patent application, issued patent, manufacturer's specifications, instructions, etc.) are hereby incorporated by reference. However, there is no admission that any document cited herein is indeed prior art in respect of the present invention.

The following examples are intended to illustrate but not to limit the invention.

EXAMPLES hu38SB19 was provided in solution at 5 mg/ml, stored at 4° C. It was diluted into sterile saline in preparation for dosing, stored at 4° C. and used within 10 days of dilution.

Carfilzomib (PR-171) was obtained from Chemie Tek (CT-CARE 98). Carfilzomib was formulated in an aqueous solution of 10% (w/v) sulfobutylether-h-cyclodextrin (Cydex) and 10 mmol/L sodium citrate (pH 3.5), 2 mg/ml stock prepared and frozen at −80° C., diluted daily with vehicle before injection. Carfilzomib was administered weekly qd×2×3 wk (iv).

Example 1

Effect of the Administration of Both Anti-CD38 Antibody and Carfilzomib in a Mice Model of MM These studies under this Example were done under approval of the UCSF IACUC.

The subcutaneous multiple myeloma (MM) xenograft mouse models were established using NCI-H929 or RPMI-8226 cell lines. Specifically, 5-6 week old female Balb/c Scid mice were obtained from Jackson Lab. Mice were housed for 7-10 days prior to implantation. Mice were housed in a dedicated room in the UCSF Mt Zion Animal Barrier Facility. NCI-H929 and RPMI-8226 cells were obtained from the German Collection of Microorganisms and Cell Cultures, DSMZ, (Deutsche Sammlung von Mikroorganismen and Zellkulturen), and grown in sterile suspension culture in T225 flasks as follows: NCI-H929: RPMI1640+20% FBS+4 mM L-glutamine+1 mM sodium pyruvate+50 μM mercaptoethanol. RPMI-8226: RPMI1640+10% FBS+4 mM L-glutamine.

At the time of implantation, mice were shaved on the right flank and shoulder region and anesthetized with ip avertin. MM cells suspended in serum free RPMI 1640 media diluted 1:1 with Matrigel (BD) at a concentration of $1\times10^8$ cells per ml were injected sc into the right flank in 100 μL volume ($1\times10^7$ cells) using a 1 ml syringe and 25 g needle. Mice were monitored twice weekly for the appearance of tumors and once tumors were visible, measurements were collected twice weekly for body weight and tumor volume. Electronic balance and calipers were used and data was collected directly into a study management program (Study Director). When the mean tumor volume reached about 150-200 $mm^3$, the mice were distributed into treatment groups of 8-10 mice per groups and dosing was begun.

The dosing schedule was hu38SB19 was 2×/wk×2 wk (iv, lateral tail vein) and carfilzomib was weekly qd×2×3 wk (iv, lateral tail vein) (once per day, two days a week for three weeks). Dose levels for use in combination studies are as follows:

| Cell Type | Carfilzomib | hu38SB19 |
|---|---|---|
| NCI-H929 | 2 mpk | 0.5 mpk |
| RPMI 8226 | 2.5 mpk | 15 mpk |

mpk = mg per kg body weight

Data were collected using electronic balance and calipers using a study management application called StudyLog (Study Director). Graphs are taken directly from the application. The experimental results are provided in FIGS. 1A-10B.

Based on the single agent results of hu38SB19 and carfilzomib in RPMI-8226 and NCI-H929 multiple myeloma xenograft models, the H929 model appears to be a more sensitive model to both agents while the RPMI model seems to be more resistant to the treatments even at the highest doses tested (FIGS. 1A-7B). Therefore in the combination studies, a suboptimal dose for each agent was chosen to evaluate the activity of the combination treatment (carfilzomib hu38SB19) in the H929 model while higher doses of carfilzomib and hu38SB19 were tested in the RPMI model.

Antitumor activity was determined according to NCI standards based on the ratio of the median tumor volume change of the treated/median tumor volume change of the control×100 (% ΔT/ΔC). Low numerical values for ΔT/ΔC describe stronger anti-tumor activity. Anti-tumor activity is defined as T/C≤40% at minimum. ΔT/ΔC<10% is considered high anti-tumor activity.

Figure 8A:
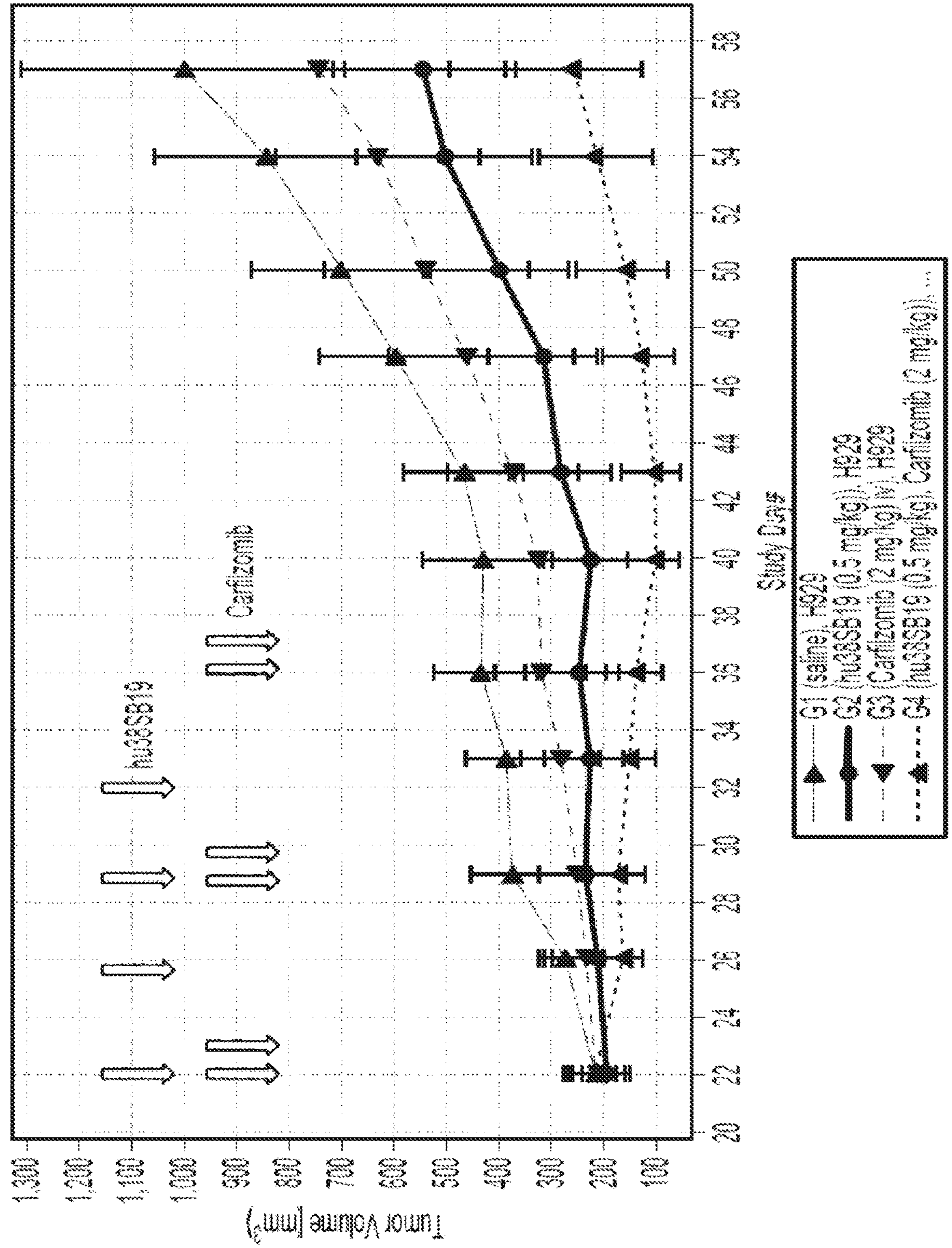
FIG. 8A shows the tumor volume of tumors in H929 models after treatment with the indicated dose of hu38SB19 at the indicated times (top arrows) and the indicated dose of carfilzomib at the indicated times (bottom arrows).
Figure 8B:
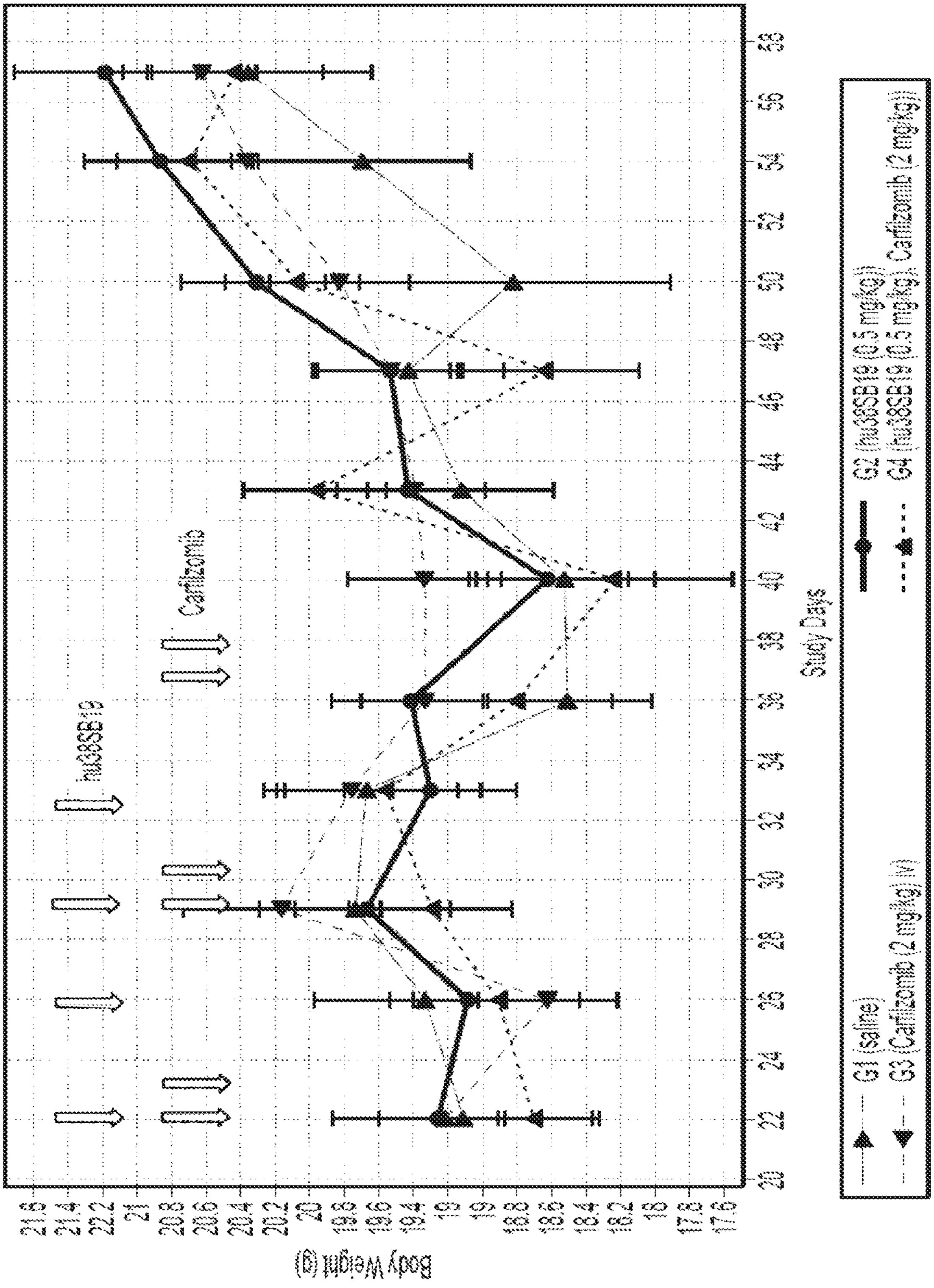
FIG. 8B shows the body weight of the H929 models after treatment indicated dose of hu38SB19 at the indicated times (top arrows) and the indicated dose of carfilzomib at the indicated times (bottom arrows).
Figure 9A:
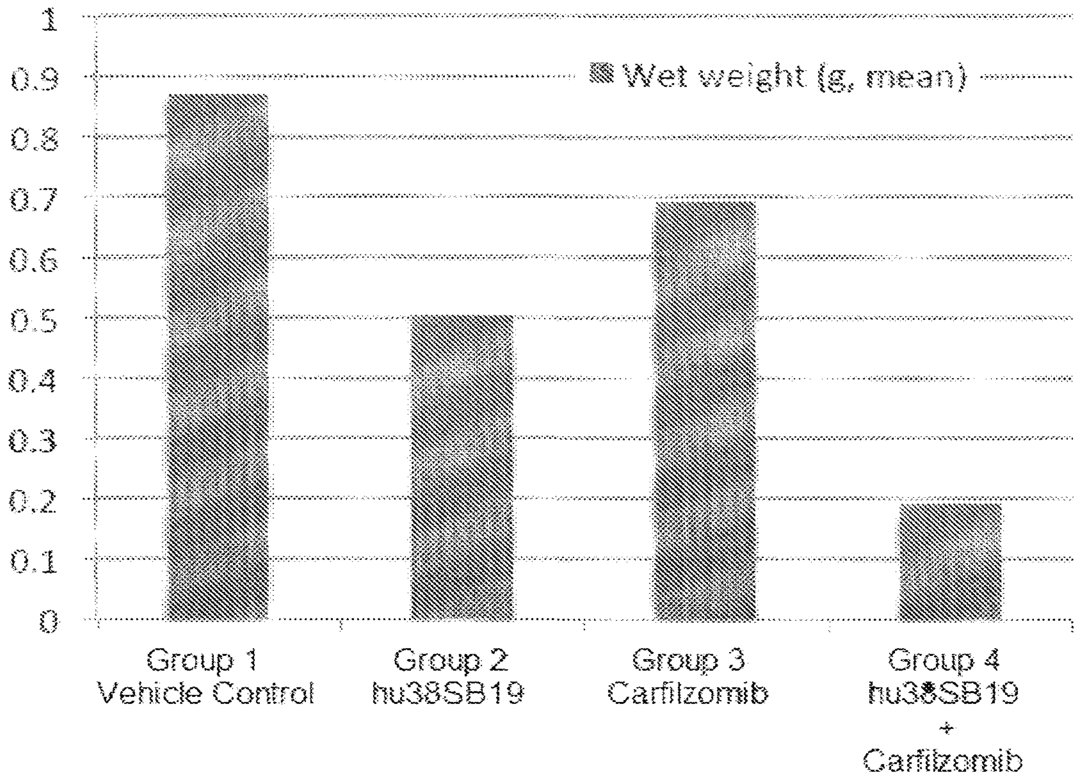
FIG. 9A is a graph showing the mean wet tumor weights of the H929 models after the indicated treatment with carfilzomib and/or hu38SB19 (mAb).
Figure 9B:
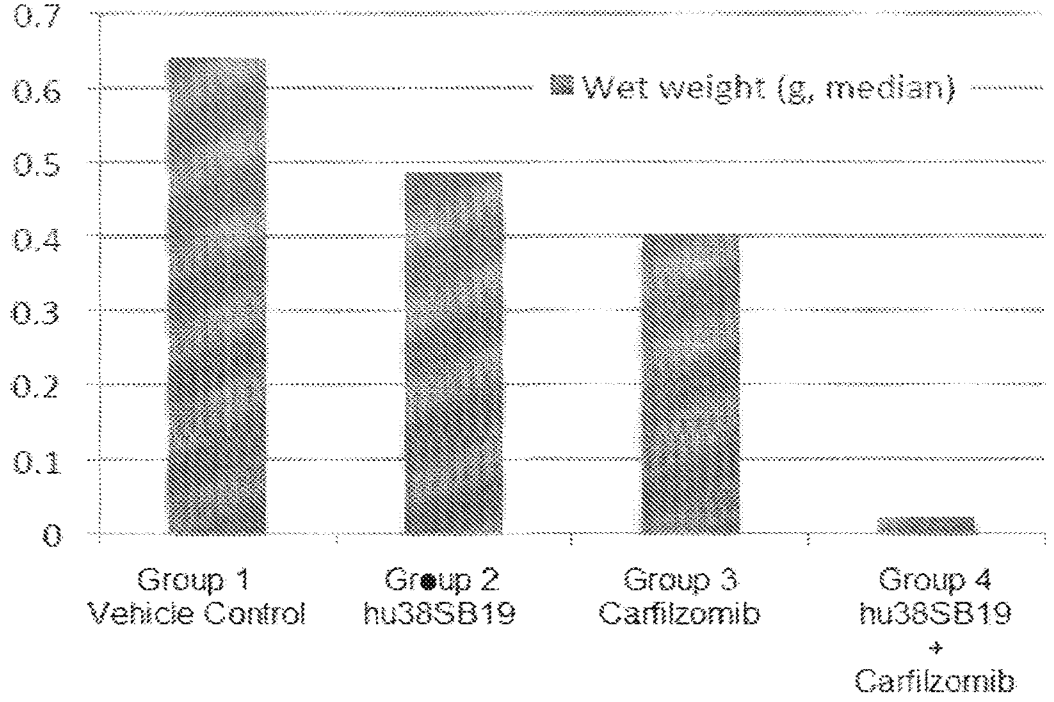
FIG. 9B is a graph showing the median wet tumor weights of the H929 models after the indicated treatment with carfilzomib and/or hu38SB19 (mAb).

In the H929 model, hu38SB19 alone at 0.5 mg/kg/injection (twice a week for 2 weeks) was inactive with a % ΔT/ΔC of 74%. Treatment with carfilzomib alone at 2 mg/kg (twice a week for three weeks) was inactive (68% ΔTΔ/C). The combination of hu38SB19 (0.5 mg/kg/injection) and carfilzomib (2 mg/kg/injection) had much higher activity (tumor regression) with % ΔT/ΔC of −11% (FIG. 8). The results are summarized in Table 1.

TABLE 1

Anti-tumor efficacy of hu38SB19 in combination with carfilzomib against NCI-H929 multiple myeloma model

| Agent | Dose in mg/kg (total dose) | Schedule of Administration IV route | % ΔT/ΔC (D69) | Activity |
|---|---|---|---|---|
| PBS | — | 2×/wk × 2 wk (IV) | | |
| hu38SB19 | 0.5 (2) | 2×/wk × 2 wk (IV) | 74 | Inactive |
| Carfilzomib | 2 (12) | 2×/wk × 3 wk (IV) | 68 | Inactive |
| hu38SB19 + Carfilzomib | 0.5 (2) + 2 (12) | 2×/wk × 2 wk (IV) + 2×/wk × 3 wk (IV) | −11 | Highly Active |

Figure 10A:
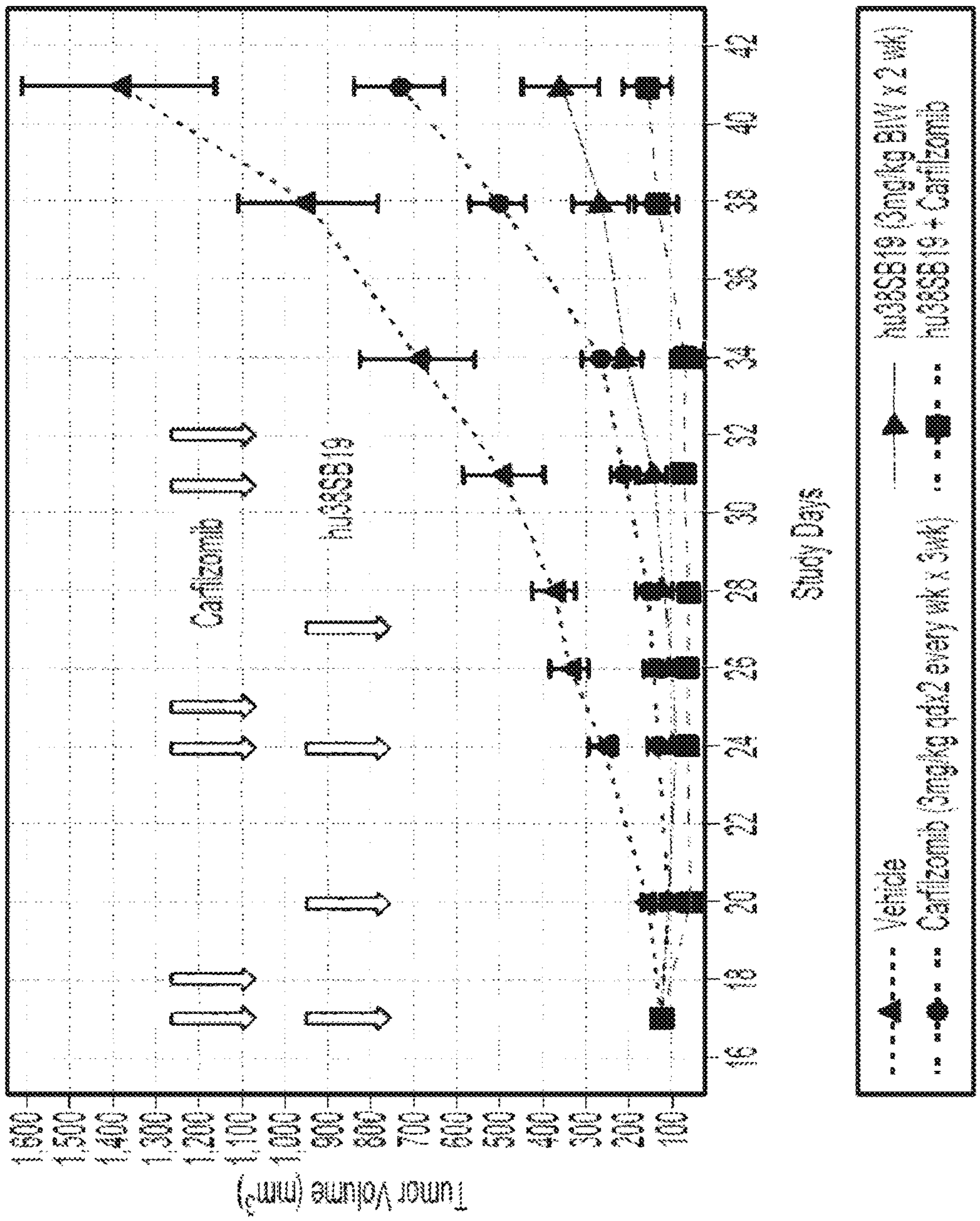
FIG. 10A shows the tumor volume of tumors in RPMI-8226 models after treatment with the indicated dose of hu38SB19 at the indicated times (top arrows) and the indicated dose of carfilzomib at the indicated times (bottom arrows).
Figure 10B:
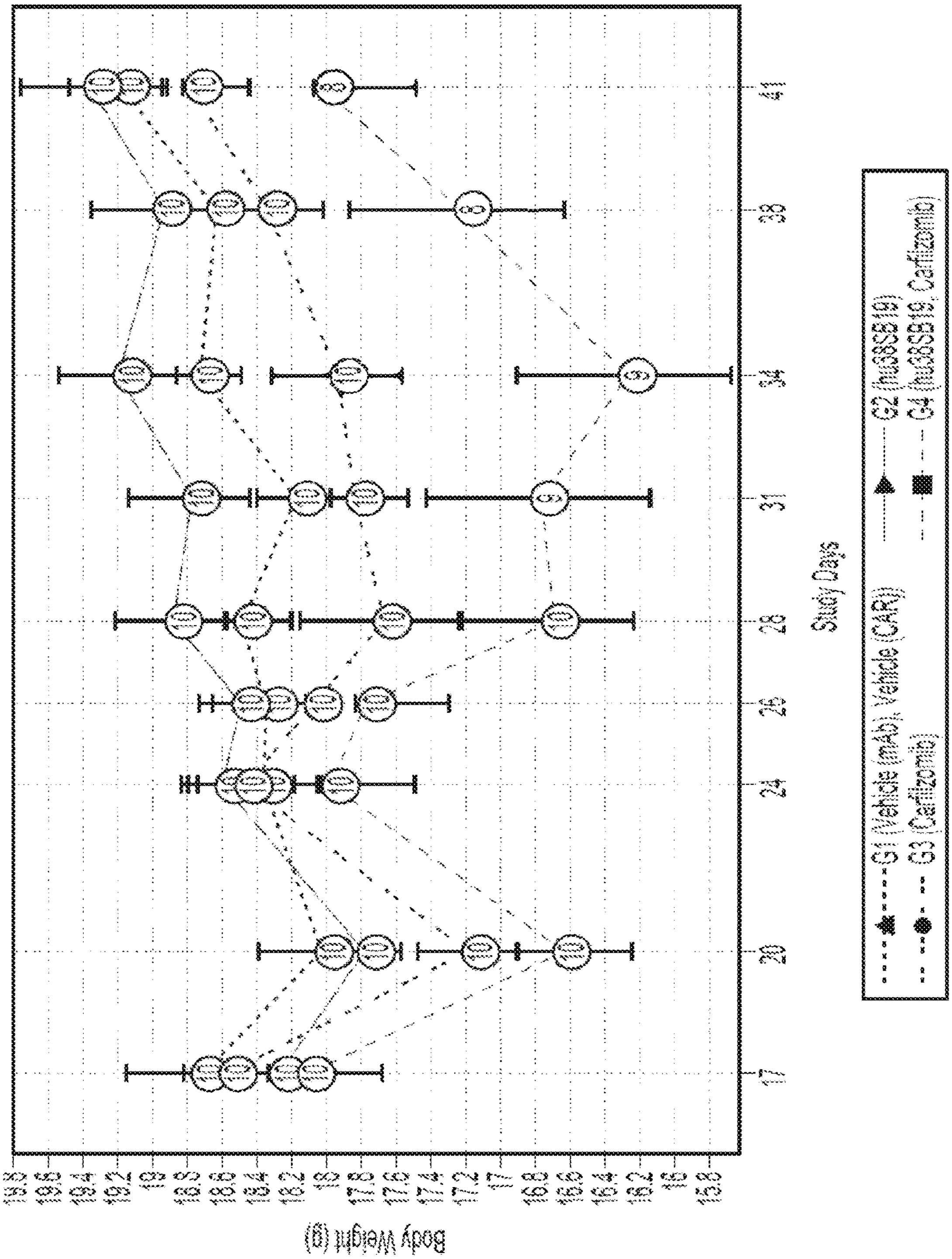
FIG. 10B shows the body weight of the RPMI-8226 models after treatment with the indicated dose of hu38SB19 at the indicated times (top arrows) and the indicated dose of carfilzomib at the indicated times (bottom arrows).

% ΔT/ΔC Median tumor volume change of the treated/Median tumor volume change of the control × 100,
IV = intravenous,
wk = week,
PBS: phosphate buffered saline As shown in FIGS. 10A-10B, similar results were obtained in the RPMI-8226 xenograft models. In particular, on Day 41, carfilzomib (3 mg/kg qd×2 every wk×3 wk) resulted in 0/10 complete regressions; hu38SB19 (3 mg/kg BIW×2 wk) resulted in 2/10 complete regressions. Thus, the additive expectation based on extrapolation for the combination of carfilzomib and hu38SB19 would be expected to be 2/10 complete regressions. However, the combination of carfilzomib and hu38SB19 surprisingly resulted in 5/8 complete regressions which is more than 3 times the expected result.

In both the NCI-H929 and RPMI-8226 xenograft models, the combination treatment inhibited tumor growth to a much greater extent than a single agent alone, indicating the combination of hu38SB19 and carfilzomib blocked tumor cell growth through potential synergistic mechanisms. Carfilzomib is a second generation proteasome inhibitor which was recently approved to treat relapsed and refractory multiple myeloma patients. Inhibition of proteasome activity by carfilzomib results in a build-up of polyubiquinated proteins, which may cause cell cycle arrest, apoptosis, and inhibition of tumor growth. Hu38SB19 has demonstrated multiple mechanisms of action including ADCC, CDC, and direct apoptosis induction.

It has been reported that some CD38 antibodies such as Daratumumab is able to induce apoptosis only after cross-linking with a secondary antibody without much direct effect by itself. However, in preclinical studies, hu38SB19 demonstrated potent direct pro-apoptotic activity on tumor cells without cross-linking. Thus, this unique property of hu38SB19 may also lead to greater tumor cell killing when in combination with carfilzomib compared to other CD38 antibodies combined with carfilzomib.

Example 2

Effect of the Administration of Both Anti-CD38 Antibody and Carfilzomib in Humans A clinical study for evaluating the effects of a treatment with hu38SB19 combined with carfilzomib in patients with relapsed or refractory multiple myeloma may be performed as described below.

The goals of the study may include:

To determine the efficacy and the maximum tolerated dose;

To evaluate the safety, including immunogenicity, of hu38SB19 in combination with carfilzomib in relapse or refractory multiple myeloma. The severity, frequency and incidence of all toxicities is assessed;

To evaluate the pharmacokinetics (PK) of hu38SB19 when administered in combination with carfilzomib and the PK of carfilzomib in combination with hu38SB19, and optionally dexamethasone.

To assess the relationship between clinical (adverse event and/or tumor response) effects and pharmacologic parameters (PK/pharmacodynamics), and/or biologic (correlative laboratory) results;

Estimate the activity (response rate) using International Myeloma Working Group defined response criteria of hu38SB19 plus carfilzomib, and optionally dexamethasone; and To describe overall survival, progression free survival (PFS) and time to disease progression in patients treated with this combination.

Patients with relapsed multiple myeloma who have received at least two prior treatments (including bortezomib and thalidomide and/or lenalidomide) and whose disease has a less than or equal to 25% response to the most recent therapy or has disease progression during or within 60 days of the most recent therapy are enrolled. Patients excluded from the trial are those having total bilirubin levels≥2×upper limit of normal (ULN); creatinine clearance rates<30 mL/min; New York Heart Association Class III to IV congestive heart failure; symptomatic cardiac ischemia; myocardial infarction within the last 6 months; peripheral neuropathy Grade 3 or 4, or peripheral neuropathy Grade 2 with pain; active infections requiring treatment; and pleural effusion.

Carfilzomib is administered intravenously over 2 to 10 minutes on two consecutive days each week for three weeks, followed by a 12-day rest period (28-day treatment cycle), until disease progression, unacceptable toxicity, or for a maximum of 12 cycles. Patients receive 20 mg/$m^2$ at each dose in Cycle 1, and 27 mg/$m^2$ in subsequent cycles. To reduce the incidence and severity of fever, rigors, chills, dyspnea, myalgia, and arthralgia, dexamethasone 4 mg by mouth or by intravenous infusion may be administered prior to all carfilzomib doses during the first cycle and prior to all carfilzomib doses during the first dose-escalation (27 mg/$m^2$) cycle. Dexamethasone premedication (4 mg orally or intravenously) may be reinstated if these symptoms reappeared during subsequent cycles. Doses of hu38SB19 may be administered on the same days the carfilzomib doses are administered and/or on different days. When administered on the same days, hu38SB19 and carfilzomib may be administered at the same time as one composition or as two separate compositions.

The study duration for an individual patient includes a screening period for inclusion of up to 21 days, and at least 4 weeks of treatment in the absence of severe adverse reaction, dose limiting toxicity or disease progression plus up to 60 days post-treatment follow up. The total duration of the study may be up to one year.

The following parameters may be measured during and/or at the end of the study:

Number of patients with adverse events when treated with hu38SB19 in combination with carfilzomib;

Assessment of partial response, complete response, progression free survival, and survival;

Assessment of the following PK parameters: area under curve (AUC), maximum concentration (Cmax) and plasma half-life (T 1/2);

Number of CD38 receptors occupied by hu38SB19; and

Number of anti-SAR antibodies in response to hu38SB19.

Example 3

Efficacy of Anti-CD38 Antibody in In Vivo Tumor Models of Multiple Myeloma as a Single-Agent or in Combination with and Carfilzomib A. Materials and Methods CD38 Density: CD38 density was determined using anti-CD38-PE Quantibrite (BD Biosciences; Cat. 342371) per the manufacturer's recommended protocols.

Reagents & Compounds: hu38SB19 was provided by Sanofi Oncology in solution at 5 mg/ml and stored at 4° C. hu38S1319 was diluted into sterile saline in preparation for dosing and used within 10 days of dilution. hu38SB19 was administered twice weekly×2 wk IV. Carfilzomib (PR-171) was obtained from Chemie Tek (CT-CARP 98). Carfilzomib was formulated in an aqueous solution of 10% (w/v) sulfobutylether-h-cyclodextrin (Cydex) and 10 mmol/L sodium citrate (pH 3.5), 2 mg/ml stock prepared and frozen at −80° C., diluted daily with vehicle before injection. Carfilzomib was administered weekly qd×2×3 wk (iv).

Test Animals: 5-6 week old female Balb/c Scid mice were obtained from Jackson Lab. Mice were housed for 7-10 days prior to implantation of multiple myeloma (MM) cell lines. Mice were housed in a dedicated room in the UCSF Mt. Zion Animal Barrier Facility.

Xenograft Model: At the time of implantation, mice were shaved on the right flank and shoulder. MM cells were suspended in serum free RPMI 1640 media diluted 1:1 with Matrigel (BD) at a concentration of $1\times10^8$ cells per ml were injected sc into the right flank in 100 ul volume ($1\times10^7$ cells) using a 1 ml syringe and 25 g needle. Mice were monitored twice weekly for the appearance of tumors and once tumors were visible, measurements were collected twice weekly for body weight and tumor volume. Electronic balance and calipers were used and data was collected directly into a study management program (Study Director). When the mean tumor volume reached approximately 150-200 $mm^3$, mice were distributed into treatment groups of 8-10 mice per group and dosing was initiated.

Figure 11:
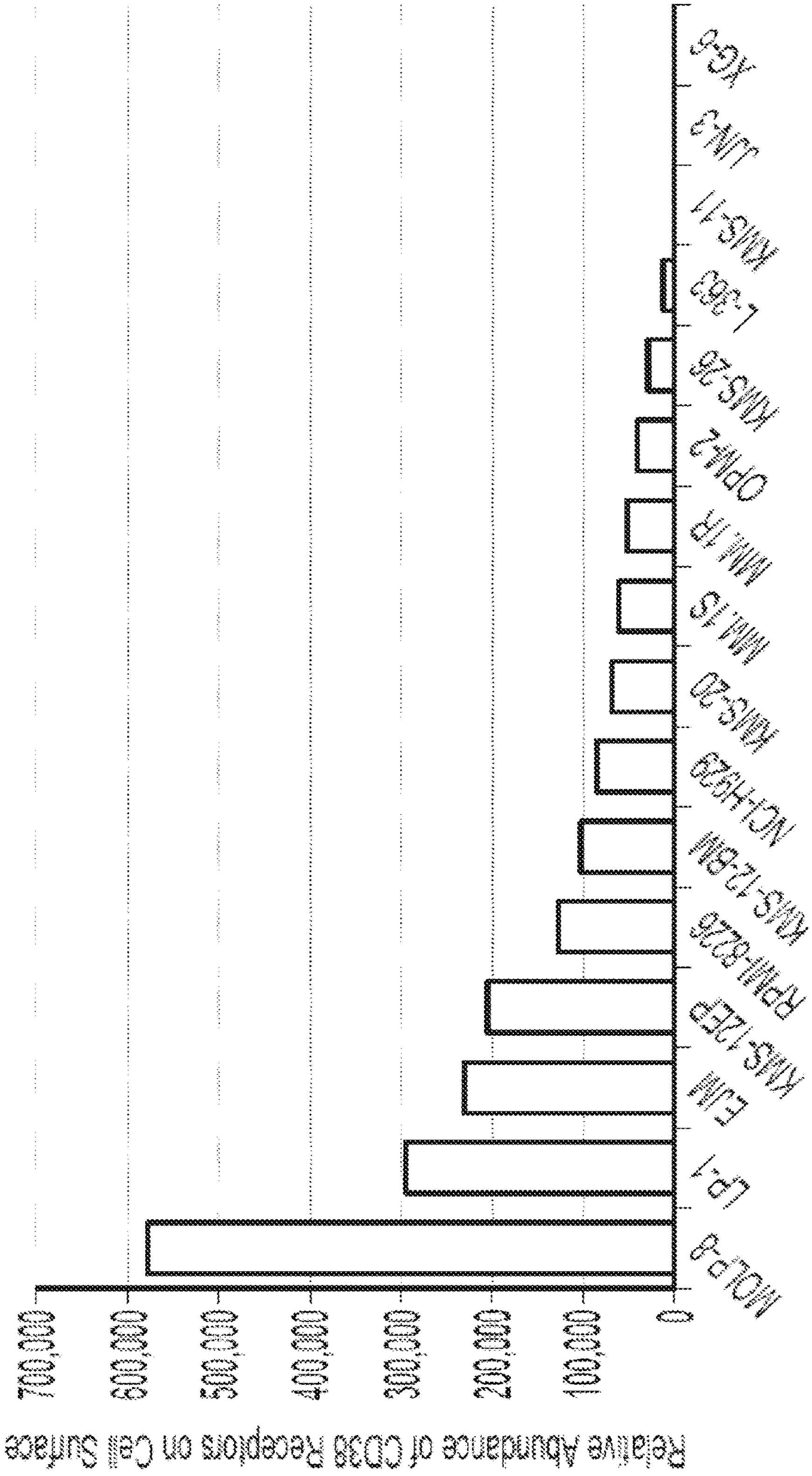
FIG. 11 is a graph showing the cell surface density of CD38 in multiple myeloma cell lines.
Figure 12:
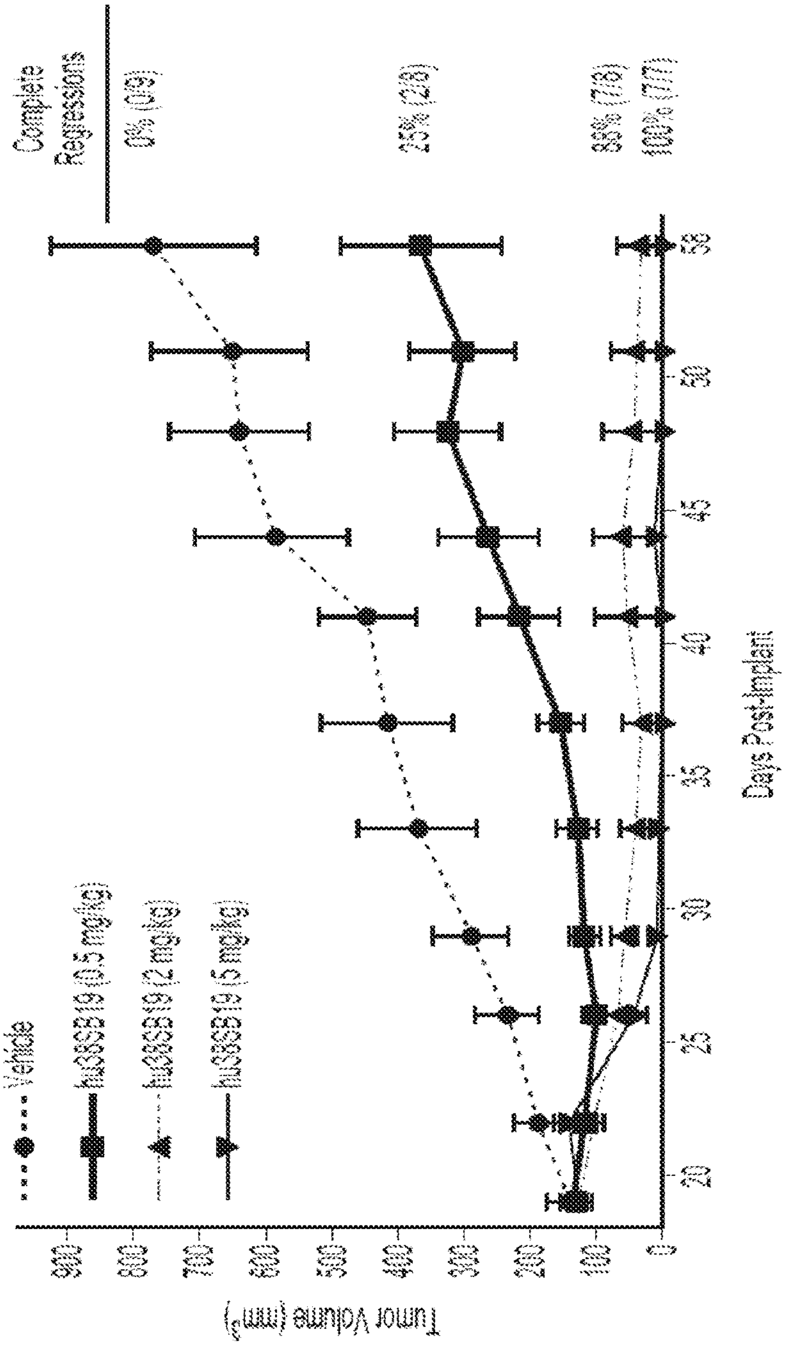
FIG. 12 is a graph showing that hu38SB19, as the sole active ingredient, results in dose-dependent anti-tumor effects and eradication of NCI-H929 hind-flank xenograft tumor growth. Four cumulative doses, given twice weekly at 3 mg/kg were sufficient to eliminate palpable tumors in all mice within the cohort.
Figure 13:
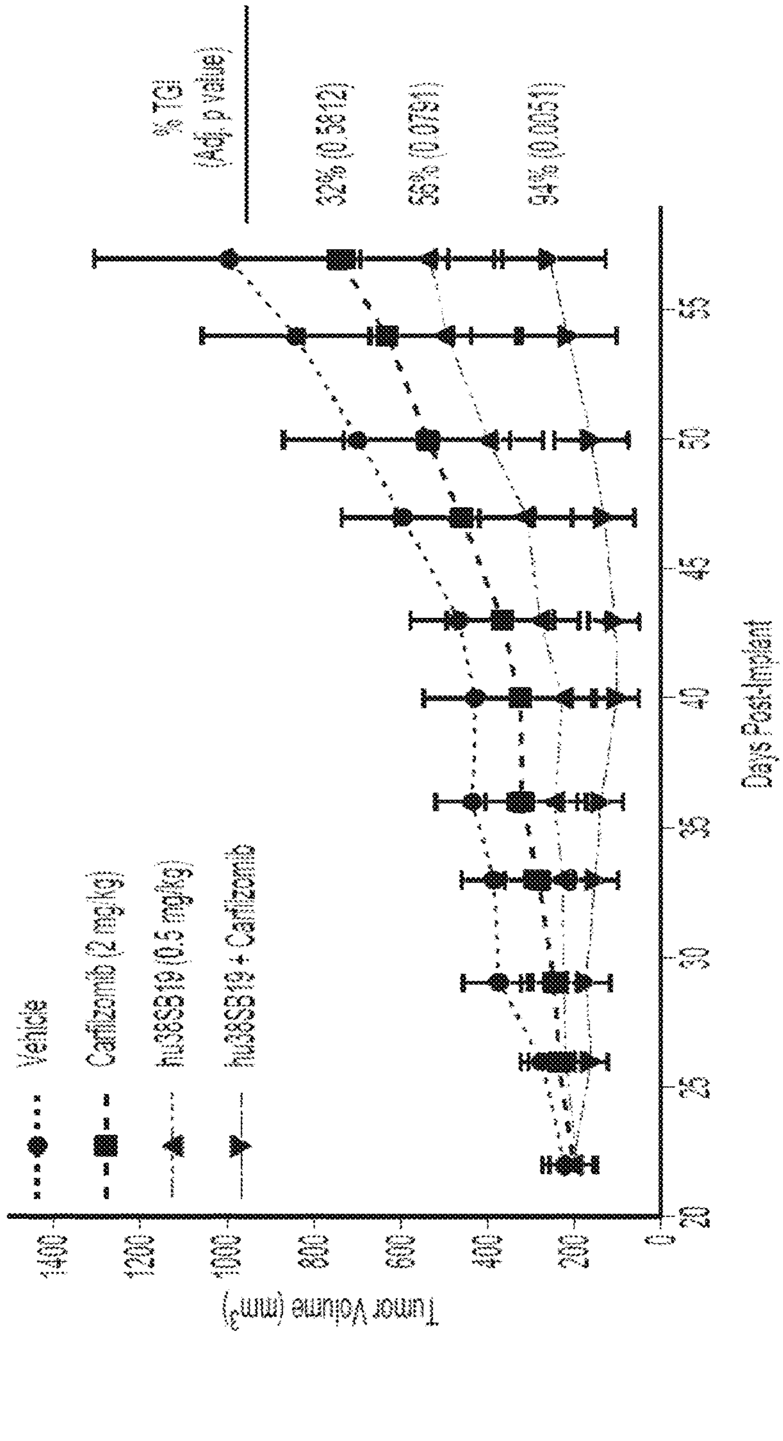
FIG. 13 is a graph showing that low-dose combinations of carfilzomib and hu38SB19 results in near complete tumor growth inhibition of NCI-H929 xenografts.

B. Summary and Conclusions hu38SB19 is a humanized anti-CD38 antibody whose anti-myeloma effects incorporate mechanisms of ADCC, CDC, and direct apoptosis. FIG. 11 shows the cell surface density of CD38 in multiple myeloma cell lines. See Kim D, Park C Y, Medeiros B C, Weissman IL. CD19-CD45 low/−CD38 high/CD138+ plasma cells enrich for human tumorigenic myeloma cells. *Leukemia.* 2012 Dec., 26(12):2530-7. CD38-positive multiple myeloma plasma cells demonstrate variable CD38 cell surface densities. All cell lines, with the exception of XG-6, are reported as CD38-positive. See Bataille R., Jégo G, Robillard N, et al. The phenotype of normal, reactive and malignant plasma cells. Identification of "many and multiple myelomas" and of new targets for myeloma therapy. *Haematologica.* 2006 September, 91(9): 1234-40. Binding of hu38SB19 to CD38 also impinges on the ADPRC enzymatic activity of CD38. In vivo, hu38SB19 demonstrates potent anti-tumor effects in multiple myeloma xenografts, a disease largely characterized by neoplastic plasma cells expressing CD38. FIG. 12 shows that single-agent administration of hu38SB19 results in dose-dependent inhibition of tumor growth in an NCI-H929 hind-flank model. The magnitude and significance of tumor growth inhibition at the end of the study increased with increased doses of hu38SB19. FIG. 13 shows that a combined regimen of hu38SB19 and carfilzomib results in significant tumor growth inhibition in an NCI-H929 xenograft model that is not robustly sensitive to single-agent therapy with carfilzomib. These data demonstrate that single-agent hu38SB19 inhibits growth of NCI-H929 tumors and combines with sub-efficacious doses of carfilzomib to produce significant inhibition of tumor growth. Taken together, these data support further evaluation of hu38SB19, both as a single-agent and in combination with standard-of-care treatment regimens, as a potential therapy for the treatment of multiple myeloma.

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

What is claimed is:

1. A method of treating multiple myeloma in a subject comprising administering an anti-CD38 antibody and carfilzomib to the subject, wherein the anti-CD38 antibody comprises a heavy chain having a VH variable region comprising an amino acid sequence set forth in SEQ ID NO: 66, and a light chain having a $V_L$ variable region comprising an amino acid sequence set forth in either SEQ ID NO: 62 or SEQ ID NO: 64;

wherein the subject has undergone at least two prior therapies for multiple myeloma, and wherein the anti-CD38 antibody and carfilzomib are administered in a synergistic amount.

2. The method of claim 1, wherein the multiple myeloma is a relapsed multiple myeloma or a refractory multiple myeloma.

3. The method of claim 1, wherein the anti-CD38 antibody and carfilzomib are administered in a therapeutically effective amount.

4. The method of claim 1, wherein the anti-CD38 antibody is capable of killing a $CD38^+$ cell by apoptosis, antibody-dependent cell-mediated cytotoxicity (ADCC), and complement-dependent cytotoxicity (CDC).

5. The method of claim 1, wherein the anti-CD38 antibody is administered intravenously.

6. The method of claim 1, wherein carfilzomib is administered intravenously.

7. The method of claim 1, wherein the anti-CD38 antibody and carfilzomib are administered sequentially.

8. The method of claim 1, further comprising administering dexamethasone to the subject.

9. The method of claim 8, wherein dexamethasone is administered orally.

10. The method of claim 8, wherein the anti-CD38 antibody, carfilzomib, and dexamethasone are administered sequentially.

* * * * *